United States Patent [19]

Ducoux et al.

[11] Patent Number: 5,726,313
[45] Date of Patent: Mar. 10, 1998

[54] SUBSTITUTED ARYLALIPHATIC COMPOUNDS, METHOD OF PREPARING THEM AND PHARMACEUTICAL COMPOSITIONS IN WHICH THEY ARE PRESENT

[75] Inventors: Jean-Philippe Ducoux, Montpellier; Patrick Gueule, Teyran; Xavier Emonds-Alt, Combaillaux, all of France

[73] Assignee: Sanofi, Paris, France

[21] Appl. No.: 549,664

[22] PCT Filed: Mar. 29, 1995

[86] PCT No.: PCT/FR95/00391

§ 371 Date: Nov. 29, 1995

§ 102(e) Date: Nov. 29, 1995

[87] PCT Pub. No.: WO95/26338

PCT Pub. Date: Oct. 5, 1995

[30] Foreign Application Priority Data

Mar. 29, 1994 [FR] France ................... 94 03701

[51] Int. Cl.$^6$ ............................. C07D 453/02
[52] U.S. Cl. ........................ 546/133; 546/16; 546/188; 546/217; 546/218; 546/224
[58] Field of Search ................. 514/305, 316, 514/327, 329; 546/133, 217, 218, 224, 188, 16

[56] References Cited

FOREIGN PATENT DOCUMENTS

| A-0 474 561 | 3/1992 | European Pat. Off. . |
| A-0 512 901 | 11/1992 | European Pat. Off. . |
| A-0 599 538 | 9/1993 | European Pat. Off. . |

OTHER PUBLICATIONS

MacLeod et al., *Journal of Medicinal Chemistry*, vol. 37, No. 9, 29 Apr. 1994, 1269–1274.

*Primary Examiner*—C. Warren Ivy
*Assistant Examiner*—Garth M. Dahlen
*Attorney, Agent, or Firm*—Bacon & Thomas

[57] ABSTRACT

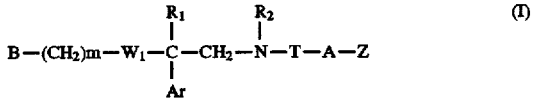

Compound of Formula (I), wherein $W_1$ is an oxygen atom; an —NR— group wherein R is hydrogen, $C_1$–$C_7$ alkyl or benzyl; and B is for example a substituted piperidine or quinuclidine. The disclosed compounds are useful as neurokinin receptor antagonists.

26 Claims, No Drawings

SUBSTITUTED ARYLALIPHATIC COMPOUNDS, METHOD OF PREPARING THEM AND PHARMACEUTICAL COMPOSITIONS IN WHICH THEY ARE PRESENT

This application is a 371 of PCT/FR95/00391, Mar. 29, 1995.

The present invention relates to novel substituted arylaliphatic compounds, to a method of preparing them and to the pharmaceutical compositions in which they are present as the active principle.

More particularly, the present invention relates to a novel class of substituted arylaliphatic compounds for therapeutic use in pathological phenomena involving the tachykinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, U.S. and Pernow ed., 287–293, Raven Press, New York), gastrointestinal disorders (D. Regoli et al., Trends Pharmacol. Sci., 1985, 6, 481–484), respiratory disorders (J. Mizrahi et al., Pharmacology, 1982, 25, 39–50), neurological disorders and neuropsychiatric disorders (C. A. Maggi et al., J. Autonomic Pharmacol., 1993, 13, 23–93), these examples being neither limiting nor exclusive.

In recent years, numerous research studies have been carried out on tachykinins and their receptors. Tachykinins are distributed throughout both the central nervous system and the peripheral nervous system. The tachykinin receptors have been recognized and are classified into three types: $NK_1$, $NK_2$, $NK_3$. Substance P (SP) is the endogenous ligand of the $NK_1$ receptors, neurokinin A ($NK_A$) that of the $NK_2$ receptors and neurokinin B ($NK_B$) that of the $NK_3$ receptors.

The $NK_1$, $NK_2$ and $NK_3$ receptors have been identified in different species.

A recent review by C. A. Maggi et al. looks at the tachykinin receptors and their antagonists and gives an account of the pharmacological studies and the applications in human therapeutics (J. Autonomic Pharmacol., 1993, 13, 23–93).

The following non-peptide compounds may be mentioned among the antagonists specific for the $NK_1$ receptor: CP-96345 (J. Med. Chem., 1992, 35, 2591–2600), RP-68651 (Proc. Natl. Acad. Sci. U.S.A., 1991, 88, 10208–10212), SR 140333 (Curr. J. Pharmacol., 1993, 250, 403–413).

For the $NK_2$ receptor, a non-peptide selective antagonist, SR 48968, has been described in detail (Life Sciences, 1992, 50, PL101–PL106).

As far as the $NK_3$ receptor is concerned, some non-peptide compounds have been described as having an affinity for the $NK_3$ receptor of the rat and guinea-pig brain (FASEB J., 1993, 7 (4), A710, 4104); a peptide antagonist, [$Trp^7,\beta Ala^8$]$NK_A$, which has a week specificity for the $NK_3$ receptor of the rat brain, has also been described (J. Autonomic Pharmacol., 1993, 13, 23–93).

Patent application EP-A-336230 describes peptide derivatives antagonistic towards substance P and neurokinin A which are useful for the treatment and prevention of asthma.

International patent applications WO 90/05525, WO 90/05729, WO 91/09844 and WO 91/18899 and European patent applications EP-A-0436334, EP-A-0429466 and EP-A-0430771 describe substance P antagonists.

European patent applications EP-A-0428434, EP-A-0474561, EP-A-512901, EP-A-0515240, EP-A-0559538, EP-A-591040, EP-A-0625509 and EP-A-0630887 and International patent applications WO 94/10146, WO 94/29309 and WO 94/26735 describe neurokinin receptor antagonists, all of which are characterized by the structure of the formula

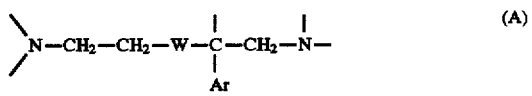

in which W is a direct bond or a methylene.

It has now been found that certain substituted arylaliphatic compounds possess valuable pharmacological properties as neurokinin receptor antagonists and are particularly useful for the treatment of any pathological condition dependent on substance P and neurokinin.

In particular, it has been found that substituted arylaliphatic compounds having the structure of formula (A) above in which W is an oxygen atom or an optionally substituted nitrogen atom possess a very high affinity for the neurokinin receptors.

Thus, according to one of its features, the present invention relates to the compounds of the formula

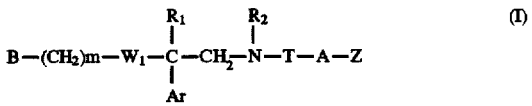

in which:

$W_1$ is an oxygen atom or a group —NR—, in which R is a hydrogen, a ($C_1$–$C_7$)-alkyl or a benzyl;

m is equal to 2 or 3;

$R_1$ is hydrogen or a ($C_1$–$C_4$)-alkyl group;

$R_2$ is a hydrogen, a ($C_1$–$C_7$)-alkyl, an ω-($C_1$–$C_4$)-alkoxy-($C_2$–$C_4$)-alkylene, an ω-($C_2$–$C_4$)-alkylcarbonyloxy-($C_2$–$C_4$)-alkylene, an ω-hydroxy-($C_2$–$C_4$)-alkylene, an ω-($C_1$–$C_4$)-alkylthio-($C_2$–$C_4$)-alkylene, an ω-($C_1$–$C_4$)-alkoxycarbonyl-($C_2$–$C_4$)-alkylene, an ω-carboxy-($C_2$–$C_4$)-alkylene, an ω-($C_1$–$C_4$)-alkylcarbonyl-($C_2$–$C_4$)-alkylene, an ω-benzoyloxy-($C_2$–$C_4$)-alkylene, an ω-benzyloxy-($C_2$–$C_4$)-alkylene, an ω-formyloxy-($C_2$–$C_4$)-alkylene, an ω-$R_5$NHCOO-($C_2$–$C_4$)-alkylene, an ω-$R_6R_7$NCO—($C_2$–$C_4$)-alkylene, an ω-$R_8R_9$N—($C_2$–$C_4$)-alkylene, an ω-$R_{10}$CONR$_{11}$—($C_2$–$C_4$)-alkylene, an ω-$R_{12}$OCONR$_{11}$—($C_2$–$C_4$)-alkylene, an ω-$R_6R_7$NCONR$_{11}$—($C_2$–$C_4$)-alkylene, an ω-$R_{13}$SO$_2$NR$_{11}$—($C_2$–$C_4$)-alkylene or an ω-cyano-($C_1$–$C_3$)-alkylene;

or alternatively $R_1$ and $R_2$ together form a group —(CH$_2$)$_n$—CQ—, where Q=H$_2$ or O and n is equal to 1, 2 or 3;

T is the group —CH$_2$— or one of the groups

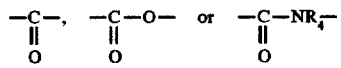

in which $R_4$ is hydrogen or a ($C_1$–$C_4$)-alkyl group, with the proviso that T is —CH$_2$— if Q is oxygen and one of the following groups:

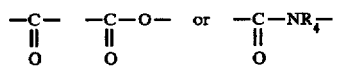

if

Q is hydrogen;

A is a direct bond, a group $—(CH_2)_t—$, in which t is equal to 1, 2 or 3, or a group $—CH=CH—$;

Z is an optionally substituted, mono-, di- or tricyclic aromatic or heteroaromatic group;

Ar is a phenyl which is unsubstituted or monosubstituted or polysubstituted by a substituent selected from a halogen atom, a hydroxyl, a $(C_1-C_4)$-alkoxy, a $(C_1-C_4)$-alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a $(C_1-C_4)$-alkyl or a benzyl; an imidazolyl which is unsubstituted or substituted by a halogen atom; a pyridyl which is unsubstituted or substituted by a halogen atom; or a biphenyl;

$R_5$ is a $(C_1-C_7)$-alkyl or a phenyl;

$R_6$ and $R_7$ are each independently a hydrogen or a $(C_1-C_7)$-alkyl; $R_7$ can also be a $(C_3-C_7)$-cycloalkyl, a $(C_3-C_7)$-cycloalkylmethyl, a phenyl or a benzyl; or alternatively $R_6$ and $R_7$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_8$ and $R_9$ are each independently a hydrogen or a $(C_1-C_7)$-alkyl; $R_9$ can also be a $(C_3-C_7)$-cycloalkylmethyl or a benzyl;

$R_{10}$ is a hydrogen, a $(C_1-C_7)$-alkyl, a vinyl, a phenyl, a benzyl, a pyridyl or a $(C_3-C_7)$-cycloalkyl which is unsubstituted or substituted by one or more methyls;

$R_{11}$ is a hydrogen or a $(C_1-C_7)$-alkyl;

$R_{12}$ is a $(C_1-C_7)$-alkyl or a phenyl;

$R_{13}$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

B is:

i—either a group $B_1$ of the formula

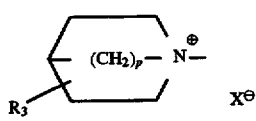

in which:

p is equal to one or two;

$R_3$ is a hydrogen, a $(C_1-C_4)$-alkyl, a phenyl or a benzyl; and $X^\ominus$ is an anion;

ii—or a group $B_2$ of the formula

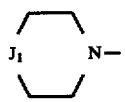

in which $J_1$ is:

$ii_1$—either a group

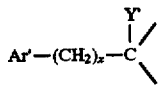

in which:

x is equal to zero or one;

Ar' is a phenyl which is unsubstituted or monosubstituted or polysubstituted by a substituent selected from a halogen atom, a nitro, a hydroxyl, a trifluoromethyl, a $(C_1-C_4)$-alkyl, a $(C_1-C_4)$-alkoxy and a methylenedioxy, said substituents being identical or different; a pyridyl; a thienyl; a pyrimidyl; or an imidazolyl which is unsubstituted or substituted by a $(C_1-C_4)$-alkyl; and Y' is a hydrogen, a $(C_1-C_7)$-alkyl, a formyl, a $(C_1-C_7)$-alkylcarbonyl, a cyano, a group $—(CH_2)_q—OH$, a group $(C_1-C_7)$-alkyl-$O—(CH_2)_q—$, a group $—(CH_2)_q—NR_4COR_{14}$, a group $R_{15}COO—(CH_2)_q—$, a group $(C_1-C_7)$-alkyl-$NHCOO—(CH_2)_q—$, a group $—NR_{16}R_{17}$, a group $—CH_2—NR_{18}R_{19}$, a group $—CH_2—CH_2—NR_{18}R_{19}$, a group $—(CH_2)_q—NR_4COOR_{20}$, a group $—(CH_2)_q—NR_4SO_2R_{21}$, a group $—(CH_2)_q—NR_4CONR_{22}R_{23}$, a carboxyl, a $(C_1-C_7)$-alkoxycarbonyl, a group $—CONR_{22}R_{23}$, a carboxymethyl, a $(C_1-C_7)$-alkoxycarbonylmethyl, a group $—CH_2—CONR_{22}R_{23}$, a mercapto or a $(C_1-C_4)$-alkylthio;

or alternatively Y' forms an additional bond with the carbon atom to which it is bonded and with the adjacent carbon atom in the piperidine;

q is equal to zero, one or two;

$R_4$ is a hydrogen or a $(C_1-C_4)$-alkyl;

$R_{14}$ is a hydrogen, a $(C_1-C_7)$-alkyl, a phenyl, a pyridyl, a vinyl, a benzyl or a $(C_3-C_7)$-cycloalkyl which is unsubstituted or substituted by one or more methyls;

or $R_4$ and $R_{14}$ together are a group $—(CH_2)_u—$, in which u is equal to three or four;

$R_{15}$ is a hydrogen; a $(C_1-C_7)$-alkyl; a $(C_3-C_7)$-cycloalkyl which is unsubstituted or substituted by one or more methyls; a phenyl; or a pyridyl;

$R_{16}$ and $R_{17}$ are each independently a hydrogen or a $(C_1-C_7)$-alkyl; $R_{17}$ can also be a $(C_3-C_7)$-cycloalkylmethyl, a benzyl or a phenyl; or alternatively $R_{16}$ and $R_{17}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_{18}$ and $R_{19}$ are each independently a hydrogen or a $(C_1-C_7)$-alkyl; $R_{19}$ can also be a $(C_3-C_7)$-cycloalkylmethyl or a benzyl;

$R_{20}$ is a $(C_1-C_7)$-alkyl or a phenyl;

$R_{21}$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

$R_{22}$ and $R_{23}$ are each independently a hydrogen or a $(C_1-C_7)$-alkyl; $R_{23}$ can also be a $(C_3-C_7)$-cycloalkyl, a $(C_3-C_7)$-cycloalkylmethyl, a hydroxyl, a $(C_1-C_4)$-alkoxy, a benzyl or a phenyl;

or alternatively $R_{22}$ and $R_{23}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

ii$_2$—or a group

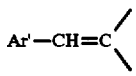

in which

Ar' is as defined above;
ii$_3$—or a group

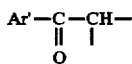

in which

Ar' is as defined above;
ii$_4$—or a group

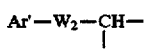

in which:

Ar' is as defined above;
$W_2$ is an oxygen atom, a sulfur atom, a sulfinyl, a sulfonyl or a group —$NR_{24}$—;
$R_{24}$ is a hydrogen, a $(C_1-C_4)$-alkyl, a $(C_1-C_4)$-alkylcarbonyl or a group —$(CH_2)_v$—$NR_{25}R_{26}$;
v is equal to one, two or three; and
$R_{25}$ and $R_{26}$ are each independently a hydrogen or a $(C_1-C_4)$-alkyl; or alternatively $R_{25}$ and $R_{26}$, together with the nitrogen atom to which they are bonded, form a heterocycle selected from pyrrolidine, piperidine and morpholine;

iii—or a group $B_3$ of the formula

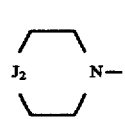

in which $J_2$ is:

iii$_1$—either a group

iii$_2$—or a group

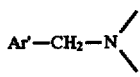

iii$_3$—or a group

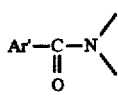

iii$_4$—or a group

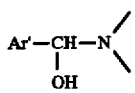

iii$_5$—or a group

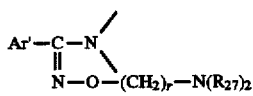

in which groups:
Ar' is as defined above;
r is two or three; and
$R_{27}$ is a $(C_1-C_4)$-alkyl;
iv—or a group $B_4$ of the formula

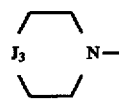

in which
$J_3$ is:
a group

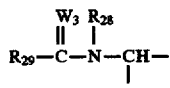

in which:
$W_3$ is an oxygen atom, a sulfur atom or a group $NR_{30}$, in which $R_{30}$ is a hydrogen or a $(C_1-C_3)$-alkyl;
$R_{28}$ is a hydrogen; a $(C_1-C_6)$-alkyl; a $(C_3-C_6)$-alkenyl in which a vinylic carbon atom is not bonded to the nitrogen atom; a 2-hydroxyethyl; a $(C_3-C_7)$-cycloalkyl; a phenyl which is unsubstituted or monosubstituted or polysubstituted by a substituent selected from a halogen atom, a trifluoromethyl, a $(C_1-C_4)$-alkyl, a $(C_1-C_4)$-alkoxy, a nitro, an amino and a hydroxyl, said substituents being identical or different; or a 6-membered heteroaryl containing one or two nitrogen atoms as heteroatoms, said heteroaryl being unsubstituted or monosubstituted or polysubstituted by a substituent selected from a halogen atom, a trifluoromethyl, a $(C_1-C_4)$-alkyl, a $(C_1-C_4)$-alkoxy, a nitro, an amino and a hydroxyl, said substituents being identical or different;

$R_{29}$ is a hydrogen; a $(C_1-C_6)$-alkyl which is unsubstituted or substituted by a hydroxyl and/or by one, two or three fluorine atoms; a $(C_3-C_6)$-cycloalkyl; a $(C_1-C_5)$-alkoxy (only if $W_3$ is an oxygen atom); a $(C_3-C_6)$-cycloalkoxy (only if $W_3$ is an oxygen atom); a group —$NR_{31}R_{32}$ containing from zero to seven carbon atoms, $R_{29}$ being other than an unsubstituted $(C_1-C_4)$-alkyl if $W_3$ is an oxygen atom and simultaneously $R_{28}$ is a phenyl which is unsubstituted or substituted one or more times by a substituent selected from a halogen atom, a nitro, a hydroxyl, a trifluoromethyl, a $(C_1-C_4)$-alkyl and a $(C_1-C_4)$-alkoxy, said substituents being identical or different; a pyridyl; a pyrimidyl; or an imidazolyl which is unsubstituted or substituted by a $(C_1-C_4)$-alkyl;

or alternatively $R_{28}$ and $R_{29}$ together form a divalent hydrocarbon group L, in which the 1-position is bonded to the carbon atom carrying the substituent $W_3$, the divalent hydrocarbon group L being selected from a trimethylene, a cis-propenylene, a tetramethylene, a cis-butenylene, a cis-but-3-enylene, a cis,cis-butadienylene, a pentamethylene and a cis-pentenylene, said divalent hydrocarbon group L being unsubstituted or substituted by one or two methyls; and $R_{31}$ and $R_{32}$ are each independently a hydrogen, a $(C_1-C_5)$-alkyl or a $(C_3-C_6)$-cycloalkyl; or alternatively $R_{31}$ and $R_{32}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$-alkyl;

v—or a group $B_5$ of the formula

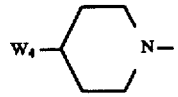

in which:

$W_4$ is a $(C_1-C_8)$-alkyl or a $(C_3-C_8)$-cycloalkyl, said alkyl and cycloalkyl groups being unsubstituted or substituted by one or more substituents selected from a halogen atom; a $(C_3-C_6)$-cycloalkyl; a cyano; a nitro; a hydroxyl; a $(C_1-C_4)$-alkoxy; a formyloxy; a $(C_1-C_4)$-alkylcarbonyloxy; an arylcarbonyl; a heteroarylcarbonyl; an oxo; an imino which is unsubstituted or substituted on the nitrogen atom by a $(C_1-C_6)$-alkyl, a $(C_3-C_6)$-cycloalkyl, a formyl, a $(C_1-C_4)$-alkylcarbonyl or an arylcarbonyl; a hydroxyimino which is unsubstituted or substituted on the oxygen atom by a $(C_1-C_4)$-alkyl or a phenyl; a group —$NR_{33}R_{34}$ containing from zero to seven carbon atoms; a group —$NR_{35}R_{36}$; a group —$C(=NR_{37})NR_{38}R_{39}$, in which the group —$NR_{38}R_{39}$ contains from zero to seven carbon atoms; or a group —$CON(OR_{40})R_{41}$, said substituents being identical or different;

$R_{33}$ and $R_{34}$ are each independently a hydrogen, a $(C_1-C_5)$-alkyl or a $(C_3-C_6)$-cycloalkyl; or alternatively $R_{33}$ and $R_{34}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $C_1-C_4$-alkyl;

$R_{35}$ is a hydrogen or a $(C_1-C_4)$-alkyl;

$R_{36}$ is a formyl; a $(C_1-C_4)$-alkylcarbonyl; an arylcarbonyl; a heteroarylcarbonyl; or a group —$C(=W_5)$—$NR_{38}R_{39}$, in which the group —$NR_{38}R_{39}$ contains from zero to seven carbon atoms;

$W_5$ is an oxygen atom, a sulfur atom, a group —$NR_{37}$ or a group —$CHR_{42}$;

$R_{37}$ is a hydrogen or a $(C_1-C_4)$-alkyl; or alternatively $R_{37}$ and $R_{39}$ together form an ethylene group or a trimethylene group;

$R_{38}$ and $R_{39}$ are each independently a hydrogen, a $(C_1-C_5)$-alkyl or a $(C_3-C_6)$-cycloalkyl; or alternatively $R_{38}$ and $R_{39}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$-alkyl; or alternatively $R_{38}$ is a hydrogen or a $(C_1-C_4)$-alkyl and $R_{39}$ and $R_{37}$ together form an ethylene group or a trimethylene group;

$R_{40}$ and $R_{41}$ are each independently a $(C_1-C_3)$-alkyl;

$R_{42}$ is a cyano, a nitro or a group $SO_2R_{43}$; and $R_{43}$ is a $(C_1-C_4)$-alkyl or a phenyl;

and if $W_4$ is a cyclic group or if a substituent of $W_4$ is a cyclic group or contains a cyclic group, said cyclic groups can additionally be substituted on a carbon atom by one or more $(C_1-C_3)$-alkyls, and if a substituent of $W_4$ contains an aryl group or a heteroaryl group, said aryl or heteroaryl groups can additionally be monosubstituted or polysubstituted by a substituent selected from a halogen atom, a $(C_1-C_4)$-alkyl, a $(C_1-C_4)$-alkoxy, a cyano, a trifluoromethyl and a nitro, said substituents being identical or different;

vi—or a group $B_6$ of the formula

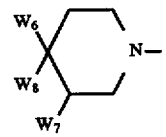

in which:

$W_6$ and $W_7$ are each a hydrogen, or alternatively $W_6$ is a hydrogen and $W_7$ is a hydroxyl;

$W_8$ is an aryl or a heteroaryl which is unsubstituted or substituted by an aryl, an arylcarbonyl, a heteroaryl or a heteroarylcarbonyl, said aryl or heteroaryl groups can additionally be monosubstituted or polysubstituted on the aromatic or heteroaromatic moiety and on a carbon atom by a substituent selected from a halogen atom; a cyano; a trifluoromethyl; a nitro; a hydroxyl; a $(C_1-C_5)$-alkoxy; a formyloxy; a $(C_1-C_4)$-alkylcarbonyloxy; a group —$NR_{33}R_{34}$ containing from zero to seven carbon atoms; a group —$NR_{35}R_{36}$; a group —$C(=NR_{37})NR_{38}R_{39}$, in which the group —$NR_{38}R_{39}$ contains from zero to seven carbon atoms; a group —$COOR_{44}$; a group —$CONR_{45}R_{46}$, in which the group $NR_{45}R_{46}$ contains from zero to seven carbon atoms; a mercapto; a group —$S(O)_zR_{47}$; a $(C_1-C_5)$-alkyl; a formyl; and a $(C_1-C_4)$-alkylcarbonyl, said substituents being identical or different; if $W_6$ and $W_7$ are each a hydrogen, $W_8$ is other than a phenyl which is unsubstituted or substituted one or more times by a substituent selected from a halogen atom, a nitro, a hydroxyl, a trifluoromethyl and a $(C_1-C_4)$-alkoxy, said substituents being identical or different; other than a pyridyl; other than a pyrimidyl; or other than an imidazolyl which is unsubstituted or substituted by a (C$_1$-C$_4$)-alkyl;

or alternatively W$_7$ is a hydrogen and W$_6$ and W$_8$, together with a diradical W$_9$ and the carbon atom of the piperidine to which they are bonded, form a spiro ring in which W$_8$ is a phenyl substituted in the ortho-position by a diradical W$_9$, which is itself joined to W$_6$, said phenyl being unsubstituted or substituted by a substituent selected from a halogen atom, a (C$_1$-C$_3$)-alkyl, a (C$_1$-C$_3$)-alkoxy, a hydroxyl, a (C$_1$-C$_3$)-alkylthio, a (C$_1$-C$_3$)-alkylsulfinyl and a (C$_1$-C$_3$)-alkylsulfonyl; the diradical W$_9$ is a methylene, a carbonyl or a sulfonyl; and W$_6$ is an oxygen atom or a group —NR$_{48}$—, in which R$_{48}$ is a hydrogen or a (C$_1$-C$_3$)-alkyl;

R$_{33}$, R$_{34}$, R$_{35}$, R$_{36}$, R$_{37}$, R$_{38}$ and R$_{39}$ are as defined above for the group B$_5$;

R$_{44}$ is a hydrogen, a (C$_1$-C$_5$)-alkyl, an aryl, a heteroaryl, an arylmethyl or a heteroarylmethyl;

R$_{45}$ and R$_{46}$ are each independently a hydrogen, a (C$_1$-C$_5$)-alkyl or a (C$_3$-C$_6$)-cycloalkyl; or alternatively R$_{45}$ and R$_{46}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a (C$_1$-C$_4$)-alkyl;

s is zero, one or two; and

R$_{47}$ is a (C$_1$-C$_6$)-alkyl, a (C$_3$-C$_6$)-cycloalkyl, an aryl or a heteroaryl;

and if W$_8$ or a substituent of W$_8$ contains a cyclic group, said cyclic group can additionally be substituted by one or more methyls, and if a heteroaryl group forming part of W$_8$ or of a substituent of W$_8$ contains a nitrogen atom as the heteroatom, said nitrogen atom can additionally be substituted by a (C$_1$-C$_5$)-alkyl, and if W$_8$ or a substituent of W$_8$ contains a (C$_1$-C$_5$)-alkyl, (C$_1$-C$_5$)-alkoxy, formyl or (C$_1$-C$_4$)-alkylcarbonyl group, said (C$_1$-C$_5$)-alkyl, (C$_1$-C$_5$)-alkoxy, formyl or (C$_1$-C$_4$)-alkylcarbonyl groups can additionally be substituted by a hydroxyl, a (C$_1$-C$_3$)-alkoxy or one or more halogen atoms, with the proviso that a carbon atom bonded to a nitrogen atom or to an oxygen atom is not substituted by a hydroxyl or an alkoxy group, and with the proviso that a carbon atom in the α-position of a (C$_1$-C$_4$)-alkylcarbonyl group is not substituted by a chlorine, bromine or iodine atom;

vii—or a group B$_7$ of the formula

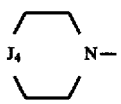

in which

J$_4$ is:

vii$_1$—either a group

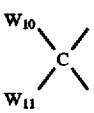

in which:

W$_{10}$ is a phenyl which is unsubstituted or monosubstituted to trisubstituted by a substituent selected from a halogen atom, a (C$_1$-C$_6$)-alkoxy, a (C$_1$-C$_6$)-alkyl and a trifluoromethyl, said substituents being identical or different; a benzyl which is unsubstituted or monosubstituted to trisubstituted by a substituent selected from a halogen atom, a (C$_1$-C$_6$)-alkoxy, a (C$_1$-C$_6$)-alkyl and a trifluoromethyl, said substituents being identical or different; a naphthyl which is unsubstituted or monosubstituted to trisubstituted by a substituent selected from a halogen atom, a (C$_1$-C$_6$)-alkoxy, a (C$_1$-C$_6$)-alkyl and a trifluoromethyl, said substituents being identical or different; a pyridyl which is unsubstituted or monosubstituted or disubstituted by a substituent selected from a halogen atom, a (C$_1$-C$_6$)-alkyl and a (C$_1$-C$_6$)-alkoxy, said substituents being identical or different; or a thienyl;

—W$_{11}$ is a group —CONHR$_{49}$; and

—R$_{49}$ is a group CH$_3$—CHOH—CH—COO—(C$_1$-C$_6$)-alkyl, a group (C$_1$-C$_6$)-alkyl—OCO—CH$_2$—CH$_2$—CH—COO—(C$_1$-C$_6$)-alkyl or a group —CH$_2$CH$_2$N(CH$_3$)$_2$;

vii$_2$—or a group

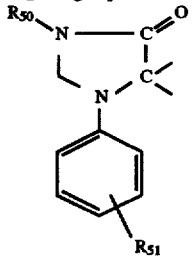

vii$_3$—or a group

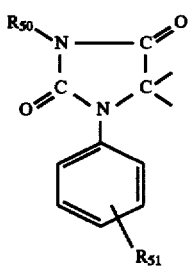

vii$_4$—or a group

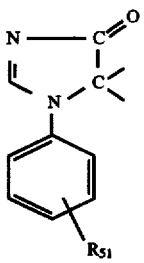

in which groups:

R$_{50}$ is a hydrogen, a (C$_1$-C$_6$)-alkyl or a benzyl; and

R$_{51}$ is from one to three substituents selected from a hydrogen, a halogen atom, a trifluoromethyl, a (C$_1$-C$_6$)-alkyl and a (C$_1$-C$_6$)-alkoxy, said substituents being identical or different;

vii—or a group $B_8$ of the formula

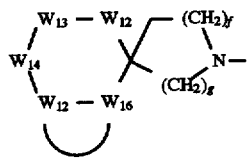

in which:

f and g are each independently zero, one, two, three, four or five, with the proviso that f+g is equal to one, two, three, four or five;

$W_{12}$ is a direct bond; a $(C_1-C_3)$-alkylene which is unsubstituted or substituted by an oxo, a group $OR_{52}$, a halogen, a trifluoromethyl or a phenyl which is itself unsubstituted or mono-, di- or tri-substituted by a substituent selected independently from a hydroxyl, a cyano, a halogen and a trifluoromethyl; a group —$S(O)_k$—; a group $(C_1-C_3)$-alkylene-$S(O)_k$—; a group —$S(O)_k$—$(C_1-C_2)$-alkylene; a group —$S(O)_k$—NH—; a group —$S(O)_j$—$NR_{52}$—; a group —$S(O)_j$—$NR_{52}$—$(C_1-C_2)$-alkylene; a group —$CONR_{52}$—; a group —$CONR_{52}$—$(C_1-C_2)$-alkylene; a group —COO—; or a group —COO—$(C_1-C_2)$-alkylene;

$W_{13}$ is a group —$NR_{53}$—, an oxygen atom, a sulfur atom, a sulfinyl or a sulfonyl, with the proviso that if $W_{12}$ is a direct bond and if $W_{14}$ is a $(C_1-C_3)$-alkylene, $W_{13}$ is a group —$NR_{53}$—;

$W_{14}$ is a direct bond; a $(C_1-C_3)$-alkylene which is unsubstituted or substituted by an oxo, a group $OR_{52}$, a halogen, a trifluoromethyl or a phenyl which is itself unsubstituted or mono-, di- or tri-substituted by a substituent selected independently from a group $OR_{52}$, a halogen and a trifluoromethyl; a group —$S(O)_k$—; a group $(C_1-C_3)$-alkylene-$S(O)_k$—; a group —$S(O)_k$—$(C_1-C_2)$-alkylene; a group —$NHS(O)_j$—; a group —NH—$(C_1-C_2)$-alkylene-$S(O)_j$—; a group —$S(O)_j NR_{52}$—; a group —$S(O)_j$—$NR_{52}$—$(C_1-C_2)$-alkylene; a group —NHCO—$(C_1-C_2)$-alkylene; a group —$NR_{52}$—CO—; a group —$NR_{52}$—$(C_1-C_2)$-alkylene-CO—; a group —OCO—; or a group $(C_1-C_2)$-alkylene-OCO—;

$W_{15}$–$W_{16}$ together form two adjacent atoms of a cyclic radical of the formula

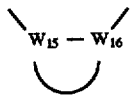

said cyclic radical being a phenyl, a naphthyl or a heteroaryl group selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidyl, a pyrrolyl, a quinolyl, a tetrazolyl, a thiadiazolyl, a thiazolyl, a thienyl and a triazolyl, and said phenyl, naphthyl or heteroaryl cyclic radical being unsubstituted or mono-, di- or tri-substituted by $R_{54}$;

k is zero, one or two;

j is one or two;

$R_{52}$ is a hydrogen; a $(C_1-C_6)$-alkyl which is unsubstituted or monosubstituted or disubstituted by a substituent selected independently from a hydroxyl, an oxo, a cyano, a halogen atom, a trifluoromethyl and a phenyl which is itself unsubstituted or substituted by a hydroxyl, a $(C_1-C_3)$-alkyl, a cyano, a halogen, a trifluoromethyl or a $(C_1-C_4)$-alkoxy; a phenyl, a pyridyl or a thiophene, said phenyl, pyridyl or thiophene being unsubstituted or mono-, di- or tri-substituted by a substituent selected independently from a hydroxyl, a $(C_1-C_4)$-alkyl, a cyano, a halogen atom and a trifluoromethyl; or a $(C_1-C_3)$-alkoxy;

$R_{53}$ is a hydrogen; a $(C_1-C_8)$-alkyl which is unsubstituted or monosubstituted or polysubstituted by a substituent selected from a group —$OR_{52}$, an oxo, a group —$NHCOR_{52}$, a group —$NR_{55}R_{56}$, a cyano, a halogen atom, a trifluoromethyl and a phenyl which is itself unsubstituted or substituted by a hydroxyl, a cyano, a halogen atom or a trifluoromethyl; a group —S(O)—$R_{57}$; a group —$CO_2R_{57}$—; a group —$SO_2R_{57}$; a group —$COR_{57}$; or a group —$CONR_{56}R_{57}$;

$R_{54}$ is a hydrogen; a $(C_1-C_6)$-alkyl which is unsubstituted or monosubstituted or disubstituted by a hydrogen or a hydroxyl; an oxo; a group —$OR_{52}$; a halogen atom; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR_{55}S(O)_jR_{56}$; a group —$CONR_{55}R_{56}$; a group —$COR_{52}$; a group —$CO_2R_{52}$; a group —$S(O)_jR_{52}$; or a heteroaryl group, said heteroaryl being selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidinyl, a pyrrolyl, a quinolyl, a tetrazolyl, a thiadiazolyl, a thiazolyl, a thienyl and a triazolyl, and said heteroaryl being unsubstituted or monosubstituted or disubstituted by $R_{58}$;

$R_{55}$ is $R_{52}$;

$R_{56}$ is $R_{52}$;

or alternatively $R_{55}$ and $R_{56}$, together with the atoms to which they are bonded, form a five-, six- or seven-membered saturated monocyclic heterocycle containing one or two heteroatoms, said heteroatoms being selected independently from a nitrogen atom, an oxygen atom and a sulfur atom, said heterocycle being unsubstituted or monosubstituted or disubstituted by a substituent selected independently from a hydroxyl, an oxo, a cyano, a halogen atom and a trifluoromethyl;

$R_{57}$ is a $(C_1-C_6)$-alkyl which is unsubstituted or mono-, di- or tri-substituted by a substituent selected from a hydroxyl, an oxo, a cyano, a group a group —$NR_{55}R_{56}$, a group —$NR_{55}COR_{56}$, a halogen atom, a trifluoromethyl and a phenyl which is itself unsubstituted or mono-, di- or tri-substituted by a substituent selected independently from a hydroxyl, an oxo, a cyano, a group —$NHR_{52}$, a group —$NR_{55}R_{56}$, a group —$NR_{55}COR_{56}$, a halogen atom, a trifluoromethyl and a $(C_1-C_3)$-alkyl; and $R_{58}$ is a hydrogen; a $(C_1-C_6)$-alkyl which is unsubstituted or monosubstituted or disubstituted by a hydrogen or a hydroxyl; an oxo; a group —$OR_{52}$; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR_{55}S(O)_jR_{56}$; a group —$CONR_{55}R_{56}$; a group —$COR_{52}$; a group —$CO_2R_{52}$; a group —$S(O)_jR_{52}$; or a phenyl;

and the group $B_8$ being other than the group $B_6$ if $W_7$ is a hydrogen and $W_6$ and $W_8$, together with a diradical $W_9$ and the carbon atom of the piperidine to which they are bonded, form a spiro ring; and their salts, where appropriate, with mineral or organic acids.

The compounds of formula (I) according to the invention include the optically pure isomers as well as the racemates.

More particularly, the radical Z can be a phenyl group, which can be unsubstituted or may contain one or more substituents.

If Z is a phenyl group, it can be monosubstituted or disubstituted, especially in the 2,4-position, but also for example in the 2,3-, 4,5-, 3,4- or 3,5-position; it can also be trisubstituted, especially in the 2,4,6-position, but also for example in the 2,3,4-, 2,3,5-, 2,4,5- or 3,4,5-position, tetrasubstituted, for example in the 2,3,4,5-position, or pentasubstituted.

The radical Z can also be a bicyclic aromatic group such as 1- or 2-naphthyl or 1-, 2-, 3-, 4-, 5-, 6- or 7-indenyl, in which one or more bonds can be hydrogenated, it being possible for said groups to be unsubstituted or optionally to contain one or more substituents such as the alkyl, phenyl, cyano, hydroxyalkyl, hydroxyl, oxo, alkylcarbonylamino, alkoxycarbonyl, thioalkyl, halogen, alkoxy or trifluoromethyl group, in which the alkyl and alkoxy groups are $C_1$–$C_4$.

The radical Z can also be a pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl, chromanyl or carboxyaryl, in which one or more double bonds can be hydrogenated, it being possible for said groups to be unsubstituted or optionally to contain one or more substituents such as the alkyl, phenyl, cyano, hydroxyalkyl, hydroxyl, alkylcarbonylamino, alkoxycarbonyl or thioalkyl group, in which the alkyl and alkoxy groups are $C_1$–$C_4$.

In particular, the invention relates to compounds of formula (I) in which:

Z is Z' and is:
  a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a ($C_1$–$C_4$)-alkyl; a benzylamino; a carboxyl; a ($C_1$–$C_{10}$)-alkyl; a ($C_3$–$C_8$)-cycloalkyl which is unsubstituted or monosubstituted or polysubstituted by a methyl; a ($C_1$–$C_{10}$)-alkoxy; a ($C_3$–$C_8$)-cycloalkoxy which is unsubstituted or monosubstituted or polysubstituted by a methyl; a mercapto; a ($C_1$–$C_{10}$)-alkylthio; a formyloxy; a ($C_1$–$C_6$)-alkylcarbonyloxy; a formylamino; a ($C_1$–$C_6$)-alkylcarbonylamino; a benzoylamino; a ($C_1$–$C_4$)-alkoxycarbonyl; a ($C_3$–$C_7$)-cycloalkoxycarbonyl; a carbamoyl which is unsubstituted or monosubstituted or disubstituted by a ($C_1$–$C_4$)-alkyl; a ureido which is unsubstituted or monosubstituted or disubstituted in the 3-position by a ($C_1$–$C_4$)-alkyl or a ($C_3$–$C_7$)-cycloalkyl; or a (pyrrolidin-1-yl)carbonylamino, said substituents being identical or different;
  a naphthyl which is unsubstituted or monosubstituted or polysubstituted by a halogen, a trifluoromethyl, a ($C_1$–$C_4$)-alkyl, a hydroxyl or a ($C_1$–$C_4$)-alkoxy; or
  a pyridyl, a thienyl, an indolyl, a quinolyl, a benzothienyl or an imidazolyl.

Advantageously, the invention relates to the compounds of formula (I) in which:

$W_1$ is an oxygen atom;

B is:
  i—either the group $B_1$ of the formula

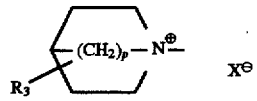

in which
  p=1 or 2, $R_3$ is hydrogen, a ($C_1$–$C_4$)-alkyl or the phenyl group and $X^\ominus$ is an anion;
  ii—or the group $B_2$ of the formula

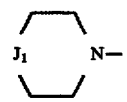

in which $J_1$ is the group

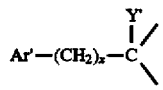

in which:

x is zero;

Ar' is an unsubstituted phenyl group; a phenyl group monosubstituted or polysubstituted by a halogen, a nitro group, a hydroxyl group, a trifluoromethyl group, a ($C_1$–$C_4$)-alkyl group or a ($C_1$–$C_4$)-alkoxy group; or a pyridyl group;

Y' is a hydroxyl group, an amino group, a group ($C_1$–$C_7$)-alkyl-O—$(CH_2)_q$—, a group —$(CH_2)_q$—$NR_4COR_{14}$ or a group $R_{15}COO$—$(CH_2)_q$—;

q is equal to zero;

$R_4$ is hydrogen or a ($C_1$–$C_4$)-alkyl group;

$R_{14}$ is a ($C_1$–$C_7$)-alkyl, a phenyl or a pyrid-2-yl;

$R_{15}$ is a ($C_1$–$C_7$)-alkyl;

m is equal to 2 or 3;

$R_1$ is hydrogen or a ($C_1$–$C_4$)-alkyl group;

$R_2$ is a hydrogen, a ($C_1$–$C_4$)-alkyl, an ω-($C_1$–$C_4$)-alkoxy-($C_2$–$C_4$)-alkylene, an ω-($C_1$–$C_4$)-alkylcarbonyloxy-($C_2$–$C_4$)-alkylene, an ω-hydroxy-($C_2$–$C_4$)-alkylene, an ω-($C_1$–$C_4$)-alkylthio-($C_2$–$C_4$)-alkylene, an ω-($C_1$–$C_4$)-alkoxycarbonyl-($C_2$–$C_4$)-alkylene, an ω-carboxy-($C_2$–$C_4$)-alkylene, an ω-($C_1$–$C_4$)-alkylcarbonyl-($C_2$–$C_4$)-alkylene or an ω-benzoyloxy-($C_2$–$C_4$)-alkylene;

or alternatively $R_1$ and $R_2$ together form a group —$(CH_2)_n$—$CQ$—, where $Q=H_2$ or O and n is equal to 1, 2 or 3;

T is the group —$CH_2$— or one of the groups

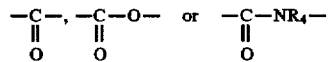

in which $R_4$ is hydrogen or a ($C_1$–$C_4$)-alkyl group, with the proviso that T is —$CH_2$— if Q is oxygen and one of the following groups:

$$-\underset{\underset{O}{\|}}{C}-, \quad -\underset{\underset{O}{\|}}{C}-O- \quad \text{or} \quad -\underset{\underset{O}{\|}}{C}-NR_4-$$

if Q is hydrogen;

A is a direct bond, a group —$(CH_2)_t$—, in which t is equal to 1, 2 or 3, or a group —CH=CH—;

Z is an unsubstituted phenyl; a phenyl monosubstituted or polysubstituted by a halogen, a hydroxyl group, a nitro group, a $(C_1-C_4)$-alkyl group, a trifluoromethyl group or a $(C_1-C_4)$-alkoxy group; a 1-naphthyl group; or a 2-naphthyl group; and Ar is an unsubstituted phenyl group; a phenyl group monosubstituted or polysubstituted by a substituent selected from a halogen atom, a trifluoromethyl, a hydroxyl, a $(C_1-C_4)$-alkoxy and a $(C_1-C_4)$-alkyl, said substituents being identical or different; a thienyl; a benzothienyl; a naphthyl; or an indolyl optionally N-substituted by a $(C_1-C_4)$-alkyl or a benzyl;

and their salts, where appropriate, with mineral or organic acids.

It is possible to form salts of the compounds of formula (I) in addition to the quaternary salts. These salts also include those with mineral or organic acids which permit a suitable separation or crystallization of the compounds of formula (I), such as picric acid, oxalic acid or an optically active acid, for example a mandelic or camphosulfonic acid, and mineral or organic acids which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, glycolate, gluconate, citrate, isethionate, benzenesulfonate or paratoluenesulfonate.

The anions $X^\ominus$ are those normally used to salify quaternary ammonium ions and are preferably chloride, bromide, iodide, hydrogensulfate, methanesulfonate, paratoluenesulfonate, acetate and benzenesulfonate ions.

In the present description, the alkyl or alkoxy groups are linear or branched; halogen atom is understood as meaning a chlorine, bromine, fluorine or iodine atom.

In the present description, if B is a group $B_5$ or $B_6$, aryl is understood as meaning a phenyl radical or a $C_9-C_{10}$ ortho-fused bicyclic carbocyclic radical in which at least one of the rings is aromatic; heteroaryl is understood as meaning either a five- or six-membered monocyclic aromatic heterocycle containing from one to four heteroatoms, said heteroatoms being selected from oxygen, sulfur and nitrogen atoms and said heterocycle being bonded by a carbon atom of the ring, or an eight- to ten-membered ortho-fused bicyclic aromatic heterocycle containing from one to four heteroatoms as defined above.

In the substituents of the group Z=phenyl, $(C_1-C_{10})$-alkyl is understood as meaning for example a methyl, an ethyl, an n-propyl, an isopropyl, an n-butyl, an isobutyl, a sec-butyl, a tert-butyl, a pentyl or n-pentyl, a hexyl or n-hexyl, a heptyl or n-heptyl, an octyl or n-octyl, a nonyl or n-nonyl or a decyl or n-decyl; $(C_3-C_8)$-cycloalkyl optionally substituted by a methyl is understood as meaning for example a cyclopropyl, a cyclobutyl, a cyclopentyl, a 1-, 2- or 3-methylcyclopentyl, a cyclohexyl, a 1-, 2-, 3- or 4-methylcyclohexyl a cycloheptyl or a cyclooctyl; $(C_1-C_{10})$-alkoxy is understood as meaning for example a methoxy, an ethoxy, an n-propoxy, an isopropoxy, an n-butoxy, an isobutoxy, a sec-butoxy, a tert-butoxy, a pentoxy, a hexyloxy a heptyloxy, an octyloxy, a nonyloxy or a decyloxy; $(C_3-C_8)$-cycloalkoxy optionally substituted by a methyl is understood as meaning for example a cyclopropoxy, a cyclobutoxy, a cyclopentoxy, a 1-, 2- or 3-methylcyclopentoxy, a cyclohexyloxy, a 1-, 2-, 3- or 4-methylcyclohexyloxy, a cycloheptyloxy or a cyclooctyloxy; $(C_1-C_{10})$-alkylthio is understood as meaning for example a methylthio, an ethylthio, an n-propylthio, an isopropylthio, an n-butylthio, an isobutylthio, a sec-butylthio, a tert-butylthio, a pentylthio, a hexylthio, a heptylthio, an octylthio, a nonylthio or a decylthio; $(C_1-C_6)$-alkylcarbonyloxy is understood as meaning for example an acetoxy, a propionyloxy, a butyryloxy, a valeryloxy, a caproyloxy or a heptanoyloxy; $(C_1-C_6)$-alkylcarbonylamino is understood as meaning for example an acetylamino, a propionylamino, a butyrylamino, an isobutyrylamino, a valerylamino, a caproylamino or a heptanoylamino; $(C_1-C_4)$-alkoxycarbonyl is understood as meaning for example a methoxycarbonyl, an ethoxycarbonyl, an n-propoxycarbonyl, an isopropoxycarbonyl, an n-butoxycarbonyl, an isobutoxycarbonyl, a sec-butoxycarbonyl or a tert-butoxycarbonyl; $(C_3-C_7)$-cycloalkoxycarbonyl is understood as meaning for example a cyclopropoxycarbonyl, a cyclobutoxycarbonyl, a cyclopentoxycarbonyl, a cyclohexyloxycarbonyl or a cycloheptyloxycarbonyl.

Advantageously, the radical Z is a phenyl which is unsubstituted or monosubstituted or polysubstituted by a halogen atom, more particularly a chlorine, fluorine or iodine atom, a trifluoromethyl, a $(C_1-C_4)$-alkyl, a hydroxyl or a $(C_1-C_4)$-alkoxy; a naphthyl which is unsubstituted or monosubstituted or polysubstituted by a halogen, a trifluoromethyl, a $(C_1-C_4)$-alkyl, a hydroxyl or a $(C_1-C_4)$-alkoxy; a pyridyl; a thienyl; an indolyl; a quinolyl; a benzothienyl; or an imidazolyl.

The substituent Ar is preferably a phenyl group which is advantageously substituted by two chlorine atoms or two fluorine atoms, more particularly in the 3- and 4-positions.

The compounds of formula (I) in which simultaneously:

$R_1$ and $R_2$ together form a group —$(CH_2)_n$—CQ— in which n is equal to 2 and Q is $H_2$ or oxygen;

$W_1$ is an oxygen atom;

Ar is a 3,4-dichlorophenyl or a 3,4-difluorophenyl;

Z=Z'; and m, B, T and A are as defined above for (I), and the salts and solvates thereof, especially those which are pharmaceutically acceptable, are preferred compounds.

The compounds of formula (I) in which simultaneously:

$R_1$ is hydrogen;

$R_2$ is a methyl group;

$W_1$ is an oxygen atom;

m is equal to 2;

Ar is a 3,4-dichlorophenyl or a 3,4-difluorophenyl;

Z=Z'; and

B, T and A are as defined above for (I), and the salts and solvates thereof, especially those which are pharmaceutically acceptable, are preferred compounds.

The compounds of formula (I) in which simultaneously:

$R_1$ is hydrogen;

$R_2$ is a methyl group;

$W_1$ is a group —NR— in which R is a methyl group;

Ar is a 3,4-dichlorophenyl or a 3,4-difluorophenyl;

Z=Z'; and m, B, T and A are as defined above for (I), and the salts and solvates thereof, especially those which are pharmaceutically acceptable, are preferred compounds.

The compounds of formula (I) in which simultaneously:

$R_1$ and $R_2$ together form a group —$(CH_2)_n$—CQ— in which n is equal to 2 and Q is $H_2$ or oxygen;

$W_1$ is an oxygen atom;

Ar is an unsubstituted phenyl group; a phenyl group monosubstituted or polysubstituted by a substituent selected from a halogen atom, a trifluoromethyl, a hydroxyl, a $C_1$-$C_4$-alkoxy and a $C_1$-$C_4$-alkyl, said substituents being identical or different; a thienyl; a benzothienyl; a naphthyl; or an indolyl optionally N-substituted by a $C_1$-$C_6$-alkyl or a benzyl;

Z is an unsubstituted phenyl; a phenyl monosubstituted or polysubstituted by a halogen, a hydroxyl group, a nitro group, a ($C_1$-$C_4$)-alkyl group, a trifluoromethyl group or a ($C_1$-$C_4$)-alkoxy group; a 1-naphthyl group; or a 2-naphthyl group;

m, T and A are as defined above for (I);

B is:
i—either the group $B_1$ of the formula

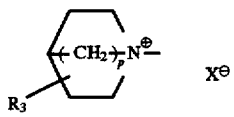

in which p=1 or 2, $R_3$ is hydrogen, a ($C_1$-$C_4$)-alkyl or the phenyl group and $X^\ominus$ is an anion;

ii—or the group $B_2$ of the formula

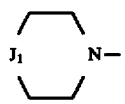

in which $J_1$ is the group

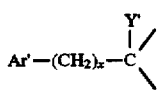

in which:

x is zero;

Ar' is an unsubstituted phenyl group; a phenyl group monosubstituted or polysubstituted by a halogen, a nitro group, a hydroxyl group, a trifluoromethyl group, a ($C_1$-$C_4$)-alkyl group or a ($C_1$-$C_4$)-alkoxy group; or a pyridyl group;

Y' is a hydroxyl group, an amino group, a group ($C_1$-$C_7$)-alkyl-O—$(CH_2)_q$—, a group —$(CH_2)_q$—$NR_4COR_{14}$ or a group $R_{15}$COO—$(CH_2)_q$—; and q is equal to zero, and the salts and solvates thereof, especially those which are pharmaceutically acceptable, are also preferred compounds.

The compounds of formula (I) in which simultaneously:

$R_1$ is hydrogen;

$R_2$ is a methyl group;

$W_1$ is an oxygen atom;

m is equal to 2;

Ar is an unsubstituted phenyl group; a phenyl group monosubstituted or polysubstituted by a substituent selected from a halogen atom, a trifluoromethyl, a hydroxyl, a $C_1$-$C_4$-alkoxy and a $C_1$-$C_4$-alkyl, said substituents being identical or different; a thienyl; a benzothienyl; a naphthyl; or an indolyl optionally N-substituted by a $C_1$-$C_4$-alkyl or a benzyl;

Z is an unsubstituted phenyl; a phenyl monosubstituted or polysubstituted by a halogen, a hydroxyl group, a nitro group, a ($C_1$-$C_4$)-alkyl group, a trifluoromethyl group or a ($C_1$-$C_4$)-alkoxy group; a 1-naphthyl group; or a 2-naphthyl group;

T and A are as defined above for (I);

B is:
i—either the group $B_1$ of the formula

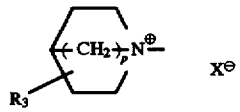

in which p=1 or 2, $R_3$ is hydrogen, a ($C_1$-$C_4$)-alkyl or the phenyl group and $X^\ominus$ is an anion;

ii—or the group $B_2$ of the formula

in which $J_1$ is the group

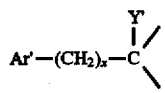

in which:

x is zero;

Ar' is an unsubstituted phenyl group; a phenyl group monosubstituted or polysubstituted by a halogen, a nitro group, a hydroxyl group, a trifluoromethyl group, a ($C_1$-$C_4$)-alkyl group or a ($C_1$-$C_4$)-alkoxy group; or a pyridyl group;

Y' is a hydroxyl group, an amino group, a group ($C_1$-$C_7$)-alkyl-O—$(CH_2)_q$—, a group —$(CH_2)_q$—$NR_4COR_{14}$ or a group $R_{15}$COO—$(CH_2)_q$—; and q is equal to zero, and the salts and solvates thereof, especially those which are pharmaceutically acceptable, are also preferred compounds.

The following are particularly preferred among these compounds:

4-phenyl-1-[2-[3-(3,4-dichlorophenyl)-1-(3-isopropoxybenzylcarbonyl)piperid-3-yloxy]ethyl]quinuclidinium chloride;

4-phenyl-4-propionyloxy-1-[2-[3-(3,4-dichlorophenyl)-1-benzoylpiperid-3-yloxy]ethyl]piperidine hydrochloride;

4-acetamido-4-phenyl-1-[2-[1-(3,4-dichlorophenyl)-2-(N-methyl-N-benzyloxycarbonylamino)ethoxy]ethyl]piperidine hydrochloride;

4-acetamido-4-phenyl-1-[2-[1-(3,4-dichlorophenyl)-2-(N-methyl-N-phenylcarbonylamino)ethoxy]ethyl]piperidine hydrochloride;

4-benzyl-1-[2-[3-(3,4-dichlorophenyl)-1-(3-isopropoxybenzylcarbonyl)piperid-3-yloxy]ethyl]quinuclidinium chloride;

19

4-phenyl-1-[2-[N-methyl-N-[1-(3,4-dichlorophenyl)-2-[N'-methyl-N'-(3-isopropoxybenzylcarbonyl)amino]ethyl]amino]ethyl]quinuclidinium chloride hydrochloride.

According to another of its features, the present invention relates to the preparation of the compounds of formula (I) and the salts thereof.

One of the preparative methods according to the invention (method A) is suitable for obtaining the compounds of formula (I) in which simultaneously $R_1$ and $R_2$ together form a group —$(CH_2)_n$—CQ in which Q is oxygen, and $W_1$ is an oxygen atom.

This method consists in:

1) treating a compound of the formula $$\begin{array}{c} (CH_2)_n\text{---}C{\Large\diagup\!\!\!\!\diagdown}^O \\ | \quad\quad\quad | \\ E_1\text{---}O\text{---}C\text{---}CH_2\text{---}NH \\ | \\ Ar \end{array} \quad (II)$$

in which Ar is as defined above for a compound of formula (I) and $E_1$ is an O-protecting group, in particular the tetrahydropyran-2-yl group, with a halogenated derivative of the formula $$Hal\text{-}CH_2\text{---}A\text{---}Z \quad (III)$$

in which Hal is a halogen atom, preferably bromine, and A and Z are as defined above for a compound of formula (I), if it is intended to prepare a compound of formula (I) in which T is —$CH_2$—, in the presence of a base such as, for example, sodium hydride or potassium tert-butylate, in order to form the compound of the formula $$\begin{array}{c} (CH_2)_n\text{---}C{\Large\diagup\!\!\!\!\diagdown}^O \\ | \quad\quad\quad | \\ E_1\text{---}O\text{---}C\text{---}CH_2\text{---}N\text{---}CH_2\text{---}A\text{---}Z \\ | \\ Ar \end{array} \quad (IV)$$

2) eliminating the protecting group $E_1$ by reaction with an acid;

3) treating the resulting compound of formula (V):

$$\begin{array}{c} (CH_2)_n\text{---}C{\Large\diagup\!\!\!\!\diagdown}^O \\ | \quad\quad\quad | \\ H\text{---}O\text{---}C\text{---}CH_2\text{---}N\text{---}CH_2\text{---}A\text{---}Z \\ | \\ Ar \end{array} \quad (V)$$

with a compound of formula (VI): $Hal\text{-}(CH_2)_m\text{---}O\text{---}E_2$, in which $E_2$ is an O-protecting group such as the tetrahydropyran-2-yl group, Hal is a halogen atom, preferably bromine, and m is as defined for a compound of formula (I), in order to form the compound of formula (VII):

$$\begin{array}{c} (CH_2)_n\text{---}C{\Large\diagup\!\!\!\!\diagdown}^O \\ | \quad\quad\quad | \\ E_2\text{---}O\text{---}(CH_2)_m\text{---}O\text{---}C\text{---}CH_2\text{---}N\text{---}CH_2\text{---}A\text{---}Z \\ | \\ Ar \end{array} \quad (VII)$$

in which $E_2$, m, Ar, A and Z are as defined above;

4) removing the protecting group $E_2$ by reaction with an acid;

20

5) treating the resulting compound of formula (VIII):

$$\begin{array}{c} (CH_2)_n\text{---}C{\Large\diagup\!\!\!\!\diagdown}^O \\ | \quad\quad\quad | \\ HO\text{---}(CH_2)_m\text{---}O\text{---}C\text{---}CH_2\text{---}N\text{---}CH_2\text{---}A\text{---}Z \\ | \\ Ar \end{array} \quad (VIII)$$

with a compound of the formula $$G\text{---}SO_2\text{---}Cl \quad (XXIX)$$

in which G is a methyl, phenyl, tolyl or trifluoromethyl group;

6) reacting the resulting sulfonate of the formula $$\begin{array}{c} (CH_2)_n\text{---}C{\Large\diagup\!\!\!\!\diagdown}^O \\ | \quad\quad\quad | \\ G\text{---}SO_2O\text{---}(CH_2)_m\text{---}O\text{---}C\text{---}CH_2\text{---}N\text{---}CH_2\text{---}A\text{---}Z \\ | \\ Ar \end{array} \quad (IX)$$

either with a cyclic secondary amine of the formula $$\begin{array}{c} \diagup\!\!\!\!\!\diagdown \\ J'_1 \quad NH \\ \diagdown\!\!\!\!\!\diagup \end{array} \quad (Xa)$$

in which $J'_1$ is:

either a group

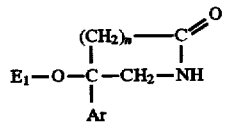

in which

Ar' and x are as defined for (I) and Y" is either Y' as defined for (I), or a precursor of Y', it being understood that if Y" contains a hydroxyl or an amino group, these groups can be protected;

or a group

in which

Ar' is as defined for (I);

or a group $$\begin{array}{c} Ar'\text{---}C\text{---}CH\text{---} \\ \|\quad\ | \\ O \end{array}$$

in which

Ar' is as defined for (I);

or a group $$Ar'\text{---}W_2\text{---}CH\text{---} \\ |$$

in which

Ar' and $W_2$ are as defined for (I);

or with a cyclic tertiary amine of the formula

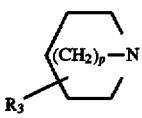 (Xb)

in which p and $R_3$ are as defined above for a compound of formula (I);

or with a cyclic secondary amine of the formula

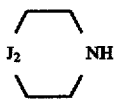 (Xc)

in which $J_2$ is as defined above for (I);

or with a cyclic secondary amine of the formula

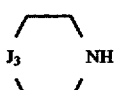 (Xd)

in which $J_3$ is as defined above for (I);

or with a cyclic secondary amine of the formula

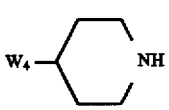 (Xe)

in which $W_4$ is as defined above for (I);

or with a cyclic secondary amine of the formula

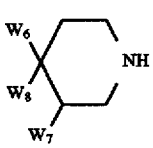 (Xf)

in which $W_6$, $W_7$ and $W_8$ are as defined above for (I);

or with a cyclic secondary amine of the formula:

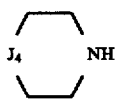 (Xg)

in which $J_4$ is as defined above for (I);

or with a compound of the formula

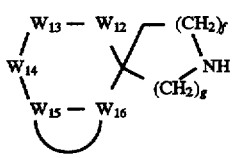 (Xh)

in which f, g, $W_{12}$, $W_{13}$, $W_{14}$, $W_{15}$ and $W_{16}$ are as defined above for (I); and 7)—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 6) to a salt thereof with a mineral or organic acid;

or, in the case where a cyclic tertiary amine of formula (Xb) has been used, isolating the product thus obtained in step 6) or optionally exchanging the sulfonate anion of the resulting quaternary salt with another pharmaceutically acceptable anion.

In steps 2) and 4), the protecting groups $E_1$ or $E_2$ are removed by conventional methods well known to those skilled in the art, for example by hydrolysis.

The substitution effected in step 3) is carried out at room temperature with a solution of the derivative Hal-$(CH_2)_m$—O—$E_2$ in an organic solvent such as dimethylformamide or tetrahydrofuran, and in the presence of a hydride such as, for example, sodium hydride.

Step 6) of method A consists in reacting the compound of formula (IX) with an amine of formula (Xa), (Xb), (Xc), (Xd), (Xe), (Xf), (Xg) or (Xh). The reaction is generally carried out in solution in an organic solvent such as, for example, dimethylformamide, at a temperature between about 20° and 80° C.

The compounds (I) obtained are isolated and purified by the usual methods such as, for example, chromatography or recrystallization.

Another preparative method according to the invention (method B) is suitable for preparing compounds of formula (I) in which simultaneously $R_1$ and $R_2$ together form a group —$(CH_2)_n$—CQ— where Q=$H_2$ and n=1, 2 or 3, or alternatively $R_1$ and $R_2$ are separate and are as defined for the compound (I), $W_1$ is an oxygen atom and B is B', i.e. one of the groups $B_2$, $B_3$, $B_4$, $B_5$, $B_6$, $B_7$ or $B_8$ as defined above for a compound of formula (I).

This method consists in:

1) eliminating the O-protecting group $E_1$ from a compound of the formula

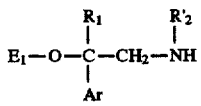 (XI)

in which $R_1$ and Ar are as defined above for a compound of formula (I), $R'_2$ is a hydrogen, a $(C_1-C_7)$-alkyl, an ω-$(C_1-C_4)$-alkoxy-$(C_2-C_4)$-alkylene, an ω-hydroxy-$(C_2-C_4)$-alkylene, an ω-$(C_1-C_4)$-alkylthio-$(C_2-C_4)$-alkylene, an ω-$(C_1-C_4)$-alkoxycarbonyl-$(C_2-C_4)$-alkylene, an ω-carboxy-$(C_2-C_4)$-alkylene, an ω-$(C_1-C_4)$-alkylcarbonyl-$(C_2-C_4)$-alkylene, an ω-$R_6R_7NCO$-$(C_2-C_4)$-alkylene or an ω-cyano-$(C_1-C_3)$-alkylene, or $R_1$ and $R'_2$ together form a group —$(CH_2)_n$—CQ— (n=1, 2 or 3 and Q=$H_2$), and $E_1$ is an O-protecting group, in particular the tetrahydropyran-2-yl group, by reaction with an acid;

2) protecting the amine group of the resulting compound of the formula

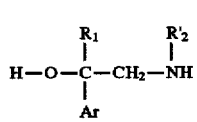 (XII)

for example by reaction with di-tert-butyl dicarbonate ($Boc_2O$) in a solvent such as dioxane, to give the compound of the formula

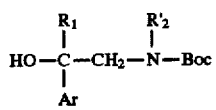
(XIII)

3) if appropriate, if R'$_2$ in the compound of formula (XI) is an ω-hydroxy-(C$_2$–C$_4$)-alkylene, protecting the amine group as indicated in step 2) and then protecting the hydroxyl or optionally converting the group R'$_2$ to R"$_2$, to give a compound of the formula

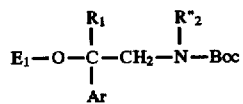
(XIV)

in which E$_1$, R$_1$ and Ar are as defined above and R"$_2$ is an ω-(C$_1$–C$_4$)-alkylcarbonyloxy-(C$_2$–C$_4$)-alkylene, an ω-benzoyloxy-(C$_2$–C$_4$)-alkylene, an ω-benzyloxy-(C$_2$–C$_4$)-alkylene, an ω-formyloxy-(C$_2$–C$_4$)-alkylene, an ω-R$_5$NHCOO—(C$_2$–C$_4$)-alkylene, an ω-R$_8$R$_9$N—(C$_2$–C$_4$)-alkylene, an ω-R$_{10}$CONR$_{11}$—(C$_2$–C$_4$)-alkylene, an ω-R$_{12}$OCONR$_{11}$—(C$_2$–C$_4$)-alkylene, an ω-R$_6$R$_7$NCONR$_{11}$—(C$_2$–C$_4$)-alkylene or an ω-R$_{13}$SO$_2$NR$_{11}$—(C$_2$–C$_4$)-alkylene, and then selectively eliminating the protecting group E$_2$ by acid hydrolysis to give the compound of the formula

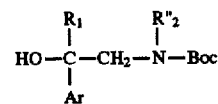
(XIIIbis)

4) treating the compound (XIII) or (XIIIbis) obtained in step 2) or in step 3), it being understood that if R'$_2$ is an ω-hydroxy-(C$_2$–C$_4$)-alkylene, the hydroxyl is protected, or if R"$_2$ is a group ω-R$_8$R$_9$N—(C$_2$–C$_4$)-alkylene in which R$_8$ is a hydrogen, the amine is protected, with a compound of formula (VI): Hal-(CH$_2$)$_m$—O—E$_2$, in which E$_2$ is an O-protecting group such as the tetrahydropyran-2-yl group, in order to form the compound of the formula

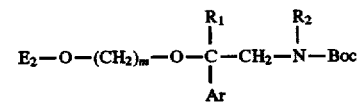
(XV)

in which E$_2$, m, Ar and R$_1$ are as defined above and R$_2$ is as defined for a compound of formula (I);

5) selectively eliminating the protecting group E$_2$, for example by reaction with pyridinium paratoluenesulfonate if E$_2$ is a tetrahydropyran-2-yl, to give a compound of the formula:

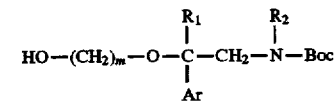
(XVI)

6) treating the compound (XVI), it being understood that if R$_2$ is an ω-hydroxy-(C$_2$–C$_4$)-alkylene, the hydroxyl is protected, or if R"$_2$ is a group ω-R$_8$R$_9$N—(C$_2$–C$_4$)-alkylene in which R$_8$ is a hydrogen, the amine is protected, with a compound of formula (XXIX) as defined above in method A, to give the sulfonate of the formula

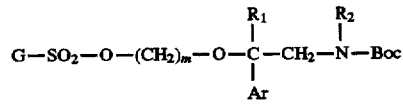
(XVII)

7) reacting the compound (XVII) with a compound of formula (Xa), (Xc), (Xd), (Xe), (Xf), (Xg) or (Xh) as defined above in method A, and then optionally converting Y" to Y', to give the compound of the formula

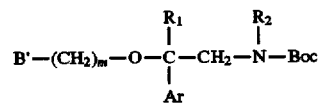
(XVIII)

in which B' is a group B$_2$, B$_3$, B$_4$, B$_5$, B$_6$, B$_7$ or B$_8$ as defined above for a compound of formula (I);

8) deprotecting the N-protecting group of the compound (XVIII) by treatment in a strong acid medium, for example HCl, to give the compound of the formula

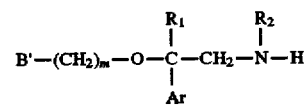
(XIX)

9) reacting the compound of formula (XIX) either with a halogenated derivative of the formula

Hal-CH$_2$—A—Z (III)

in which Hal is a halogen atom, preferably bromine, and A and Z are as defined above, if R$_1$ and R$_2$ are separate and if it is intended to prepare a compound of formula (I) in which T is —CH$_2$—;

or with a functional derivative of an acid of the formula

HO—CO—A—Z (IIIa)

in which A and Z are as defined above, if it is intended to prepare a compound of formula (I) in which T is —CO—;

or with a chloroformate of the formula

Cl—COO—A—Z (IIIb)

in which A and Z are as defined above, if it is intended to prepare a compound of formula (I) in which T is —COO—;

or with an isocyanate of the formula

O=C=N—A—Z (IIIc)

in which A and Z are as defined above, if it is intended to prepare a compound of formula (I) in which T is a group —CO—NR$_4$— in which R$_4$ is a hydrogen;

or with a carbamoyl chloride of the formula

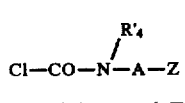
(IIId)

in which A and Z are as defined above and R'$_4$ is a (C$_1$–C$_4$)-alkyl group, if it is intended to prepare a compound of formula (I) in which T is —CO—NR$_4$— in which R$_4$ is a (C$_1$–C$_4$)-alkyl; and 10) after deprotection of the hydroxyl or amino groups, if appropriate, or optional conversion of Y" to Y', optionally converting the product obtained in step 9) to a salt thereof with a mineral or organic acid.

In a variant of method B, method C according to the invention is suitable for preparing compounds of formula (I) in which simultaneously $R_1$ and $R_2$ together form a group —$(CH_2)_n$—CQ— in which Q=$H_2$ and n=1, 2 or 3, or alternatively $R_1$ and $R_2$ are separate and are as defined for the compound (I), $W_1$ is an oxygen atom and B is as defined for a compound of formula (I). According to this method:

1') the protecting group $E_2$ and the N-protecting group of the compound (XV) obtained in step 4) of method B are eliminated simultaneously, it being understood that if $R_2$ is an ω-hydroxy-($C_2$-$C_4$)-alkylene in which the hydroxyl is protected, the latter is not affected under the operating conditions, or if $R_2$ is a group ω-$R_8R_9$N—($C_2$-$C_4$)-alkylene in which the amine is protected, the latter is not affected under the operating conditions, by treatment in a strong acid medium, for example with HCl, to give the compound of the formula

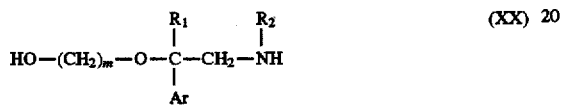
(XX)

in which m, Ar, $R_1$ and $R_2$ are as defined above for (I);

2') the compound (XX) is treated with one of the compounds (III), (IIIa), (IIIb), (IIIc) or (IIId) as defined above, to give the compound of the formula

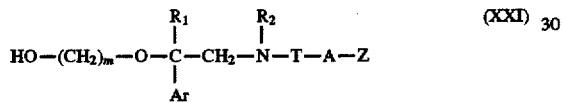
(XXI)

in which m, Ar, $R_1$, $R_2$, T, A and Z are as defined above;

3') the compound (XXI) is treated, it being understood that if $R_2$ is an ω-hydroxy-($C_2$-$C_4$)-alkylene, the hydroxyl is protected, or if $R_2$ is a group ω-$R_8R_9$N—($C_2$-$C_4$)-alkylene in which $R_8$ is a hydrogen, the amine is protected, with the compound of formula (XXIX) as defined above, to give the compound of the formula

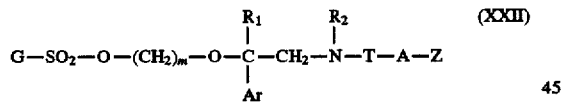
(XXII)

4') the compound (XXII) is reacted with one of the compounds (Xa), (Xb), (Xc), (Xd), (Xe), (Xf), (Xg) or (Xh) as defined above; and 5')—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', the product obtained in step 4') is optionally converted to a salt thereof with a mineral or organic acid;

or, in the case where a cyclic tertiary amine of formula (Xb) has been used and after deprotection of the hydroxyl or amino groups, the product thus obtained in step 4') is isolated or the sulfonate anion of the resulting quaternary salt is optionally exchanged with a pharmaceutically acceptable anion.

In another variant of method B (method C') and with the proviso that T is other than —CO—NH— or that —T—A— is other than —CO—$(CH_2)_r$—, 1") a compound of formula (XI) as defined above in method B is treated with one of the compounds of formula (III), (IIIa), (IIIb) or (IIId) as defined above, to give a compound of the formula

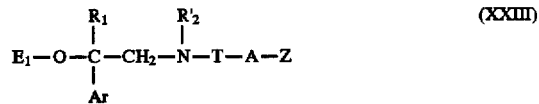
(XXIII)

in which $E_1$, Ar, $R_1$, $R'_2$, T, A and Z are as defined above;

2") if appropriate, if $R'_2$ is an ω-hydroxy-($C_2$-$C_4$)-alkylene, the hydroxyl is protected, or the group $R'_2$ is optionally converted to $R''_2$, to give a compound of the formula

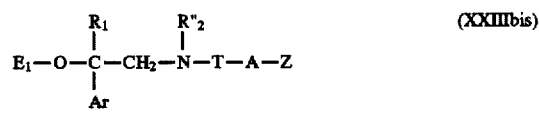
(XXIIIbis)

in which $E_1$, Ar, $R_1$, T, A and Z are as defined above and $R''_2$ is an ω-($C_1$-$C_4$)-alkylcarbonyloxy-($C_2$-$C_4$)-alkylene, an ω-benzoyloxy-($C_2$-$C_4$)-alkylene, an ω-benzyloxy-($C_2$-$C_4$)-alkylene, an ω-formyloxy-($C_2$-$C_4$)-alkylene, an ω-$R_5$NHCOO—($C_2$-$C_4$)-alkylene, an ω-$R_8R_9$N—($C_2$-$C_4$)-alkylene, an ω-$R_{10}$CONR$_{11}$—($C_2$-$C_4$)-alkylene, an ω-$R_{12}$OCONR$_{11}$—($C_2$-$C_4$)-alkylene, an ω-$R_6R_7$NCONR$_{11}$—($C_2$-$C_4$)-alkylene or an ω-$R_{13}$SO$_2$NR$_{11}$—($C_2$-$C_4$)-alkylene;

3") the protecting group $E_1$ is selectively eliminated from the compound (XXIII) or (XXIIIbis) by reaction with an acid in order to form the compound of the formula

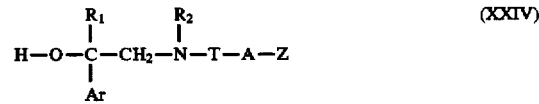
(XXIV)

4") the resulting compound (XXIV) is treated, it being understood that if $R_2$ is an ω-hydroxy-($C_2$-$C_4$)-alkylene, the hydroxyl is protected, or if $R_2$ is a group ω-$R_8R_9$N—($C_2$-$C_4$)-alkylene in which $R_8$ is a hydrogen, the amine is protected, with a compound of formula (VI): Hal-$(CH_2)_m$—O—$E_2$, in which $E_2$ is an O-protecting group such as the tetrahydropyran-2-yl group, to give the compound of the formula

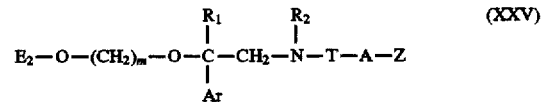
(XXV)

5") the protecting group $E_2$ is selectively eliminated by reaction with an acid to give the compound of the formula

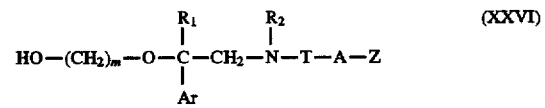
(XXVI)

6") the compound (XXVI) is treated, it being understood that if $R_2$ is an ω-hydroxy-($C_2$-$C_4$)-alkylene, the hydroxyl is protected, or if $R_2$ is an ω-$R_8R_9$N—($C_2$-$C_4$)-alkylene in which $R_8$ is hydrogen, the amine is protected, with the compound of formula (XXIX) as defined above, in order to form the compound of the formula

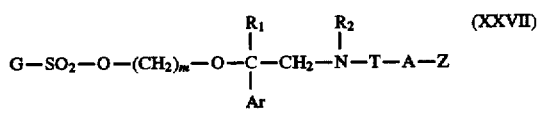

(XXVII)

7") the resulting compound (XXVII) is reacted with one of the compounds (Xa), (Xb), (Xc), (Xd), (Xe), (Xf), (Xg) or (Xh) as defined above; and 8")—either, in the case where a cyclic secondary amine of formula (Xa), (Xc), (Xd), (Xe), (Xf), (Xg) or (Xh) has been used and after deprotection of the hydroxyl or amino groups, if appropriate, or optional conversion of Y" to Y', the product obtained in step 7") is optionally converted to a salt thereof with a mineral or organic acid;

or, in the case where a cyclic tertiary amine of formula (Xb) has been used and after deprotection of the hydroxyl or amino group, if appropriate, the product thus obtained in step 7") is isolated or the sulfonate anion of the resulting quaternary salt is optionally exchanged with a pharmaceutically acceptable anion.

In step 9) of method B, in step 2') of method C or in step 1") of method C', the functional derivative of the acid (IIIa) used is the acid itself, appropriately activated for example with 1,3-dicyclohexylcarbodiimide or with benzotriazol-1-yloxytris(dimethylamino)phosphonium hexafluorophosphate (BOP), or alternatively one of the functional derivatives which react with amines, for example an anhydride, a mixed anhydride, the acid chloride or an activated ester such as the paranitrophenyl ester.

If a chloroformate of formula (IIIb) is used, the reaction is carried out in a solvent such as dichloromethane, at a temperature between 0° C. and room temperature and in the presence of a base such as triethylamine.

If an isocyanate of formula (IIIc) is used, the reaction is carried out in an inert solvent such as dichloromethane or benzene, overnight, at room temperature.

If a carbamoyl chloride of formula (IIId) is used, the reaction is carried out in a solvent such as toluene or 1,2-dichloroethane, at a temperature between 0° C. and 110° C. and in the presence of a base such as triethylamine.

Step 7) of method B, step 4') of method C or step 7") of method C', in which a compound (Xa), (Xb), (Xc), (Xd), (Xe), (Xf), (Xg) or (Xh) is reacted, is carried out as described above in method A.

Step 3) of method B or step 4") of method C', in which the compound (VI) is reacted, is carried out as described above in method A.

In step 3) of method B or in step 2") of method C', the resulting compound is subjected to a subsequent treatment, if appropriate, in order to prepare a compound of formula (XIV) or a compound of formula (XXIIIbis) by conversion of the group $R'_2$ to $R"_2$, or, if appropriate, if $R'_2$ is an ω-hydroxy-$(C_2$-$C_4)$-alkylene, the hydroxyl is protected.

Thus, if $R'_2$ is an ω-hydroxy-$(C_2$-$C_4)$-alkylene, an O-acylation reaction is carried out, if appropriate, by the methods known to those skilled in the art to give a compound of formula (XIV) or a compound of formula (XXIIIbis) in which $R"_2$ is an ω-$(C_1$-$C_4)$-alkylcarbonyloxy-$(C_2$-$C_4)$-alkylene or an ω-benzoyloxy-$(C_2$-$C_4)$-alkylene.

By reacting a compound in which $R'_2$ is an ω-hydroxy-$(C_2$-$C_4)$-alkylene with formic acid in acetic anhydride, a compound of formula (XIV) or a compound of formula (XXIIIbis) is prepared in which $R"_2$ is an ω-formyloxy-$(C_2$-$C_4)$-alkylene.

By reacting a compound in which $R'_2$ is an ω-hydroxy-$(C_2$-$C_4)$-alkylene with a benzyl halide by the conventional methods, a compound of formula (XIV) or a compound of formula (XXIIIbis) is prepared in which $R"_2$ is an ω-benzyloxy-$(C_2$-$C_4)$-alkylene.

By reacting a compound in which $R'_2$ is an ω-hydroxy-$(C_2$-$C_4)$-alkylene with an isocyanate of the formula $R_5$—N=C=O, a compound of formula (XIV) or a compound of formula (XXIIIbis) is prepared in which $R"_2$ is an ω-$R_5$NHCOO—$(C_2$-$C_4)$-alkylene.

To prepare a compound of formula (XIV) or a compound of formula (XXIIIbis) in which $R"_2$ is an ω-$R_{10}$CONR$_{11}$—$(C_2$-$C_4)$-alkylene in which $R_{11}$ is a hydrogen or a $(C_1$-$C_7)$-alkyl and $R_{10}$ is a hydrogen or, respectively, a $(C_1$-$C_7)$-alkyl, a vinyl, a phenyl, a benzyl, a pyridyl or a $(C_3$-$C_7)$-cycloalkyl which is optionally substituted, formic acid in acetic anhydride or, respectively, an appropriate anhydride of the formula $(R_{10}CO)_2$ or an appropriate acid chloride of the formula $R_{10}$COCl is reacted, in the presence of a base such as triethylamine, with a compound of formula (XIV) or a compound of formula (XXIIIbis) in which $R"_2$ is an ω-HNR$_{11}$—$(C_2$-$C_4)$-alkylene.

Likewise, by reaction with a chloroformate of the formula $R_{12}$OCOCl, the compounds of formula (XIV) or a compound of formula (XXIIIbis) are prepared in which $R"_2$ is a group ω-$R_{12}$OCONR$_{11}$—$(C_2$-$C_4)$-alkylene.

By reaction with an isocyanate of the formula $R_7$N=C=O, the compounds of formula (XIV) or the compounds of formula (XXIIIbis) are prepared in which $R"_2$ is an ω-$R_6R_7$NCONR$_{11}$—$(C_2$-$C_4)$-alkylene in which $R_6$ is a hydrogen.

By reaction with a carbamoyl chloride of the formula $R_6R_7$NCOCl, the compounds of formula (XIV) or the compounds of formula (XXIIIbis) are prepared in which $R"_2$ is an ω-$R_6R_7$NCONR$_{11}$—$(C_2$-$C_4)$-alkylene in which $R_6$ is a $(C_1$-$C_7)$-alkyl.

By reaction with a sulfonyl chloride of the formula $R_{13}$SO$_2$Cl, the compounds of formula (XIV) or the compounds of formula (XXIIIbis) are prepared in which $R"_2$ is an ω-$R_{13}$SO$_2$NR$_{11}$—$(C_2$-$C_4)$-alkylene.

A compound of formula (XIV) or a compound of formula (XXIIIbis) in which $R"_2$ is an ω-$R_8R_9$N—$(C_2$-$C_4)$-alkylene in which $R_8$=$R_9$=H is prepared from a compound of formula (XI) or a compound of formula (XXIII) in which $R'_2$ is an ω-hydroxy-$(C_2$-$C_4)$-alkylene by the method described in J. Med. Chem., 1989, 32, 391–396.

A compound of formula (XIV) or a compound of formula (XXIIIbis) in which $R"_2$ is an ω-$R_8R_9$N—$(C_2$-$C_4)$-alkylene in which $R_8$=$R_9$=H can also be prepared from a compound of formula (XI) or a compound of formula (XXIII) in which $R'_2$ is an ω-cyano-$(C_1$-$C_3)$-alkylene by reduction of the nitrile group using the methods known to those skilled in the art.

A compound of formula (XIV) or a compound of formula (XXIIIbis) in which $R"_2$ is an ω-$R_8R_9$N—$(C_2$-$C_4)$-alkylene can be prepared by following the different steps of the method described in SCHEME 1.

SCHEME 1

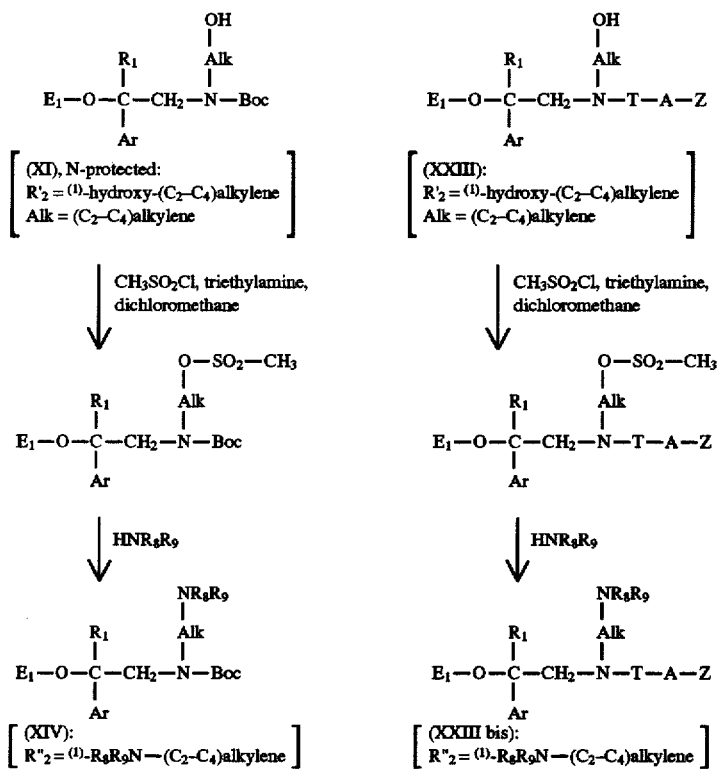

Another preparative method according to the invention (method D) is suitable for preparing compounds of formula (I) in which simultaneously $R_1$ and $R_2$ together form a group —$(CH_2)_n$—CQ— in which Q is oxygen, and $W_1$ is a group —NR— as defined for (I).

This method consists in:

1) treating a compound of the formula

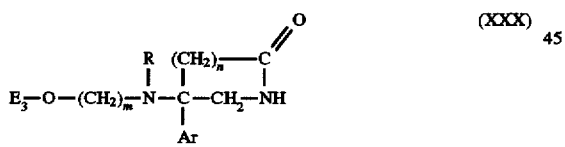 (XXX)

in which m, R and Ar are as defined above for a compound of formula (I) and $E_3$ is an O-protecting group, in particular the tetrahydropyran-2-yl group, with a halogenated derivative of the formula

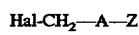 (III)

in which Hal is a halogen atom, preferably bromine, and A and Z are as defined above for a compound of formula (I), if it is intended to prepare a compound of formula (I) in which T is —$CH_2$—, in the presence of a base such as sodium hydride or potassium tert-butylate, in order to form the compound of the formula

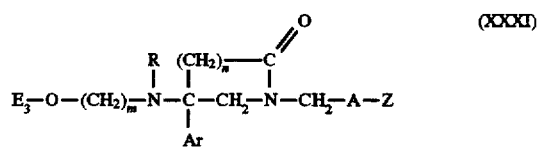 (XXXI)

2) eliminating the protecting group $E_3$ by reaction with an acid;

3) treating the resulting compound of the formula

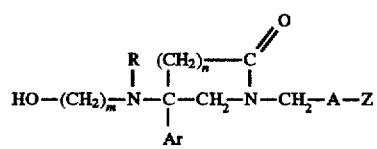 (XXXII)

with a compound of the formula

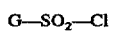 (XXIX)

in which G is a methyl, phenyl, tolyl or trifluoromethyl group;

4) reacting the resulting sulfonate of the formula

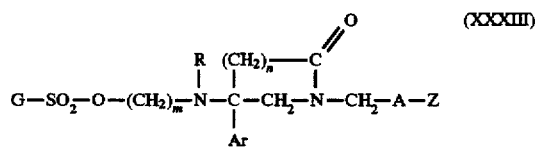 (XXXIII)

with one of the compounds of formula (Xa), (Xb), (Xc), (Xd), (Xe), (Xf), (Xg) or (Xh) as defined above in method A; and 5) —either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 4) to a salt thereof with a mineral or organic acid;

or, in the case where a cyclic tertiary amine of formula (Xb) has been used, isolating the product thus obtained in step 4) or optionally exchanging the sulfonate anion of the resulting quaternary salt with another pharmaceutically acceptable anion.

Another preparative method according to the invention (method E) is suitable for preparing compounds of formula (I) in which simultaneously $R_1$ and $R_2$ together form a group —$(CH_2)_n$—CQ— in which Q=$H_2$ and n=1, 2 or 3, or alternatively $R_1$ and $R_2$ are separate and are as defined for the compound (I), $W_1$ is a group —NR— and B is as defined for a compound of formula (I).

This method consists in:

1) treating a compound of the formula

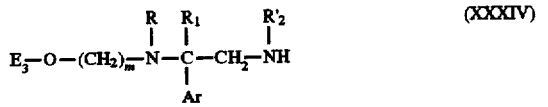

in which m, R, Ar and $R_1$ are as defined above for a compound of formula (I), $R'_2$ is a hydrogen, a $(C_1-C_7)$-alkyl, an $\omega$-$(C_1-C_4)$-alkoxy-$(C_2-C_4)$-alkylene, an $\omega$-hydroxy-$(C_2-C_4)$-alkylene, an $\omega$-$(C_1-C_4)$-alkylthio-$(C_2-C_4)$-alkylene, an $\omega$-$(C_1-C_4)$-alkoxycarbonyl-$(C_2-C_4)$-alkylene, an $\omega$-carboxy-$(C_2-C_4)$-alkylene, an $\omega$-$(C_1-C_4)$-alkylcarbonyl-$(C_2-C_4)$-alkylene, an $\omega$-$R_6R_7$NCO—$(C_2-C_4)$-alkylene or an $\omega$-cyano-$(C_1-C_3)$-alkylene, or alternatively $R_1$ and $R'_2$ together form a group —$(CH_2)_n$—CQ— (n=1, 2 or 3 and Q=$H_2$), and $E_3$ is an O-protecting group, in particular the tetrahydropyran-2-yl group, either with a halogenated derivative of the formula

in which Hal is a halogen atom, preferably bromine, and A and Z are as defined above for (I), if $R_1$ and $R_2$ are separate and if it is intended to prepare a compound of formula (I) in which T is —$CH_2$—;

or with a functional derivative of an acid of the formula

in which A and Z are as defined above, if it is intended to prepare a compound of formula (I) in which T is —CO—;

or with a chloroformate of the formula

in which A and Z are as defined above, if it is intended to prepare a compound of formula (I) in which T is —COO—;

or with an isocyanate of the formula

in which A and Z are as defined above, if it is intended to prepare a compound of formula (I) in which T is a group —CO—$NR_4$— in which $R_4$ is a hydrogen;

or with a carbamoyl chloride of the formula

in which A and Z are as defined above and $R'_4$ is a $(C_1-C_4)$-alkyl group, if it is intended to prepare a compound of formula (I) in which T is —CO—$NR_4$— in which $R_4$ is a $(C_1-C_4)$-alkyl, to give a compound of the formula

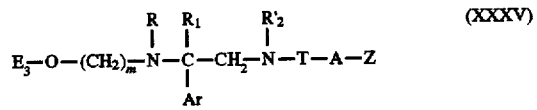

2) if appropriate, if $R'_2$ is an $\omega$-hydroxy-$(C_2-C_4)$-alkylene, protecting the hydroxyl, or optionally converting the group $R'_2$ to $R"_2$, to give a compound of the formula

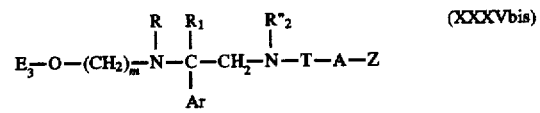

in which $E_3$, m, R, $R_1$, Ar, T, A and Z are as defined above and $R"_2$ is an $\omega$-$(C_1-C_4)$-alkylcarbonyloxy-$(C_2-C_4)$-alkylene, an $\omega$-benzoyloxy-$(C_2-C_4)$-alkylene, a $\omega$benzyloxy-$(C_2-C_4)$-alkylene, an $\omega$-formyloxy-$(C_2-C_4)$-alkylene, an $\omega$-$R_5$NHCOO—$(C_2-C_4)$-alkylene, an $\omega$-$R_8R_9$N—$(C_2-C_4)$-alkylene, an $\omega$-$R_{10}$CONR$_{11}$—$(C_2-C_4)$-alkylene, an $\omega$-$R_{12}$CONR$_{11}$—$(C_2-C_4)$-alkylene, an $\omega$-$R_6R_7$NCONR$_{11}$—$(C_2-C_4)$-alkylene or an $\omega$-$R_{13}$SO$_2$NR$_{11}$—$(C_2-C_4)$-alkylene;

3) selectively eliminating the protecting group $E_3$ from the compound (XXXV) or (XXXVbis) by reaction with an acid to give a compound of the formula

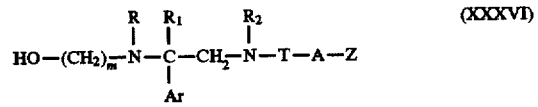

4) if appropriate, eliminating the protecting group $E_3$ from a compound of formula (XXXIV) by reaction with an acid to give a compound of the formula

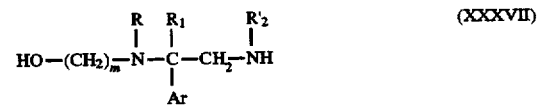

in which m, R, Ar, $R_1$ and $R'_2$ are as defined above, and then treating the compound (XXXVII) with one of the compounds (III), (IIIa), (IIIb), (IIIc) or (IIId) as defined above, to give the compound of the formula

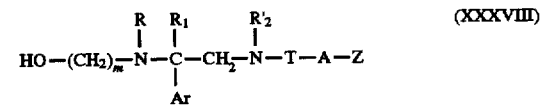

in which m, R, Ar, T, A, Z, $R_1$ and $R'_2$ are as defined above;

5) treating the compound (XXXVI) or (XXXVIII), it being understood that if $R_2$ or $R'_2$ is an $\omega$-hydroxy-$(C_2-C_4)$-alkylene, the hydroxyl is protected, or if $R_2$ is an ω-R₈R₉N—(C₂-C₄)-alkylene in which R₈ is hydrogen, the amine is protected, with a compound of formula (XXIX) as defined above in method D, to give a compound of the formula

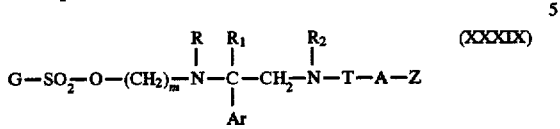

6) reacting the resulting sulfonate with one of the compounds (Xa), (Xb), (Xc), (Xd), (Xe), (Xf), (Xg) or (Xh) as defined above in method A; and 7) — either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 6) to a salt thereof with a mineral or organic acid;

or, in the case where a cyclic tertiary amine of formula (Xb) has been used, isolating the product thus obtained in step 6) or optionally exchanging the sulfonate anion of the resulting quaternary salt with another pharmaceutically acceptable anion.

In a variant of method E and if B is B', i.e. one of the groups $B_2$, $B_3$, $B_4$, $B_5$, $B_6$, $B_7$ or $B_8$ as defined for a compound of formula (I), 1') the O-protecting group $E_3$ is eliminated from the compound of formula (XXXIV) to give the compound of formula (XXXVII) as defined in step 4) of method E;

2') the amine group of the compound of formula (XXXVII) is protected by reaction for example with di-tert-butyl dicarbonate (Boc₂O) in a solvent such as dioxane to give a compound of the formula

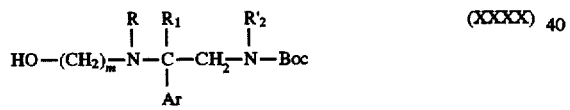

3') if appropriate, if R'₂ in the compound of formula (XXXIV) is an ω-hydroxy-(C₂-C₄)-alkylene, the amine group is protected as indicated in step 2') and then the hydroxyl is protected, or the group R'₂ is optionally converted to R"₂, to give a compound of the formula

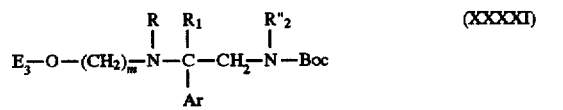

in which m, R, $E_3$, $R_1$ and Ar are as defined above and R"₂ is an ω-(C₁-C₄)-alkylcarbonyloxy-(C₂-C₄)-alkylene, an ω-benzoyloxy-(C₂-C₄)-alkylene, an ω-benzyloxy-(C₂-C₄)-alkylene, an ω-formyloxy-(C₂-C₄)-alkylene, an ω-R₅NHCOO—(C₂-C₄)-alkylene, an ω-R₈R₉N—(C₂-C₄)-alkylene, an ω-R₁₀CONR₁₁—(C₂-C₄)-alkylene, an ω-R₁₂OCONR₁₁—(C₂-C₄)-alkylene, an ω-R₆R₇NCONR₁₁—(C₂-C₄)-alkylene or an ω-R₁₃SO₂NR₁₁—(C₂-C₄)-alkylene, and the protecting group $E_3$ is then selectively eliminated by acid hydrolysis to give the compound of the formula

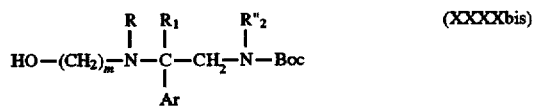

4') the compound (XXXX) or the compound (XXXXbis) is treated, it being understood that if R'₂ is an ω-hydroxy-(C₂-C₄)-alkylene, the hydroxyl is protected, or if R"₂ is a group ω-R₈R₉N—(C₂-C₄)-alkylene in which R₈ is a hydrogen, the amine is protected, with a compound of formula (XXIX) as defined above in method A, to give the sulfonate of the formula

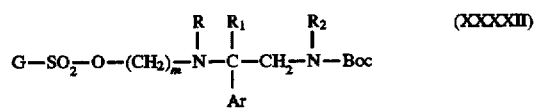

5') the compound (XXXXII) is reacted with a compound of formula (Xa), (Xc), (Xd), (Xe), (Xf), (Xg) or (Xh) as defined above in method A, and Y" is optionally converted to Y', to give the compound of the formula

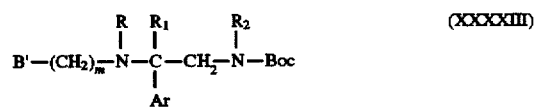

in which B' is a group $B_2$ $B_3$, $B_4$, $B_5$, $B_6$, $B_7$ or $B_8$ as defined above for a compound of formula (I);

6') the N-protecting group of the compound (XXXXIII) is deprotected by treatment in a strong acid medium, for example HCl, to give the compound of the formula

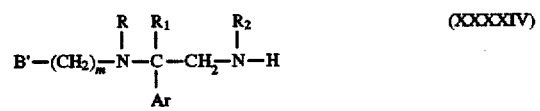

7') the compound of formula (XXXXIV) is reacted— either with a halogenated derivative of the formula

in which Hal is a halogen atom, preferably bromine, and A and Z are as defined above, if $R_1$ and $R_2$ are separate and if it is intended to prepare a compound of formula (I) in which T is —CH₂—;

or with a functional derivative of an acid of the formula

in which A and Z are as defined above, if it is intended to prepare a compound of formula (I) in which T is —CO—;

or with a chloroformate of the formula

in which A and Z are as defined above, if it is intended to prepare a compound of formula (I) in which T is —COO—;

or with an isocyanate of the formula

in which A and Z are as defined above, if it is intended to prepare a compound of formula (I) in which T is a group —CO—NR$_4$— in which R$_4$ is a hydrogen; or with a carbamoyl chloride of the formula

(IIId)

in which A and Z are as defined above and R'$_4$ is a (C$_1$–C$_4$)-alkyl group, if it is intended to prepare a compound of formula (I) in which T is —CO—NR$_4$— in which R$_4$ is a (C$_1$–C$_4$)-alkyl; and 8') after deprotection of the hydroxyl or amino groups, if appropriate, or optional conversion of Y" to Y', the product obtained in step 7') is optionally converted to a salt thereof with a mineral or organic acid.

In step 2) of method D, step 3) or 4) of method E or step 1') or 3') of the variant of method E, the protecting group E$_3$ is eliminated by conventional methods. If E$_3$ is a tetrahydropyran-2-yl group, deprotection is effected by acid hydrolysis using hydrochloric acid in a solvent such as ether, methanol or a mixture of these solvents, or using pyridinium p-toluenesulfonate in a solvent such as methanol, or else using an Amberlyst® resin in a solvent such as methanol.

In step 3) of method D, step 5) of method E or step 4') of the variant of method E, the reaction with a sulfonyl chloride of formula (XXIX) is carried out in the presence of a base such as triethylamine, in an inert solvent such as dichloromethane, benzene or toluene, and at a temperature between −20° C. and room temperature.

In step 1) of method E or step 7') of the variant of method E, the reaction with a compound (III), (IIIa), (IIIb), (IIIc) or (IIId) is carried out as described above in method A, B or C.

In step 2) of method E or step 3') of the variant of method E, the conversion of the substituent R'$_2$ to R"$_2$ is effected as described above in method B or C.

In step 4) of method D, step 6) of method E or step 5') of the variant of method E, the reaction with a compound of formula (Xa), (Xb), (Xc), (Xd), (Xe), (Xf), (Xg) or (Xh) is carried out in an inert solvent such as N,N-dimethylformamide or acetonitrile, at a temperature between 20° C. and 90° C. and in the presence or absence of a base. If a base is used, it is selected from organic bases such as triethylamine, N,N-diisopropylethylamine or N-methylmorpholine, or from alkali metal carbonates or bicarbonates such as potassium carbonate, sodium carbonate or sodium bicarbonate.

In the course of any one of the steps of methods A, B, C, C', D or E for the preparation of the compounds of formula (I), and more particularly when using compounds of formula (Xc), (Xd), (Xe), (Xf), (Xg) or (Xh), it may be necessary and/or desirable to protect the reactive or sensitive functional groups, such as the amine, hydroxyl, thiol or carboxyl groups, present on any one of the molecules in question. This protection can be effected by using the conventional protecting groups such as those described in Protective Groups in Organic Chemistry, J. F. W. McOmie, published by Plenum Press, 1973, and in Protective Groups in Organic Synthesis, T. W. Greene and P. G. M. Wutts, published by John Wiley and Sons, 1991. The elimination of the protecting groups can be effected in a convenient subsequent step by using the methods which are known to those skilled in the art and do not affect the rest of the molecule in question.

The O-protecting groups which may be used to give a compound of formula (I) in which R$_2$ is an ω-hydroxy-(C$_2$–C$_4$)-alkylene and/or Y' is a hydroxyl are the conventional O-protecting groups well known to those skilled in the art, such as, for example, tetrahydropyran-2-yl, acetyl or benzoyl.

The N-protecting groups which may be used to give a compound of formula (I) in which Y' is an amino are the conventional N-protecting groups well known to those skilled in the art, such as, for example, the trityl, methoxytrityl, tert-butoxycarbonyl or benzyloxycarbonyl group.

The appropriate O-protecting and/or N-protecting groups are chosen according to whether it is desired to obtain a totally or partially deprotected compound of formula (I) in the final step of the method.

In particular, if the O-protecting group used is an acetyl group or a benzoyl group, the compound of formula (I) obtained represents the final product in which R$_2$ is an ω-acetoxy-(C$_2$–C$_4$)-alkylene and/or Y' is an acetoxy, or R$_2$ is an ω-benzoyloxy-(C$_2$–C$_4$)-alkylene.

The resulting compounds of formula (I) are:

either isolated in the form of the free base or a salt, by the conventional techniques, if B is B$_2$, B$_3$, B$_4$, B$_5$, B$_6$, B$_7$ or B$_8$, or, if B is B$_1$, the product of formula (I) is isolated or the anion of the quaternary salt obtained is optionally exchanged with another pharmaceutically acceptable anion.

If the compound of formula (I) in which B is B$_2$, B$_3$, B$_4$, B$_5$, B$_6$, B$_7$ or B$_8$ is obtained in the form of the free base, salification is effected by treatment with the chosen acid in an organic solvent. Treatment of the free base, dissolved for example in an alcohol such as isopropanol or in an ether such as diethyl ether, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, oxalate, maleate, fumarate, naphthalene-2-sulfonate and benzenesulfonate, for example, are prepared in this way.

At the end of the reaction, the compounds of formula (I) in which B is B$_2$, B$_3$, B$_4$, B$_5$, B$_6$, B$_7$ or B$_8$ can be isolated in the form of one of their salts, for example the hydrochloride or the oxalate; in this case, if necessary, the free base can be prepared by the neutralization of said salt with a mineral or organic base such as sodium hydroxide or triethylamine, or with an alkali metal carbonate or bicarbonate such as sodium or potassium carbonate or bicarbonate.

The sulfonate anion GSO$_3^\ominus$ originating from the reaction between the tertiary amine of formula (Xb) and the compound of formula (IX), (XXII), (XXVII), (XXXIII) or (XXXIX) can be exchanged, in situ or after isolation of the compound of formula (I) in which B is a group B$_1$ in which X$^\ominus$ is the ion GSO$_3^\ominus$, with another anion X$^\ominus$ by the conventional methods, for example by exchange in solution with saturated sodium chloride solution or with hydrochloric acid solution if X$^\ominus$ is a chloride anion, or by exchange of the anion through elution of the compound (I) on an ion exchange resin, for example Amberlite IRA 68® or Duolite A 375®.

The compound of formula (II) is prepared according to Scheme 2 below:

SCHEME 2

Preparation of the intermediates of formula II:

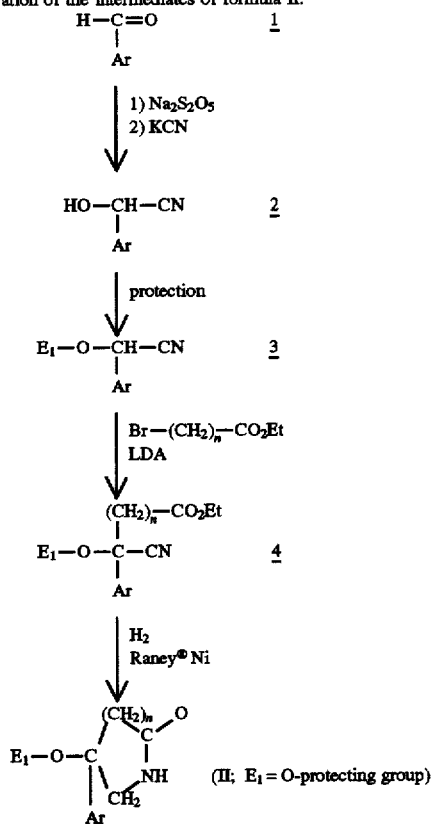

(II; $E_1$ = O-protecting group)

The hydroxyl group of the cyanohydrin 2 is then protected by reaction with 3,4-dihydro-2H-pyran.

The O-protected compound 3 is then substituted by the group —$(CH_2)_n$—COOEt by reaction with an ethyl bromoalkylcarboxylate, in which the alkyl is $C_1$-$C_3$, after having been treated with lithium diisopropylamide (LDA).

The resulting compound 4 is then hydrogenated in the presence of Raney® nickel to give the compound of formula (II) ($E_1$=—THP; Q=O).

The operating conditions of each of the above steps are conventional and are well known to those skilled in the art. For further details, reference may be made for example to Chem. Ber., 1975, 108, 3475–3482.

The starting compounds of formula (XI) in which $R_1$ and $R'_2$ together form a group —$(CH_2)_n$—CQ— in which n=1, 2 or 3 and Q=$H_2$ are obtained by reduction of the compounds of formula (II) by known methods such as reaction with a reducing agent like lithium aluminum hydride, for example, in a solvent such as diethyl ether, toluene or tetrahydrofuran, at a temperature between room temperature and 60° C.

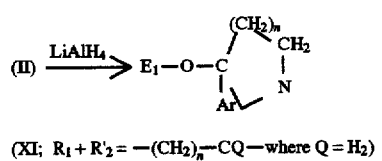

(XI; $R_1$ + $R'_2$ = —$(CH_2)_n$—CQ—where Q = $H_2$)

A compound of formula (XI) in which $R_1$ and $R'_2$ together form a group —$(CH_2)_n$—CQ— in which Q=$H_2$ and n=1 or 2 can also be prepared according to SCHEME 3.

SCHEME 3

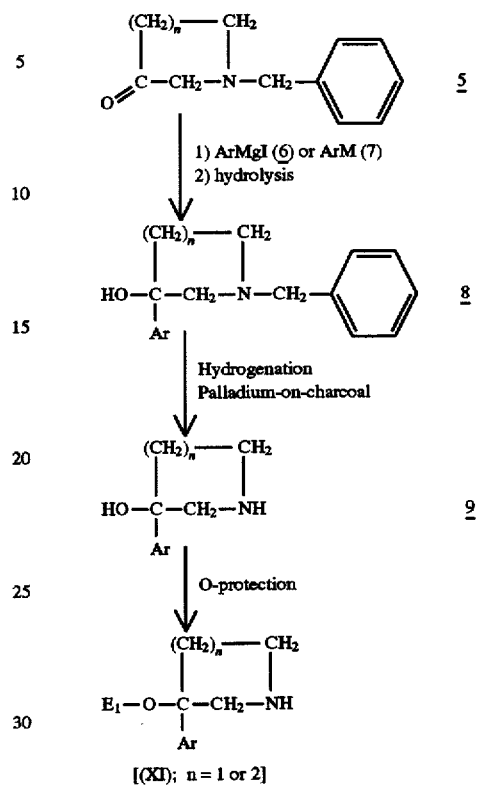

[(XI); n = 1 or 2]

A compound 5, in which n=1 or 2, is reacted with an organomagnesium iodide 6 or an organometallic compound 7, in which M is a reactive metal such as lithium, under anhydrous conditions, to give a compound 8 after hydrolysis of the intermediate obtained. The compound 8 is then N-deprotected and the resulting compound 9 is O-protected to give the expected compound of formula (XI).

The starting compounds of formula (XI) in which $R_1$ and $R'_2$ are separate and are as defined above are prepared from the nitriles of the formula

(XXVIII)

in which $E_1$, Ar and $R_1$ are as defined above, by reduction, followed, if appropriate, by substitution of the primary amine obtained.

The reduction of the nitriles of formula (XXVIII) is effected by hydrogenation in an alcohol such as ethanol, in the presence of a catalyst such as, for example, Raney® nickel, to give the primary amine of the formula

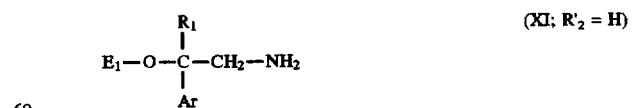

(XI; $R'_2$ = H)

after isolation by the conventional methods.

To prepare a compound of formula (XI) in which $R'_2$ is a methyl group, the amine (XI; $R'_2$=H) is treated with ethyl chloroformate or di-tert-butyl dicarbonate, in the presence of a base such as triethylamine, to give the corresponding carbamates. The carbonyl groups are then reduced by the usual methods such as reaction with a reducing agent like, for example, a metal hydride such as lithium aluminum hydride, or with a boron hydride such as borane dimethylsulfide. The reduction is effected in a solvent such as diethyl ether, toluene or tetrahydrofuran, at a temperature between room temperature and 60° C. The resulting amine of the formula

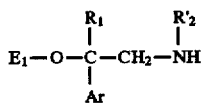  (XI; R'₂ = —CH₃)

is isolated by the usual methods.

The compound of formula (XI) in which R'₂ is a $C_2$–$C_7$-alkyl is prepared by replacing the ethyl chloroformate with a $C_2$–$C_7$-alkanoic acid chloride and reducing the carbonyl group of the resulting N-acylated derivative.

To prepare a compound of formula (XI) in which R'₂ is an ω-hydroxy-($C_2$–$C_4$)-alkylene group, the amine (XI; R'₂=H) is treated with ethyloxalyl chloride, ethyl hemimalonate or ethyl hemisuccinate, for example, to give the corresponding N-acylated derivatives. The carbonyl groups are then reduced by the usual methods.

In particular, the reaction of glycolic acid with the amine (XI; R'₂=H), in the presence of BOP and triethylamine, can be used to give the corresponding N-acylated derivative, which, after reduction of the carbonyl group, affords a compound of formula (XI) in which R'₂ is a 2-hydroxyethyl group.

If the ω-hydroxy-($C_2$–$C_4$)-alkylene group constitutes the group $R_2$ of the final compound of formula (I), it is necessary to protect the hydroxyl group. This protection step can be effected in conventional manner using an O-protecting group which will not be hydrolyzed when the group $E_1$ or $E_2$ is deprotected.

To prepare a compound of formula (XI) in which R'₂ is a group ω-($C_1$–$C_4$)-alkoxy-($C_2$–$C_4$)-alkylene, the amine (XI; R'₂=H) is reacted with an ω-($C_1$–$C_4$)-alkoxy-($C_2$–$C_4$)-alkanoic acid in the presence of BOP and a base such as triethylamine, and the carbonyl group of the N-acylated derivative obtained as an intermediate is then reduced.

To prepare a compound of formula (XI) in which R'₂ is an ω-($C_1$–$C_4$)-alkoxycarbonyl-($C_2$–$C_4$)-alkylene, the amine (XI; R'₂=H) is reacted with a ($C_1$–$C_4$)-alkyl ω-halogeno-($C_2$–$C_4$)-alkylenecarboxylate such as, for example, ethyl 3-bromopropionate, ethyl 4-bromobutyrate or ethyl 5-bromovalerate.

Hydrolysis of the compounds of formula (XI) in which R'₂ is an ω-($C_1$–$C_4$)-alkoxycarbonyl-($C_2$–$C_4$)-alkylene by the conventional methods gives the compounds of formula (XI) in which R'₂ is an ω-carboxy-($C_2$–$C_4$)-alkylene.

To prepare a compound of formula (XI) in which R'₂ is an ω-($C_1$–$C_4$)-alkylthio-($C_2$–$C_4$)-alkylene, the amine (XI; R'₂=H) is reacted with an ω-halogeno-($C_2$–$C_4$)-alkylene-($C_1$–$C_4$)-thioalkyl such as, for example, 2-chloro-1-methylthioethane.

A compound of formula (XI) in which R'₂ is an ω-$R_6R_7$NCO—($C_2$–$C_4$)-alkylene is obtained by reacting a compound of formula (XI) in which R'₂ is an ω-carboxy-($C_2$–$C_4$)-alkylene with a compound of formula NHR₆R₇ by the conventional methods of peptide coupling.

To prepare a compound of formula (XI) in which R'₂ is an ω-cyano-($C_1$–$C_3$)-alkylene, a compound of formula (XI) in which R'₂=H is reacted with chloroacetonitrile, 3-chloropropionitrile or 4-chlorobutyronitrile by the conventional methods of alkylation.

To prepare a compound of formula (XI) in which R'₂ is an ω-($C_1$–$C_4$)-alkylcarbonyl-($C_2$–$C_4$)-alkylene, the amine (XI; R'₂=H) is reacted with an ω-halogeno-($C_2$–$C_4$)-alkylenecarbonyl-($C_1$–$C_4$)-alkyl such as, for example, 4-chlorobutan-2-one, by the conventional methods of alkylation.

The nitriles of formula (XXVIII) are prepared from the nitriles of formula 3 in SCHEME 2 above by alkylation, if appropriate, using conventional methods well known to those skilled in the art.

The compound of formula (XXX) is prepared according to SCHEME 4 below.

SCHEME 4

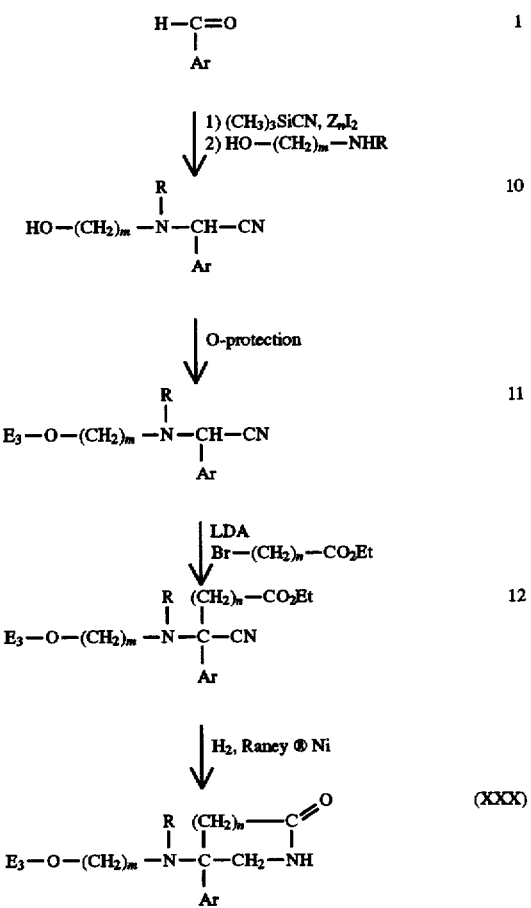

An α-aminonitrile compound 10 is prepared from an aldehyde 1 by the method described in Tetrahedron Letters, 1984, 25 (41), 4583–4586, using an amine of the formula HO—(CH₂)ₘ—NHR, in which m and R are as defined for (I).

The hydroxyl group of the compound 10 is then protected by reaction with 3,4-dihydro-2H-pyran, for example. The resulting compound 11 is then substituted by the group —(CH₂)ₙ—COOEt by reaction with an ethyl bromoalkylcarboxylate, in which the alkyl is $C_1$–$C_3$, after having been treated with lithium diisopropylamide (LDA). The resulting compound 12 is hydrogenated in the presence of Raney® nickel to give the expected compound of formula (XXX).

The starting compounds of formula (XXXIV) in which $R_1$ and R'₂ together form a group —(CH₂)ₙ—CQ— in which n=1, 2 or 3 and Q=H₂ are prepared by reduction of the compounds of formula (XXX) by known methods such as reaction with a reducing agent like lithium aluminum hydride, for example, in a solvent such as diethyl ether, toluene or tetrahydrofuran, at a temperature between room temperature and 60° C.

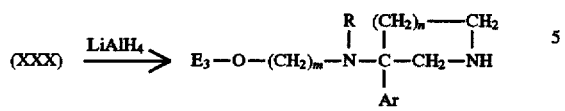

[(XXXIV); $R_1 + R'_2 = -(CH_2)_n-CQ-$ where $Q = H_2$]

A compound of formula (XXXIV) in which $R_1$ and $R'_2$ together form a group $-(CH_2)_n-CQ-$ in which n=1, 2 or 3 and $Q=H_2$ can also be prepared according to SCHEME 5.

SCHEME 5

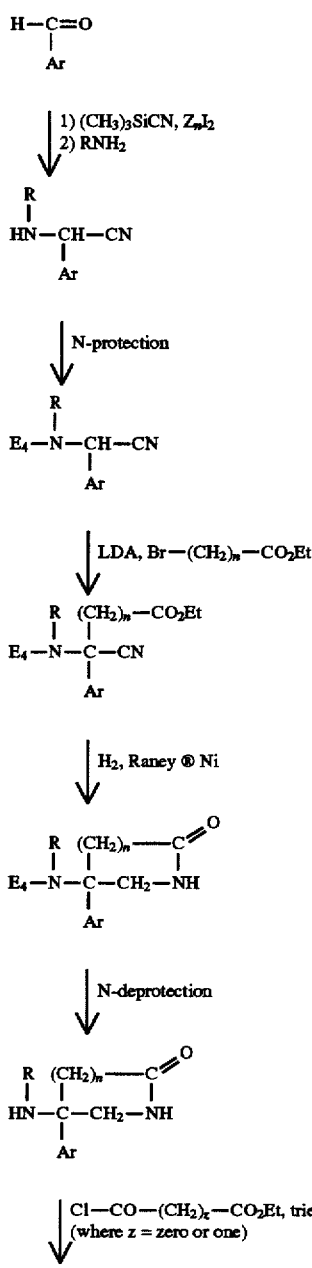

-continued
SCHEME 5

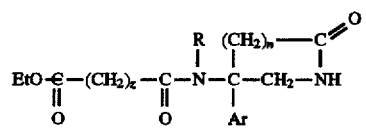

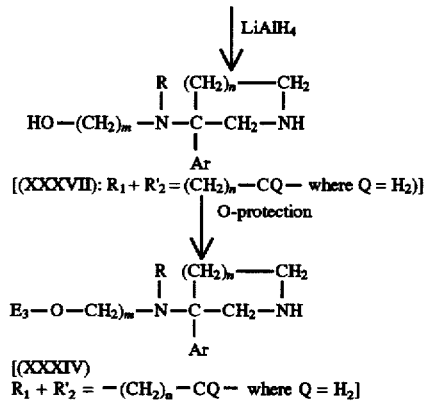

[(XXXIV)
$R_1 + R'_2 = -(CH_2)_n-CQ-$ where $Q = H_2$]

An α-aminonitrile compound 13 is prepared from an aldehyde 1 by the method described in Tetrahedron Letters, 1984, 25 (41), 4583–4586, using an amine of the formula $RNH_2$, in which R is as defined for (I).

The amino group of the compound 13 is then protected with an N-protecting group $E_4$, such as tert-butoxycarbonyl (Boc), by the methods known to those skilled in the art.

The resulting compound 14 is treated with a strong base, such as lithium diisopropylamide (LDA), in order to form a carbanion; this is reacted with a compound of the formula $Br-(CH_2)_n-CO_2Et$, in which n is as defined for (I), to give the compound 15. In particular, if n=2, reaction of the compound of formula 14 with ethyl acrylate, in the presence of a base such as 1,8-diazabicyclo[5.4.0]undec-7-ene (DBU), can be used to give the compound 15 in which n=2.

The compound 15 is then hydrogenated in the presence of Raney® nickel to give the compound 16.

The N-protecting group is eliminated to give the compound 17. If $E_4$ is a tert-butoxycarbonyl, for example, deprotection is effected by acid hydrolysis. The compound 17 is reacted with a compound of the formula $Cl-CO-(CH_2)_z-CO_2Et$ (i.e. ethyloxalyl chloride if z=0 or ethylmalonyl chloride if z=1), in the presence of a base such as triethylamine, to give the compound 18.

The carbonyl groups of the compound 18 are reduced by reaction with a reducing agent such as lithium aluminum hydride to give the expected compound of formula (XXXIV).

The starting compounds of formula (XXXIV) in which $R_1$ and $R'_2$ are separate and are as defined above are prepared according to SCHEME 6.

SCHEME 6

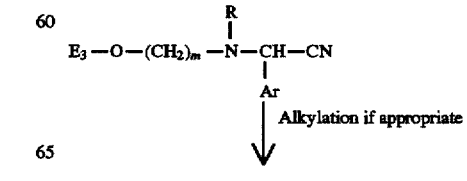

-continued
SCHEME 6

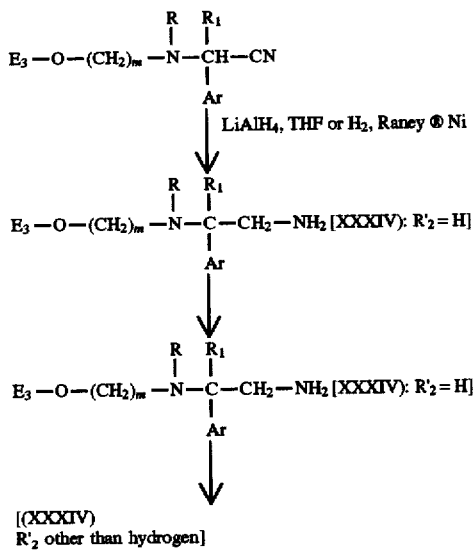

[(XXXIV)
R'₂ other than hydrogen]

The nitriles 19 are prepared from the nitriles of formula 11 in SCHEME 4 above by alkylation, if appropriate, using conventional methods, in order to introduce the substituent $R_1=(C_1-C_4)$-alkyl, it being understood that if R=H, the amine is protected.

The reduction of the nitriles 19 is effected either by reaction with a reducing agent such as lithium aluminum hydride by the conventional methods, or by hydrogenation in the presence of a catalyst such as, for example, Raney® nickel. This gives a compound of formula (XXXIV) in which R'₂=H.

If appropriate, the primary amine is substituted in order to introduce a substituent R'₂ other than hydrogen by the methods described above for a compound of formula (XI).

The piperidines of formula (Xa) are known or are prepared by known methods such as those described in EP-A-0428434, EP-A-0474561, EP-A-0512901 and EP-A-0515240.

The piperidines of formula (Xa) can also be prepared by methods well known to those skilled in the art, such as those described in the following publications:

J. Heterocyclic Chem., 1986, 23, 73–75
J. Chem. Soc., 1950, 1469
J. Chem. Soc., 1945, 917
J. Pharm. Sci., 1972, 61, 1316–1317
J. Org. Chem., 1957, 22, 1484–1489
Chem. Ber., 1975, 108, 3475–3482.

The compounds of formula (Xa) are generally prepared in a form protected on the piperidine nitrogen; the actual compounds of formula (Xa) are obtained after a deprotection step.

For example, if in a piperidine of formula (Xa) Ar' is a pyrid-2-yl group, Y" is hydroxyl and x is zero, 2-bromopyridine is reacted with N-benzylpiperid-4-one in a solvent, in the presence of butyllithium, in order to prepare N-benzyl-4-hydroxy-4-(pyrid-2-yl)piperidine, and 4-hydroxy-4-(pyrid-2-yl)piperidine is then obtained by deprotection in a basic medium.

The compounds of formula (Xa) in which Y" is a hydroxyl and which carry a protecting group on the piperidine nitrogen can undergo a Ritter reaction with acetonitrile in order to prepare the compounds of formula (Xa) in which Y" is an acetamido.

The compounds of formula (Xa) in which Y" is an amino are then prepared by hydrolysis in an acid medium. If appropriate, the amino group can be substituted by a group $R'_4=(C_1-C_4)$-alkyl.

The compounds of formula (Xa) in which Y" is the group $R_{14}CONR_4$— are prepared by reaction with a functional derivative of an acid $R_{14}COOH$.

The compounds of formula (Xa) in which Y" is the group —NR₄COOR₂₀ are prepared by reaction with a chloroformate ClCOOR₂₀. The compounds of formula (Xa) in which Y" is the group —NR₄SO₂R₂₁ are prepared by reaction with a sulfonyl chloride ClSO₂R₂₁. The compounds of formula (Xa) in which Y" is the group —NR₄CONR₂₂R₂₃ in which R₂₂=H are prepared by reaction with an isocyanate R₂₃N=C=O. The compounds of formula (Xa) in which Y" is the group —NR₄CONR₂₂R₂₃ are prepared by reaction with a carbamoyl chloride R₂₂R₂₃NCOCl.

A compound of formula (Xa) in which Y" is a group —NR₄CONR₂₂R₂₃ can also be obtained by reacting a compound HNR₂₂R₂₃ with a compound of formula (Xa) in which Y" is a group —NR₄COOR₂₀ in which R₂₀=phenyl.

It is self-evident that the reactions affording the compounds of formula (Xa) in which Y" is —NHR₄, —NR₄COOR₂₀, —NR₄SO₂R₂₁ or —NR₄CONR₂₂R₂₃ can be directly applied to the preparation of the compounds (Xa) in which Y" is —(CH₂)_qNHR₄, —(CH₂)_qNR₄COOR₂₀, —(CH₂)_qNR₄SO₂R₂₁ or —(CH₂)_qNR₄CONR₂₂R₂₃ in which q is one or two.

A compound of formula (Xa) in which Y" is a group —NR₁₆R₁₇ in which R₁₆ and R₁₇, together with the nitrogen atom to which they are bonded, form a heterocycle is prepared by applying or adapting Bruylants' reaction (Bull. Soc. Chim. Belges, 1924, 33, 467, and Tetrahedron Letters, 1988, 29 (52), 6827–6830).

A compound of formula (Xa) in which Y" is a group —CH₂—NR₁₈R₁₉ in which R₁₈ and R₁₉ are each hydrogen is prepared by reducing a compound of formula (Xa) in which Y" is a cyano. This reduction is effected by the methods well known to those skilled in the art.

A compound of formula (Xa) in which Y" is a group —CH₂—CH₂—NR₁₈R₁₉ in which R₁₈ and R₁₉ are each a hydrogen is prepared from a compound of formula (Xa) in which Y" is a group —CH₂—CH₂—OH by applying or adapting the method described in J. Med. Chem., 1989, 32, 391–396.

A compound of formula (Xa) in which Y" is a group —NR₁₆R₁₇ in which R₁₆ is a hydrogen and R₁₇ is a $(C_1-C_7)$-alkyl or, respectively, a $(C_3-C_7)$-cycloalkylmethyl or a benzyl can be prepared by reducing a compound of formula (Xa) in which Y" is a group —(CH₂)_q—NR₄COR₁₄ in which q is zero, R₄ is hydrogen and R₁₄ is a hydrogen, a $(C_1-C_6)$-alkyl or, respectively, a $(C_3-C_7)$-cycloalkyl or a phenyl. The reaction is carried out by means of a reducing agent such as lithium aluminum hydride, in a solvent such as tetrahydrofuran, at the reflux temperature of the solvent.

An identical reaction can be used to prepare the compounds of formula (Xa) in which Y" is a group —NR₁₆R₁₇ in which R₁₆ is a $(C_1-C_4)$-alkyl and R₁₇ is a $(C_1-C_7)$-alkyl or, respectively, a $(C_3-C_7)$-cycloalkylmethyl or a benzyl from a compound of formula (Xa) in which Y" is a group —(CH₂)_q—NR₄COR₁₄ in which q is zero, R₄ is a $(C_1-C_4)$-alkyl and R₁₄ is a hydrogen, a $(C_1-C_6)$-alkyl or, respectively, a $(C_3-C_7)$-cycloalkyl or a phenyl. The compounds of formula (Xa) in which Y" is a group —NR₁₆R₁₇ in which R₁₆ is a $(C_5-C_7)$-alkyl can be prepared in the same manner.

The compounds of formula (Xa) in which Y" is a group —CH₂—NR₁₈R₁₉ or, respectively, —CH₂CH₂NR₁₈R₁₉ in which $R_{18}$ is a hydrogen or a $(C_1-C_4)$-alkyl and $R_{19}$ is a $(C_1-C_7)$-alkyl, a $(C_3-C_7)$-cycloalkylmethyl or a benzyl can be prepared in the same manner from a compound of formula (Xa) in which Y" is a group —$(CH_2)_q$—$NR_4COR_{14}$ in which q is respectively 1 or 2, $R_4$ is a hydrogen or a $(C_1-C_4)$-alkyl and $R_{14}$ is a hydrogen, a $(C_1-C_6)$-alkyl, a $(C_3-C_7)$-cycloalkyl or a phenyl. The compounds of formula (Xa) in which Y" is a group —$CH_2NR_{18}R_{19}$ or —$CH_2CH_2NR_{18}R_{19}$ in which $R_{18}$ is a $(C_5-C_7)$-alkyl can be prepared in the same manner.

A compound of formula (Xa) in which Y" is a group —$(CH_2)_q$—$NR_4COR_{14}$ in which $R_4$ and $R_{14}$ together are a group —$(CH_2)_3$— or —$(CH_2)_4$— is prepared by applying or adapting the method described in J. Med. Chem., 1985, 20 28, 46–50.

A compound of formula (Xa) in which Y" is a group —$(CH_2)_q$—OH in which q is respectively one or two is prepared by reducing a compound of formula (Xa) in which Y" is a methoxycarbonyl or, respectively, a methoxycarbonylmethyl by the method described in Chem. Ber., 1975, 108, 3475–3482.

The compounds of formula (Xa) in which Y" is a group $R_{15}COO$—$(CH_2)_q$— are obtained by reacting an acid chloride $R_{15}COCl$ with the compounds of formula (Xa) in which Y" is a group —$(CH_2)_q$—OH; reaction with formic acid gives the compounds of formula (Xa) in which Y" is a group $R_{15}COO$—$(CH_2)_q$— in which $R_{15}$=H.

The compounds of formula (Xa) in which Y" is a group $(C_1-C_7)$-alkyl-NHCOO—$(CH_2)_q$— are obtained by reacting a carbamoyl chloride $(C_1-C_7)$-alkyl-NHCOCl with the compounds of formula (Xa) in which Y" is a group —$(CH_2)_q$—OH.

A compound of formula (Xa) in which Y" is a carboxyl can be prepared by hydrolyzing a compound of formula (Xa) in which Y" is a cyano by the methods known to those skilled in the art.

A compound of formula (Xa) in which Y" is a carboxymethyl can be prepared by the method described in Chem. Ber., 1975, 108, 3475–3482.

A compound of formula (Xa) in which Y" is a $(C_1-C_7)$-alkoxycarbonyl or, respectively, a $(C_1-C_7)$-alkoxycarbonylmethyl can be prepared from a compound of formula (Xa) in which Y" is a carboxyl or, respectively, a carboxymethyl by an esterification reaction using the methods well known to those skilled in the art.

A compound of formula (Xa) in which $J'_1$ is a group

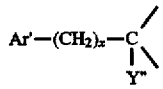

in which Ar' is an optionally substituted phenyl radical, x is one and Y" is a $(C_1-C_7)$-alkoxycarbonyl is prepared by reacting a protected 4-$(C_1-C_7)$-alkoxycarbonylpiperidine with an optionally substituted benzyl halide in the presence of a base such as sodium hydride, potassium tert-butylate or sodium diisopropylamide, in a solvent such as tetrahydrofuran, N,N-dimethylformamide or dimethyl sulfoxide, at a temperature between −78° C. and room temperature. The expected compound of formula (Xa) is obtained after a deprotection step.

A compound of formula (Xa) in which Y" is a group —$CONR_{22}R_{23}$ or, respectively, a group —$CH_2CONR_{22}R_{23}$ is prepared by reacting a compound of formula (Xa) in which Y" is a carboxyl or, respectively, a carboxymethyl with a compound of the formula $HNR_{22}R_{23}$ by the methods well known to those skilled in the art.

The amines of formula (Xb) are commercially available or are described in the literature, such as those mentioned below:

1-azabicyclo[2.2.1]heptane prepared according to Gassman et al., J. Am. Chem. Soc., 1968, (90), 5, 1355–6.

1-azabicyclo[2.2.2]octane, or quinuclidine.

4-phenyl-1-azabicyclo[2.2.2]octane, or 4-phenylquinuclidine, prepared according to T. Perrine, J. Org. Chem., 1957, 22, 1484–1489.

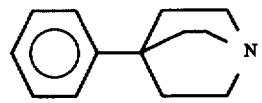

The piperazines of formula (Xc) are known or are prepared by known methods such as those described in EP-A-0474561.

The piperidines of formula (Xd) are known or are prepared by known methods such as those described in WO 94/10146.

The piperidines of formula (Xe) are known or are prepared by known methods such as those described in EP-A-0625509.

The piperidines of formula (Xf) are known or are prepared by known methods such as those described in EP-A-0630887.

The piperidines of formula (Xg) are known or are prepared by known methods such as those described in WO 94/26735.

The compounds of formula (Xh) are known or are prepared by known methods such as those described in WO 94/29309.

The compounds of formulae XXX, XXXI, XXXII, XXXIII, XXXIV, XXXV, XXXVbis, XXXVI, XXXVII, XXXVIII, XXXIX, XXXX, XXXXbis, XXXXI, XXXXII, XXXXIII and XXXXIV are useful for the preparation of the compounds according to the invention of formula (I) in which $W_1$ is a group —NR—. These compounds are characterized by the following general formula:

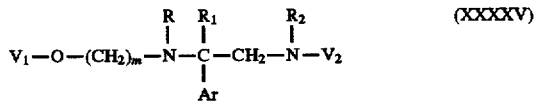

in which m, R, $R_1$ and $R_2$ are as defined for (I), $V_1$ is hydrogen; an O-protecting group, in particular the tetrahydropyran-2-yl group; or a group G—$SO_2$, in which G is a methyl, phenyl, tolyl or trifluoromethyl group; and $V_2$ is hydrogen; an N-protecting group such as tert-butoxycarbonyl; or a group T—A—Z, in which T, A and Z are as defined for (I).

These compounds are novel and form a further subject of the present invention.

Resolution of the racemic mixtures (I) makes it possible to isolate the enantiomers (I∗) of the formula

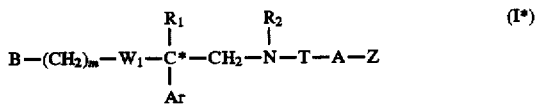 (I∗)

in which:

"∗" denotes that the carbon atom carrying this label has the determined (+) or (−) absolute configuration; and $W_1$, B, m, Ar, $R_1$, $R_2$, T, A and Z are as defined above for the compounds of formula (I), or a salt thereof, where appropriate, with mineral or organic acids.

Said salts are prepared as indicated above for the salts of the derivatives of formula (I).

The enantiomers of formula (I∗) are novel products which form part of the invention.

It is also possible to resolve racemic mixtures—of the products of the formula

 (II')

in which Ar and n are as defined for (I), which are obtained by deprotecting the group $E_1$ of the products of formula (II), in order to prepare the enantiomers (I∗) of the products of formula (I) in which $R_1$ and $R_2$ together form a group —$(CH_2)_n$—CQ— in which Q=O and n=1, 2 or 3, and $W_1$ is an oxygen atom,—or of the products of the formula

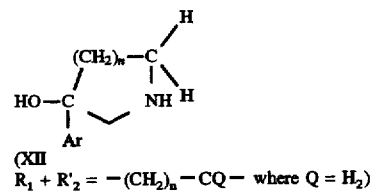

(XII)
$R_1 + R'_2 = -(CH_2)_n-CQ-$ where Q = $H_2$)

in which Ar and n are as defined for (I), in order to prepare the enantiomers (I∗) of the products of formula (I) in which $R_1$ and $R_2$ together form a group —$(CH_2)_n$—CQ— in which Q=$H_2$ and n=1, 2 or 3, and $W_1$ is an oxygen atom,—or of the products of the formula

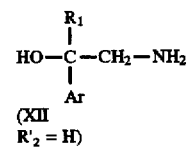

(XII
$R'_2$ = H)

in which Ar and $R_1$ are as defined for (I), in order to prepare the enantiomers (I∗) of the products of formula (I) in which $R_1$ and $R_2$ are separate and $W_1$ is an oxygen atom,—or of the products of the formula

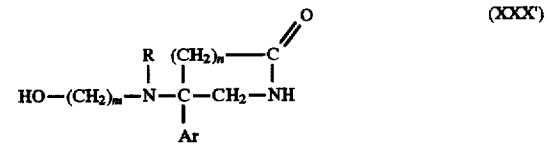 (XXX')

in which m, n, R and Ar are as defined for (I), which are obtained by deprotection of the group $E_3$ of the products of formula (XXX), in order to prepare the enantiomers (I∗) of the compounds of formula (I) in which $R_1$ and $R_2$ together form a group —$(CH_2)_n$—CQ— in which Q=O and n=1, 2 or 3, and $W_1$ is a group —NR—,—or of the products of the formula

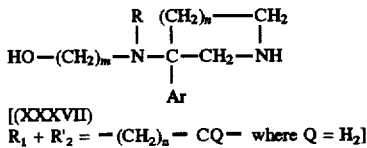

[(XXXVII)
$R_1 + R'_2 = -(CH_2)_n-CQ-$ where Q = $H_2$]

in which m, R, Ar and n are as defined for (I), in order to prepare the enantiomers (I∗) of the compounds of formula (I) in which $R_1$ and $R_2$ together form a group —$(CH_2)_n$—CQ— in which Q=$H_2$ and n=1, 2 or 3, and $W_1$ is a group —NR—,—or of the products of the formula

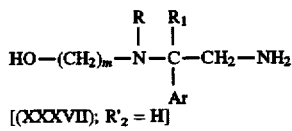

[(XXXVII); $R'_2$ = H]

in which m, R, Ar and $R_1$ are as defined for (I), in order to prepare the enantiomers (I∗) of the compounds of formula (I) in which $R_1$ and $R_2$ are separate and $W_1$ is a group —NR—.

Resolution of the racemates is effected on the intermediates (II'), using known methods, by forming an ester with optically active acids, for example with (+)- or (−)-mandelic acid, or on the intermediates (XII) [$R_1+R'_2=-(CH_2)_n-$CQ— where Q=$H_2$, or $R'_2$=H], or on the intermediates (XXX'), or on the intermediates (XXXVII) [$R_1+R'_2=-(CH_2)_n-$CQ— where Q=$H_2$, or $R'_2$=H] by forming a salt with optically active acids, for example with (+)- or (−)-tartaric acid. The diastereoisomers are then separated by the conventional methods such as crystallization or chromatography, the optically pure enantiomers then being obtained by hydrolysis.

The compounds of formula (I) above also include those in which one or more hydrogen or carbon atoms have been replaced with their radioactive isotope, for example tritium, carbon-14 or iodine-125. Such labeled compounds are useful in research, metabolic or pharmacokinetic studies and in biochemical tests as receptor ligand.

The affinity of the compounds for the tachykinin receptors was evaluated in vitro by several biochemical tests using radioligands:

1) The binding of [$^{125}$I]BH-SP (substance P labeled with iodine-125 using Bolton-Hunter's reagent) to the $NK_1$ receptors of the rat cortex, the guinea-pig ileum and human lymphoblasts.

2) The binding of [$^{125}$I]His-NKa to the $NK_2$ receptors of the rat duodenum.

3) The binding of [$^{125}$I]His[MePhe$^7$]$NK_B$ to the $NK_3$ receptors of the rat cerebral cortex, the guinea-pig cerebral cortex and the gerbil cerebral cortex, and to the human $NK_3$ cloned receptors expressed by CHO cells (Buell et al., FEBS Letters, 1992, 299, 90–95).

The tests were performed according to X. Emonds-Alt et al. (Eur. J. Pharmacol., 1993, 250, 403–413).

The compounds according to the invention have an affinity for the abovementioned tachykinin receptors with an inhibition constant Ki below $10^{-8}$M.

In particular, the compounds of the present invention are active principles of pharmaceutical compositions, the toxicity of which is compatible with their use as drugs.

The compounds of the present invention are generally administered in dosage unit. Said dosage units are preferably formulated as pharmaceutical compositions in which the active principle is mixed with a pharmaceutical excipient.

Thus, according to another of its features, the present invention relates to pharmaceutical compositions in which a compound of formula (I) or a pharmaceutically acceptable salt thereof is present as the active principle.

The compositions according to the invention advantageously contain from 0.5 to 1000 mg of active principle, preferably from 2.5 to 250 mg of active principle.

The compounds of formula (I) above and the pharmaceutically acceptable salts thereof can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, inhalational, subcutaneous, intramuscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

When a solid composition in the form of tablets is prepared, the main active principle is mixed with a pharmaceutical vehicle such as silica, gelatin, starch, lactose, magnesium stearate, talc, gum arabic or the like. The tablets can be coated with sucrose, various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester, and incorporating the mixture obtained into soft or hard gelatin capsules.

A preparation in the form of a syrup or elixir can contain the active principle together with a sweetener, which is preferably calorie-free, methylparaben and propylparaben as antiseptic, a flavoring and an appropriate color.

The water-dispersible granules or powders can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol or butylene glycol.

Administration by inhalation is effected using an aerosol which contains for example sorbitan trioleate or oleic acid, as well as trichlorofluoromethane, dichlorofluoromethane, dichlorotetrafluoroethane or any other biologically compatible propellant gas; it is also possible to use a system containing the active principle in powder form, by itself or associated with an excipient.

The active principle can also be formulated as microcapsules, with one or more carriers or additives if appropriate.

The abovementioned compositions can also contain other active products such as, for example, bronchodilators, antitussives or antihistamines.

According to another of its features, the present invention relates to the use of the products of formula (I) for the preparation of drugs intended for the treatment of physiological disorders associated with an excess of tachykinins and all neurokinin-dependent pathological conditions of the respiratory, gastrointestinal, urinary, immune, cardiovascular and central nervous systems, as well as pain and migraine.

Non-limiting examples are:

acute and chronic pain associated for example with migraine, with pains experienced by cancer and angina patients, and with chronic inflammatory processes such as osteoarthritis and rheumatoid arthritis, inflammations such as obstructive chronic respiratory diseases, asthma, allergies, rhinitis, coughs, bronchitis, hypersensitivity, for example to pollen and mites, arthritis, rheumatoid diseases, osteoarthritis, psoriasis, ulcerative colitis, Crohn's disease, inflammation of the intestines (irritable colon), prostatitis, nervous bladder, cystitis, urethritis and nephritis, diseases of the immune system associated with suppression or stimulation of the functions of the immune cells, for example rheumatoid arthritis, psoriasis, Crohn's disease, diabetes and lupus, diseases of the central nervous system of the neuropsychiatric or neurological type, such as anxiety, depression, psychosis, schizophrenia, mania, dementia, epilepsy, Parkinson's disease, Alzheimer's disease, drug dependence, Down's syndrome and Huntington's chorea, as well as neurodegenerative diseases, diseases of the gastrointestinal system, such as nausea, vomiting, irritable colon, gastric and duodenal ulcers, diarrhea and hypersecretions, and diseases of the cardiovascular system, such as hypertension, the vascular aspects of migraine, edema, thrombosis, angina pectoris and vascular spasms.

The present invention also includes a method of treating said complaints at the doses indicated above.

The following abbreviations are used in the Preparations and in the Examples:

EtOH: ethanol
MeOH: methanol
Ether: diethyl ether
Iso ether: diisopropyl ether
DMF: dimethylformamide
DCM: dichloromethane
THF: tetrahydrofuran
AcOEt: ethyl acetate
$Na_2CO_3$: sodium carbonate
NaCl: sodium chloride
$MgSO_4$: magnesium sulfate
NaOH: sodium hydroxide
HCl: hydrochloric acid
Hydrochloric ether: saturated solution of hydrochloric acid in ether
KCN: potassium cyanide
$NH_4Cl$: ammonium chloride
M.p.: melting point
RT: room temperature Silica H: silica gel 60H, marketed by Merck (DARMSTADT)
NMR: nuclear magnetic resonance.

PREPARATIONS

Preparation 1

5-(3,4-Dichlorophenyl)-5-(tetrahydropyran-2-yloxy) piperidin-2-one a) 2-(3,4-Dichlorophenyl)-2-hydroxyacetonitrile 25 g of 3,4-dichlorobenzaldehyde are added to a solution of 32.5 g of $Na_2S_2O_5$ in 100 ml of water and the mixture is heated at 40°–45° C. for 1 hour. After one night at room temperature, the reaction mixture is cooled and a solution of 19.5 g of KCN in 40 ml of water is added slowly. After stirring for 30 minutes at RT, extraction is carried out with ether and the extract is washed with water, dried over $MgSO_4$ and evaporated under vacuum to give 29 g of the expected product, which is used as such in the next step.

b) 2-(3,4-Dichlorophenyl)-2-(tetrahydropyran-2-yloxy) acetonitrile 0.1 g of paratoluenesulfonic acid is added to a solution of 29 g of the compound obtained in the previous step in 250 ml of DCM. The mixture is cooled to 0° C. and a solution of 15.6 ml of 3,4-dihydro-2H-pyran in 50 ml of DCM is added dropwise. The reaction mixture is stirred for 2 hours, the temperature being allowed to rise to RT, and is then left to stand overnight in a refrigerator. The organic phase is washed with saturated NaCl solution, dried over $MgSO_4$ and evaporated under vacuum to give 31.9 g of the expected product after crystallization from pentane. M.p.=61° C.

c) Ethyl 4-(3,4-dichlorophenyl)-4-cyano-4-(tetrahydropyran-2-yloxy)butanoate

A solution of 12.6 g of the compound obtained in the previous step in 160 ml of ether is cooled to −70° C., 32 ml of a 1.5M solution of lithium diisopropylamide in hexane are added and the mixture is stirred for 15 minutes at −70° C. A solution of 8.8 g of ethyl 3-bromopropionate in ether is then added, the temperature is allowed to rise to 0° C. and the reaction mixture is stirred for 3 hours. It is poured into saturated $NH_4Cl$ solution and the organic phase is decanted, washed with water, dried over $MgSO_4$ and evaporated under vacuum to give 15 g of the expected product, which is used as such in the next step.

d) 5-(3,4-Dichlorophenyl)-5-(tetrahydropyran-2-yloxy) piperdin-2-one

A mixture of 15 g of the compound obtained in the previous step and 150 ml of absolute EtOH is hydrogenated at RT and under atmospheric pressure, in the presence of Raney® nickel. It is filtered on Célite® and the filtrate is concentrated under vacuum. The residue is chromatographed on silica gel using DCM and then a gradient of a DCM/MeOH mixture (up to 97/3; v/v) as the eluent to give 5 g of the expected product after crystallization from an iso ether/pentane mixture. M.p.=170° C.

Preparation 2

3-(Tetrahydropyran-2-yloxy)-3-(3,4-dichlorophenyl) piperidine

A solution of 2 g of the compound obtained according to Preparation 1 above in 20 ml of THF is added to a suspension of 480 mg of lithium aluminum hydride in 10 ml of THF. The reaction mixture is heated at a temperature of 40°–50° C. for 30 minutes and the mixture is then allowed to return to room temperature. It is hydrolyzed with 2.5 ml of water, the reaction mixture is then filtered and the filtrate is concentrated under vacuum to give 1.9 g of the expected product, which is used as such in EXAMPLE 3.

Preparation 3

N-Methyl-2-(3,4-dichlorophenyl)-2-(tetrahydropyran-2-yloxy)ethanamine a) 2-(3,4-Dichlorophenyl)-2-(tetrahydropyran-2-yloxy) ethanamine 100 ml of concentrated aqueous ammonia and some Raney® nickel are added to a solution of 31.9 g of the compound obtained in Preparation 1, step b), in 400 ml of absolute EtOH. The mixture is hydrogenated at RT and under atmospheric pressure. After the theoretical volume of hydrogen has been absorbed, the catalyst is filtered off on Célite® and the filtrate is concentrated under vacuum. The residue is taken up with ether, washed with water and with saturated NaCl solution, dried over $MgSO_4$ and concentrated under vacuum to give 30.6 g of an oil of the expected product, which is used as such in the next step.

b) N-Ethoxycarbonyl-2-(3,4-dichlorophenyl)-2-(tetrahydropyran-2-yloxy)ethanamine 16.3 ml of triethylamine are added to a solution of 30.6 g of the compound obtained above in 300 ml of DCM, the mixture is then cooled to 0° C. and 11 ml of ethyl chloroformate are added dropwise. After stirring for 15 minutes, the reaction mixture is washed twice with water and the organic phase is dried over $MgSO_4$ and concentrated under vacuum. The residue is chromatographed on silica using heptane and then a heptane/AcOEt mixture (70/30; v/v) as the eluent to give 31.5 g of an oil of the expected product, which is used as such in the next step.

c) N-Methyl-2-(3,4-dichlorophenyl)-2-(tetrahydropyran-2-yloxy)ethanamine

A solution of 31.5 g of the compound obtained above in 300 ml of THF is added slowly to a suspension of 7 g of lithium aluminum hydride in 100 ml of THF and the mixture is refluxed for 1 hour. After cooling, it is hydrolyzed by the addition of 30 ml of water, the mineral salts are filtered off and the filtrate is concentrated under vacuum to give 26.5 g of an oil of the expected product, which is used as such in EXAMPLE 8.

Preparation 4

N-Methyl-2-(3,4-dichlorophenyl)-2-[N'-methyl-N'-[2-(tetrahydropyran-2-yloxy)ethyl]amino]ethylamine A) 2-(3,4-Dichlorophenyl)-2-[N-(2-hydroxyethyl)-N-methylamino]acetonitrile A mixture of 10 g of 3,4-dichlorobenzaldehyde and 9.5 ml of cyanotrimethylsilane is cooled in an ice bath, 0.01 g of zinc iodide is added and the mixture is stirred for 15 minutes at RT. A solution of 4.5 g of 2-(methylamino)ethanol in 50 ml of MeOH is then added and the reaction mixture is heated at 60° C. for 2 hours. After one night at RT, it is concentrated under vacuum, the residue is extracted with ether and the organic phase is washed with water, dried over $MgSO_4$ and filtered. The filtrate is acidified to pH 1 by the addition of a saturated solution of hydrochloric acid in ether, acetone is added and the mixture is stirred until crystallization occurs. This gives 15 g of the expected product after wringing of the crystals formed. M.p.=130° C.

B) 2-(3,4-Dichlorophenyl)-2-[N-methyl-N-[2-(tetrahydropyran-2-yloxy)ethyl]amino]acetonitrile 0.1 g of p-toluenesulfonic acid monohydrate and then 6.5 ml of 3,4-dihydro-2H-pyran are added to a solution of 15 g of the compound obtained in the previous step in 200 ml of DCM and the reaction mixture is stirred overnight at RT. It is washed with water and with 1N NaOH solution, the organic phase is dried over MgSO$_4$ and the solvent is evaporated off under vacuum. The residue is chromatographed on silica using heptane and then a gradient of a heptane/AcOEt mixture (up to 85/15; v/v) as the eluent to give 14.1 g of the expected product, which is used as such.

C) 2-(3,4-Dichlorophenyl)-2-[N'-methyl-N'-[2-(tetrahydropyran-2-yloxy)ethyl]amino]ethylamine A solution of 12.7 g of the compound obtained in the previous step in 100 ml of THF is added at RT to a suspension of 4.5 g of lithium aluminum hydride in 50 ml of THF and the mixture is stirred for 24 hours at RT. A further 2 g of lithium aluminum hydride are then added and the reaction mixture is stirred for 2 hours at RT. It is hydrolyzed by the addition of 32 ml of water and then 3 ml of concentrated NaOH solution, the mineral salts are filtered off and the filtrate is concentrated under vacuum to give 13 g of the expected product, which is used as such.

D) N-(tert-Butoxycarbonyl)-2-(3,4-dichlorophenyl)-2-[N'-methyl-N'-[2-(tetrahydropyran-2-yloxy)ethyl]amino] ethylamine 9.8 g of di-tert-butyl dicarbonate are added to a solution of 13 g of the compound obtained in the previous step in 200 ml of THF and the reaction mixture is stirred for 1 hour at RT. It is concentrated under vacuum and the residue is chromatographed on silica using heptane and then a gradient of a heptane/AcOEt mixture (up to 60/40; v/v) as the eluent to give 8.7 g of the expected product, which is used as such.

E) N-Methyl-2-(3,4-dichlorophenyl)-2-[N'-methyl-N'-[2-(tetrahydropyran-2-yloxy)ethyl]amino]ethylamine A solution of 8.7 g of the compound obtained in the previous step in 50 ml of THF is added at RT to a suspension of 1.9 g of lithium aluminum hydride in 20 ml of THF and the mixture is refluxed for two hours 30 minutes. It is hydrolyzed by the addition of 8 ml of water, the mineral salts are filtered off and the filtrate is concentrated under vacuum to give 6.1 g of the expected product, which is used as such.

Preparation 5

4-Benzylquinuclidine

A) 1,4-Dibenzyl-4-cyanopiperidine

A solution of 15 g of 4-cyanopiperidine in 250 ml of THF is cooled to −50° C., 190 ml of a 1.5M solution of lithium diisopropylamide in cyclohexane are added dropwise and the mixture is stirred for 30 minutes at −50° C. 34 ml of benzyl bromide are then added and the mixture is stirred for 3 hours after the temperature has been allowed to rise to RT. The reaction mixture is poured into an ice/concentrated HCl mixture, ether is added and the precipitate formed is filtered off and washed with water. The precipitate is taken up with water, rendered alkaline to pH 12 by the addition of concentrated NaOH solution, and extracted with ether, the organic phase is dried over MgSO$_4$ and the solvent is evaporated off to give 31.7 g of the expected product after crystallization from pentane. M.p.=92° C.

B) 4-Acetyl-1,4-dibenzylpiperidine hydrochloride 55 ml of a 1.6M solution of methyllithium in ether are added to a solution of 20 g of the compound obtained in the previous step in 400 ml of ether and the reaction mixture is stirred for 3 hours at RT. It is poured into iced water, the organic phase is decanted and dried over MgSO$_4$ and the solvent is evaporated off under vacuum. The residue is taken up with 400 ml of water and 40 ml of concentrated HCl and refluxed for 2 hours. After one night at RT, the crystals formed are wrung, washed with acetone and then with ether and dried to give 17.6 g of the expected product. M.p.=246° C.

C) 1,4-Dibenzyl-4-(2-bromoacetyl)piperidine hydrobromide 1.6 ml of bromine are added to a solution of 10 g of the compound obtained in the previous step in 40 ml of acetic acid and the mixture is stirred overnight at RT. 50 ml of ether are added to the reaction mixture and the crystals formed are wrung and washed with an acetone/ether mixture and then with ether to give 12.5 g of the expected product. M.p.=205° C.

D) 1,4-Dibenzyl-3-oxoquinuclidinium bromide

Concentrated NaOH solution is added to a suspension of 12.5 g of the compound obtained in the previous step in water until the pH is 12, the mixture is extracted with ether, the organic phase is dried over MgSO$_4$ and the solvent is evaporated off under vacuum. The residue is taken up with acetone and stirred for 2 hours at RT. The precipitate is wrung, washed with ether and dried to give 10.08 g of the expected product. M.p.=234° C.

E) 4-Benzyl-3-oxoquinuclidine

A mixture of 10 g of the compound obtained in the previous step, 1 g of 10% palladium-on-charcoal and 200 ml of MeOH is hydrogenated at RT and at atmospheric pressure. The catalyst is filtered off and the filtrate is evaporated under vacuum. The residue is taken up with ether and the precipitate formed is wrung. The precipitate is dissolved in water and rendered alkaline to pH 12 by the addition of concentrated NaOH solution, and the precipitate formed is filtered off, washed with water and dried to give 5 g of the expected product. M.p.=111° C.

F) 4-Benzylquinuclidine

A mixture of 5 g of the compound obtained in the previous step, 2.5 g of hydrazine hydrate, 4.3 g of KOH and 25 ml of ethylene glycol is heated at 175° C. for 2 hours. The reaction mixture is poured into iced water and extracted twice with ether, the organic phase is washed with water and dried over MgSO$_4$ and the solvent is evaporated off under vacuum. The residue is dissolved in acetone and acidified to pH 1 by the addition of hydrochloric ether, and the precipitate formed is wrung and washed with an acetone/ether mixture (50/50; v/v) and then with ether. The precipitate is dissolved in water, rendered alkaline to pH 12 by the addition of concentrated NaOH solution, and extracted with ether, the extract is dried over MgSO$_4$ and the solvent is evaporated off under vacuum to give 1.8 g of the expected product. M.p.= 48° C.

EXAMPLE 1

4-Acetamido-4-phenyl-1-[2-[1-benzyl-5-(3,4-dichlorophenyl)-2-oxopiperid-5-yloxy]ethyl] piperidine hydrochloride hemihydrate A) 5-(Tetrahydropyran-2-yloxy)-5-(3,4-dichlorophenyl)-1-benzylpiperidin-2-one 1.0 g of the compound obtained in Preparation 1 is dissolved in 15 ml of THF, and 0.36 g of potassium tert-butylate is added. The reaction mixture is stirred for 30 minutes at room temperature and 0.38 ml of benzyl bromide is then added. After stirring for 30 minutes, the mixture is concentrated to dryness. The residue is taken up with ether and washed with a buffer solution of pH 2 and then with 10% Na$_2$CO$_3$ solution and the organic phase is dried over MgSO$_4$ and concentrated under vacuum to give 1.2 g of the expected product, which is used as such in the next step.

B) 5-Hydroxy-5-(3,4-dichlorophenyl)-1-benzylpiperidin-2-one 1.2 g of the compound obtained above are dissolved in 15 ml of methanol, 1 ml of hydrochloric ether is then added and the reaction mixture is left to stand for 2 hours at room temperature and concentrated to dryness. The residue is taken up with ethyl acetate and washed with water and then with 10% $Na_2CO_3$ solution and the organic phase is dried over $MgSO_4$ and concentrated under vacuum. The oil obtained crystallizes from isopropyl ether to give 0.85 g of the expected product after filtration and drying. M.p.=128° C.

C) 5-[2-(Tetrahydropyran-2-yloxy)ethoxy]-5-(3,4-dichlorophenyl)-1-benzylpiperidin-2-one 80 mg of sodium hydride as an 80% dispersion in oil are added to a solution of 0.85 g of the compound obtained above in 8 ml of DMF, the mixture is stirred for 40 minutes at 50° C. and 560 mg of 2-(2-bromoethoxy)tetrahydropyran are added. The reaction mixture is stirred for 24 hours at room temperature, 3×80 mg of sodium hydride as an 80% dispersion in oil and, respectively, 3×560 mg of 2-(2-bromoethoxy)tetrahydropyran being added over this period of time. The reaction mixture is then poured into a mixture of ice and a buffer solution of pH 2, extraction is carried out with ether, the extract is washed with water and then with 10% $Na_2CO_3$ solution and the organic phase is dried over $MgSO_4$ and concentrated under vacuum. The residue is purified by chromatography on silica gel using successively heptane, a heptane/AcOEt gradient and then pure ethyl acetate as the eluent to give 0.9 g of the expected product, which is used as such in the next step.

D) 5-(2-Hydroxyethoxy)-5-(3,4-dichlorophenyl)-1-benzylpiperidin-2-one 1 ml of hydrochloric ether is added to a solution of 900 mg of the compound obtained above in 10 ml of methanol and the reaction mixture is left to stand for 2 hours at room temperature. It is then concentrated to dryness, the residue is taken up with ethyl acetate and washed with water and then with 10% $Na_2CO_3$ solution and the organic phase is dried over $MgSO_4$ and concentrated under vacuum to give 0.75 g of the expected product, which is used as such in the next step.

E) 5-(2-Methanesulfonyloxyethoxy)-5-(3,4-dichlorophenyl)-1-benzylpiperidin-2-one 0.75 g of the compound obtained above is dissolved in 10 ml of methylene chloride, the solution is cooled to 0° C. and 0.32 ml of triethylamine and then 0.17 ml of mesyl chloride are added. The reaction mixture is left to stand for 15 minutes and then washed twice with water and the organic phase is dried over $MgSO_4$ and concentrated under vacuum to give 0.9 g of the expected product, which is used as such in the next step.

F) 4-Acetamido-4-phenyl-1-[2-[1-benzyl-5-(3,4-dichlorophenyl)-2-oxopiperid-5-yloxy]ethyl]piperidine hydrochloride hemihydrate 1.5 g of 4-phenyl-4-acetamidopiperidine hydrochloride are dissolved in 3 ml of water and the solution is rendered basic by the addition of 1 ml of concentrated NaOH solution. The mixture is then extracted twice with DCM and the organic phase is dried over $MgSO_4$; 0.9 g of the compound obtained in the previous step is added, the mixture is concentrated to dryness, 3 ml of DMF are added to the residue and the mixture is heated for 2 hours at 70° C. Iced water is then added to the reaction mixture, extraction is carried out with AcOEt, the extract is washed with 1N NaOH solution and then with water and the organic phase is dried over $MgSO_4$ and concentrated under vacuum. The residue is purified by chromatography on silica gel H using DCM and then a gradient of a DCM/MeOH mixture (up to 95/5; v/v) as the eluent. The product obtained is taken up with DCM, acidified to pH 1 by the addition of hydrochloric ether and evaporated under vacuum to give 0.87 g of the expected hydrochloride after crystallization from ether. M.p.=155° C.

EXAMPLE 2

4-Acetamido-4-phenyl-1-[2-[1-(4-fluorobenzyl)-5-(3,4-dichlorophenyl)-2-oxopiperid-5-yloxy]ethyl] piperidine hydrochloride

A) 5-(3,4-Dichlorophenyl)-1-(4-fluorobenzyl)-5-(tetrahydropyran-2-yloxy)piperidin-2-one 0.36 g of potassium tert-butylate is added to a solution of 1.0 g of the compound obtained in Preparation 1 in 15 ml of THF and the mixture is stirred for 30 minutes at RT. 0.6 g of 4-fluorobenzyl bromide is then added and the mixture is stirred for 1 hour and concentrated under vacuum. The residue is taken up with ether, washed with a buffer solution of pH 2 and with 10% $Na_2CO_3$ solution, dried over $MgSO_4$ and evaporated under vacuum. The residue is chromatographed on silica gel using heptane, then a gradient of a heptane/AcOEt mixture and finally AcOEt as the eluent to give 0.75 g of the expected product, which is used as such in the next step.

B) 5-(3,4-Dichlorophenyl)-1-(4-fluorobenzyl)-5-hydroxypiperidin-2-one 2 ml of hydrochloric ether are added to a solution of 0.75 g of the compound obtained above in 15 ml of MeOH and the reaction mixture is stirred for 2 hours at RT. It is evaporated under vacuum and the residue is extracted with AcOEt, washed with water and with 10% $Na_2CO_3$ solution, dried over $MgSO_4$ and evaporated under vacuum to give 0.48 g of the expected product after crystallization from iso ether. M.p.=146° C.

C) 5-(3,4-Dichlorophenyl)-1-(4-fluorobenzyl)-5-[2-(tetrahydropyran-2-yloxy)ethoxypiperidin-2-one 0.160 g of sodium hydride as an 80% dispersion in oil is added to a solution of 0.468 g of the compound obtained above in 5 ml of DMF and the mixture is stirred for 1 hour at RT. 0.580 g of 2-(2-bromoethoxy)tetrahydropyran is then added and the reaction mixture is stirred for 2 hours at RT. It is poured into a mixture of ice and a buffer of pH 2 and extracted with ether and the extract is washed with water, dried over $MgSO_4$ and evaporated under vacuum. The residue is chromatographed on silica gel using heptane, then a gradient of a heptane/AcOEt mixture and finally AcOEt as the eluent to give 0.44 g of the expected product, which is used as such in the next step.

D) 5-(3,4-Dichlorophenyl)-1-(4-fluorobenzyl)-5-(2-hydroxyethoxy)piperidin-2-one 0.5 ml of hydrochloric ether is added to a solution of 0.44 g of the compound obtained above in 5 ml of MeOH and the mixture is stirred for 2 hours at RT. It is concentrated under vacuum, the residue is extracted with AcOEt and the extract is washed with water and with 10% $Na_2CO_3$ solution, dried over $MgSO_4$ and evaporated under vacuum to give 0.37 g of the expected product, which is used as such in the next step.

E) 5-(3,4-Dichlorophenyl)-1-(4-fluorobenzyl)-5-(2-methanesulfonyloxyethoxy)piperidin-2-one A solution of 0.37 g of the compound obtained above in 5 ml of DCM is cooled to 0° C., 0.18 ml of triethylamine and then 0.07 ml of methanesulfonyl chloride are added and the mixture is stirred for 15 minutes. The organic phase is washed twice with water, dried over $MgSO_4$ and concen-

57 trated under vacuum to give 0.4 g of the expected product, which is used as such in the next step.

F) 4-Acetamido-4-phenyl-1-[2-[1-(4-fluorobenzyl)-5-(3,4-dichlorophenyl)-2-oxopiperid-5-yloxy]ethyl]piperidine hydrochloride 0.5 ml of concentrated NaOH is added to a solution of 0.7 g of 4-acetamido-4-phenylpiperidine hydrochloride in 3 ml of water, the mixture is extracted with DCM and the extract is dried over $MgSO_4$. 0.4 g of the compound obtained in the previous step is added to this solution, the mixture is concentrated under vacuum, 1 ml of DMF is added to the residue and the mixture is heated at 70° C. for 2 hours. Iced water is then added to the reaction mixture, extraction is carried out with AcOEt and the extract is washed with 1N NaOH solution and with saturated NaCl solution, dried over $MgSO_4$ and concentrated under vacuum. The residue is chromatographed on silica gel using DCM and then a DCM/MeOH mixture (95/5; v/v) as the eluent. The residue is taken up with DCM, acidified to pH 1 by the addition of hydrochloric ether and concentrated under vacuum to give 0.39 g of the expected hydrochloride after crystallization from iso ether. M.p.=157° C.

EXAMPLE 3

4-Phenyl-1-[2-[3-(3,4-dichlorophenyl)-1-(3-isopropoxybenzylcarbonyl)piperid-3-yloxy]ethyl]quinuclidinium chloride 1.5 hydrate A) 3-(3,4-Dichlorophenyl)-3-hydroxypiperidine hydrochloride Hydrochloric ether is added to a solution of 1.1 g of the piperidine obtained according to Preparation 2 in 15 ml of methanol until the pH is 1. The reaction mixture is then left to stand at room temperature for 1 hour and subsequently concentrated under vacuum to give 0.59 g of the expected hydrochloride after crystallization from acetone. M.p.=120° C. (dec.).

This compound can also be obtained by following the two steps of the method described below.

a) 1-Benzyl-3-(3,4-dichlorophenyl)-3-hydroxypiperidine hydrochloride

A solution of 3,4-dichlorophenylmagnesium iodide is prepared from 0.52 g of magnesium and 5.4 g of 3,4-dichloro-1-iodobenzene in 40 ml of ether. After the ether has been evaporated off, the residue is cooled to 0°–5° C., a solution of 5.4 g of 1-benzylpiperidin-3-one in 30 ml of toluene is added dropwise and the reaction mixture is stirred, the temperature being allowed to rise to RT. It is poured into saturated $NH_4Cl$ solution and extracted with DCM, the organic phase is washed with water and dried over $MgSO_4$ and the solvent is evaporated off under vacuum. The residue is taken up with DCM and acidified to pH 1 by the addition of hydrochloric ether, and the precipitate formed is wrung to give 6 g of the expected product after recrystallization from ether.

b) 3-(3,4-Dichlorophenyl)-3-hydroxypiperidine hydrochloride

A mixture of 1 g of the compound obtained in the previous step (in the form of the free base) and 0.15 g of 5% palladium-on-charcoal in 80 ml of acetic acid is hydrogenated at RT and at atmospheric pressure. The catalyst is filtered off on Célite® and the filtrate is concentrated under vacuum. The residue is taken up with 5N NaOH solution and extracted with DCM, the organic phase is washed with 5N NaOH solution and dried over $MgSO_4$ and the filtrate is evaporated under vacuum. The residue is taken up with DCM and acidified to pH 1 by the addition of hydrochloric ether, and the precipitate formed is wrung to give 0.7 g of the expected product.

B) 1-tert-Butoxycarbonyl-3-(3,4-dichlorophenyl)-3-hydroxypiperidine 0.59 g of the hydrochloride obtained above in step A is suspended in 10 ml of dioxane, 0.35 ml of triethylamine is then added, followed by 0.5 g of di-tert-butyl dicarbonate. The reaction mixture is heated at 40° C. for 2 hours and then concentrated under vacuum. The residue is taken up with ethyl acetate, washed with water, with a buffer solution of pH 2 and then with 10% sodium carbonate solution, dried over $MgSO_4$ and evaporated under vacuum to give 0.74 g of the expected product, which is used as such in the next step.

C) 1-tert-Butoxycarbonyl-3-(3,4-dichlorophenyl)-3-[2-(tetrahydropyran-2-yloxy)ethoxy]piperidine 260 mg of sodium hydride as an 80% dispersion in oil are added to a solution of 0.74 g of the product obtained above in 7 ml of dimethylformamide, and 500 mg of 2-(2-bromoethoxy)tetrahydropyran are then added after 30 minutes. After 1 hour, 1.0 g of 2-(2-bromoethoxy)tetrahydropyran and then 130 mg of sodium hydride as an 80% dispersion in oil are added. After stirring for 2 hours at room temperature, the reaction mixture is poured into a mixture of ice and a buffer solution of pH 2. Extraction is carried out with ether and the extract is washed with water and then with 10% sodium carbonate solution, dried over $MgSO_4$ and evaporated under vacuum. The residue is chromatographed on silica gel using heptane and then heptane/ethyl acetate (80/20; v/v) as the eluent to give 0.76 g of the expected product, which is used as such in the next step.

D) 3-(3,4-Dichlorophenyl)-3-(2-hydroxyethoxy)piperidine hydrochloride 5 ml of concentrated hydrochloric acid are added to a solution of 0.76 g of the piperidine obtained above in 10 ml of MeOH and the reaction mixture is then stirred at room temperature for 30 minutes. The solvent is then evaporated off under vacuum and absolute EtOH is added. The solvent is evaporated off again under vacuum and the residue is taken up with ether and then filtered off to give 0.48 g of the expected product, which is used as such in the next step.

E) 3-(3,4-Dichlorophenyl)-3-(2-hydroxyethoxy)-1-(3-isopropoxybenzylcarbonyl)piperidine 0.52 mg of triethylamine, 0.300 g of 3-isopropoxyphenylacetic acid and 0.78 g of BOP are added successively to a solution of 0.48 g of the product obtained above in 10 ml of DCM. After 15 minutes, the solvent is evaporated off under vacuum and the residue is taken up with AcOEt, washed successively with water, with 1N NaOH solution, with water and with a buffer solution of pH 2, dried over $MgSO_4$ and evaporated under vacuum. The residue is chromatographed on silica gel using heptane, then heptane/AcOEt and then pure AcOEt as the eluent to give 0.52 g of the expected product, which is used as such in the next step.

F) 3-(3,4-Dichlorophenyl)-3-(2-methanesulfonyloxyethoxy)-1-(3-isopropoxybenzylcarbonyl)piperidine 0.29 of triethylamine is added to a solution of 0.52 g of the product obtained above in 10 ml of DCM, the reaction mixture is then cooled to 0° C. and 0.15 ml of mesyl chloride is then added. The resulting reaction mixture is subsequently washed twice with water and then dried over magnesium sulfate and concentrated under vacuum to give 0.63 g of the expected product, which is used as such.

G) 4-Phenyl-1-[2-[3-(3,4-dichlorophenyl)-1-(3-isopropoxybenzylcarbonyl)piperid-3-yloxy]ethyl]quinuclidinium chloride 1.5 hydrate A mixture of 0.31 g of the compound obtained above, 0.21 g of 4-phenylquinuclidine and 1 ml of DMF is heated at 90°

C. for 1 hour. It is extracted with DCM and the extract is washed with saturated NaCl solution, with 1N hydrochloric acid solution and with saturated NaCl solution, dried over MgSO$_4$ and concentrated under vacuum. The residue is chromatographed on silica gel using DCM and then a DCM/MeOH mixture (90/10; v/v) as the eluent to give 0.26 g of the expected product after crystallization from ether. M.p.=158° C. (dec.).

EXAMPLE 4

4-Acetamido-4-phenyl-1-[2-[3-(3,4-dichlorophenyl)-1-(3-isopropoxybenzylcarbonyl)piperid-3-yloxy]ethyl]piperidine hydrochloride monohydrate 0.4 ml of concentrated NaOH is added to a solution of 0.43 g of 4-acetamido-4-phenylpiperidine hydrochloride in 0.2 ml of water, the mixture is extracted twice with DCM and the organic phase is dried over MgSO$_4$. 0.31 g of the compound obtained in step F) of EXAMPLE 3 is added to this solution and the mixture is concentrated under vacuum. 1 ml of DMF is added to the residue and the reaction mixture is heated at 90° C. for 30 minutes. It is poured into water and extracted with AcOEt and the extract is washed with 1N NaOH solution and with saturated NaCl solution, dried over MgSO$_4$ and concentrated under vacuum. The residue is chromatographed on silica gel H using DCM and then a DCM/MeOH mixture (95/5; v/v) as the eluent. The residue is taken up with DCM, acidified to pH 1 by the addition of hydrochloric ether and concentrated under vacuum to give 0.56 g of the expected hydrochloride after crystallization from iso ether. M.p.=128° C.

EXAMPLE 5

4-Acetamido-4-phenyl-1-[2-[1-benzoyl-3-(3,4-dichlorophenyl)piperid-3-yloxy]ethyl]piperidine hydrochloride hemihydrate A) 1-Benzoyl-3-(3,4-dichlorophenyl)-3-(tetrahydropyranyl-2-oxy)piperidine 0.4 ml of triethylamine is added, with stirring, to a solution of 900 mg of the piperidine obtained according to PREPARATION 2 in 10 ml of methylene chloride. The reaction mixture is cooled to 0° C. and 0.33 ml of benzoyl chloride is then added, with continued stirring. The mixture is allowed to return to room temperature and is then concentrated to dryness. The residue is taken up with ether, washed with a buffer solution of pH 2 and then with 10% Na$_2$CO$_3$ solution, dried over MgSO$_4$ and concentrated under vacuum to give 1.1 g of the expected product, which is used as such in the next step.

B) 1-Benzoyl-3-(3,4-dichlorophenyl)-3-hydroxypiperidine 1.1 g of the compound obtained above are dissolved in 20 ml of MeOH, 0.5 ml of Amberlyst® 15 resin is then added and the reaction mixture is heated for 2 hours at 60° C. The mixture is filtered and the filtrate is then concentrated to dryness. The residue is dissolved in a little ether, the solution is shaken until crystallization occurs, ether is then added and the resulting crystals are filtered off and dried to give 0.68 g of the expected product. M.p.=133° C.

C) 1-Benzoyl-3-(3,4-dichlorophenyl)-3-(2-tetrahydropyran-2-yloxyethoxy)piperidine 70 mg of sodium hydride as an 80% dispersion in oil are added to a solution of 680 mg of the compound obtained above in 15 ml of THF, the reaction mixture is stirred for 1 hour, 0.49 g of 2-(2-bromoethoxy)tetrahydropyran is then added and the mixture is stirred for 1 hour. The operation is repeated 3 times. The reaction mixture is then poured into a mixture of ice and a buffer solution of pH 2 and extracted with ether, the extract is washed with water and then with 10% Na$_2$CO$_3$ solution and the organic phase is dried over MgSO$_4$ and then concentrated under vacuum. The residue is chromatographed on silica gel using successively heptane, then a heptane/AcOEt gradient and finally pure ethyl acetate as the eluent to give 0.82 g of the expected compound, which is used as such in the next step.

D) 1-Benzoyl-3-(3,4-dichlorophenyl)-3-(2-hydroxyethoxy)piperidine 820 mg of the compound obtained above are dissolved in 15 ml of methanol, 1 ml of Amberlyst® 15 resin is added, with stirring, and the mixture is then heated for 2 hours at 60° C. The resin is then filtered off and the filtrate is concentrated to dryness. The residue is taken up with ether and washed with water and then with 10% Na$_2$CO$_3$ solution and the organic phase is dried over MgSO$_4$ and concentrated under vacuum to give 0.64 g of the expected product, which is used as such in the next step.

E) 1-Benzoyl-3-(3,4-dichlorophenyl)-3-(2-methanesulfonyloxyethoxy)piperidine 0.64 g of the compound obtained above is dissolved in 10 ml of methylene chloride, and 0.38 ml of triethylamine is added, with stirring. The reaction mixture is cooled to 0° C. and 0.19 ml of mesyl chloride is added. The resulting mixture is washed twice with water and the organic phase is dried over MgSO$_4$ and then concentrated to dryness to give 0.75 g of the expected compound, which is used as such in the next step.

F) 4-Acetamido-4-phenyl-1-[2-[1-benzoyl-3-(3,4-dichlorophenyl)piperid-3-yloxy]ethyl]piperidine hydrochloride hemihydrate 0.61 g of 4-phenyl-4-acetamidopiperidine hydrochloride is dissolved in 1 ml of water and the solution is rendered basic by the addition of 0.5 ml of concentrated NaOH solution. The reaction mixture is extracted twice with DCM and the organic phase is dried over MgSO$_4$. 0.37 g of the compound obtained in the previous step is added to this solution and the resulting mixture is concentrated to dryness. 1 ml of DMF is added to the residue and the reaction mixture is heated for 2 hours at 70° C. It is then diluted with water and extracted with AcOEt, the extract is washed with 1N NaOH solution and then with saturated NaCl solution and the organic phase is dried over MgSO$_4$ and concentrated under vacuum. The residue is chromatographed on silica gel H using DCM and then a DCM/MeOH mixture (95/5; v/v) as the eluent. The product obtained is taken up with DCM, acidified to pH 1 by the addition of hydrochloric ether and concentrated under vacuum to give 0.37 g of the expected hydrochloride after crystallization from ether. M.p.=141° C. (dec.).

EXAMPLE 6

4-Hydroxy-4-phenyl-1-[2-[1-benzoyl-3-(3,4-dichlorophenyl)piperid-3-yloxy]ethyl]piperidine hydrochloride 370 mg of 1-benzoyl-3-(3,4-dichlorophenyl)-3-(2-methanesulfonyloxyethyl)piperidine, obtained as described in EXAMPLE 5, step E), are mixed with 350 mg of 4-phenyl-4-hydroxypiperidine and 1 ml of DMF and the reaction mixture is heated for 2 hours 30 minutes at 70° C. It is diluted with water and extracted with ethyl acetate, the extract is washed with 1N sodium hydroxide solution and then with saturated NaCl solution and the organic phase is dried over MgSO$_4$ and concentrated under vacuum. The residue is chromatographed on silica gel H using DCM and then a DCM/MeOH mixture (95/5; v/v) as the eluent. The product obtained is taken up with DCM, acidified to pH 1 by the addition of hydrochloric ether and concentrated under vacuum to give 0.37 g of the expected hydrochloride after crystallization from ether. M.p.=206° C.

EXAMPLE 7

4-Phenyl-4-propionyloxy-1-[2-[1-benzoyl-3-(3,4-dichlorophenyl)piperid-3-yloxy]ethyl]piperidine hydrochloride hemihydrate 270 mg of the compound obtained in the previous Example are dissolved in 5 ml of methylene chloride, and 0.17 ml of triethylamine and 0.1 ml of propionyl chloride are then added, with stirring. After 15 minutes, the reaction mixture is washed with water and then with 10% Na$_2$CO$_3$ solution and the organic phase is dried over MgSO$_4$ and concentrated under vacuum. The residue is chromatographed on silica gel H using DCM and then a DCM/MeOH mixture (97/3; v/v) as the eluent. The product obtained is taken up with DCM, acidified to pH 1 by the addition of hydrochloric ether and concentrated under vacuum to give 0.205 g of the expected hydrochloride after crystallization from ether. M.p.=152° C.

EXAMPLE 8

4-Phenyl-1-[2-[1-(3,4-dichlorophenyl)-2-[N-methyl-N-(3-isopropoxybenzylcarbonyl)amino]ethoxy] ethyl]quinuclidinium methanesulfonate A) N-Methyl-2-(3,4-dichlorophenyl)-2-hydroxyethanamine hydrochloride 20 ml of hydrochloric ether are added to a solution of 26.5 g of the compound obtained in Preparation 3 in 300 ml of MeOH and the mixture is stirred for 1 hour at RT and concentrated under vacuum to give 19.2 g of the expected product after crystallization from acetone. M.p.=193° C.

B) N-Methyl-N-tert-butoxycarbonyl-2-(3,4-dichlorophenyl)-2-hydroxyethanamine 2.9 g of sodium hydroxide and then 100 ml of dioxane are added to a solution of 18 g of the compound obtained above in 100 ml of water. 5 ml of triethylamine are then added, followed by 17 g of di-tert-butyl dicarbonate, and the mixture is heated for 1 hour at 60° C. The dioxane is removed by concentration under vacuum, the aqueous residue is extracted with ether and the extract is washed with a buffer solution of pH 2, with water and with 10% Na$_2$CO$_3$ solution, dried over MgSO$_4$ and evaporated under vacuum to give 21.07 g of the expected product after crystallization from pentane. M.p.=88° C.

C) N-Methyl-N-tert-butoxycarbonyl-2-(3,4-dichlorophenyl)-2-[2-(tetrahydropyran-2-yloxy)ethoxy]ethanamine 4.5 g of sodium hydride as a 60% dispersion in oil are added in portions to a solution of 18 g of the compound obtained above in 150 ml of DMF and the mixture is maintained at a temperature of 20° C. for 5 minutes. 18 ml of 2-(2-bromoethoxy)tetrahydropyran are then added and the reaction mixture is stirred for 1 hour at RT. It is poured into a mixture of ice and a buffer solution of pH 2 and extracted with ether and the extract is washed with water and with 10% Na$_2$CO$_3$ solution, dried over MgSO$_4$ and concentrated under vacuum. The residue is chromatographed on silica gel using heptane and then a heptane/AcOEt mixture (75/25; v/v) as the eluent to give 17.8 g of an oil of the expected product, which is used as such in the next step.

D) N-Methyl-2-(3,4-dichlorophenyl)-2-(2-hydroxyethoxy) ethanamine hydrochloride 25 ml of concentrated hydrochloric acid are added to a solution of 7.7 g of the compound obtained above in 50 ml of MeOH and the mixture is stirred overnight at RT. It is concentrated under vacuum to give 4.9 g of the expected product after crystallization from acetone. M.p.=185° C.

E) N-Methyl-N-(3-isopropoxybenzylcarbonyl)-2-(3,4-dichlorophenyl)-2-(2-hydroxyethoxy)ethanamine 1.2 ml of triethylamine, 670 mg of 3-isopropoxyphenylacetic acid and 1.75 g of BOP are added successively to a solution of 1.0 g of the product obtained above in 20 ml of methylene chloride. After 10 minutes, the solvent is evaporated off under vacuum and the residue is taken up with ether and washed successively with water, twice with 1N hydrochloric acid and then with water and with 1N NaOH solution. The residue obtained is dried over magnesium sulfate and concentrated under vacuum to give 1.3 g of the expected product, which is used as such in the next step.

F) N-Methyl-N-(3-isopropoxybenzylcarbonyl)-2-(3,4-dichlorophenyl)-2-(2-methanesulfonyloxyethoxy) ethanamine 0.54 ml of triethylamine is added to a solution of 1.3 g of the product obtained above in 20 ml of DCM and the reaction mixture is then cooled to 0° C. 0.3 ml of mesyl chloride is then added dropwise and the mixture is concentrated under vacuum. The residue is extracted with ether and the extract is washed with water and with 10% sodium carbonate solution, dried over magnesium sulfate and concentrated under vacuum to give 1.5 g of the expected product, which is used as such in the next step.

G) 4-Phenyl-1-[2-[1-(3,4-dichlorophenyl)-2-[N-methyl-N-(3-isopropoxybenzylcarbonyl)amino]ethoxy]ethyl] quinuclidinium methanesulfonate A mixture of 1.5 g of the compound obtained above, 0.83 g of 4-phenylquinuclidine and 0.7 ml of DMF is heated at 90° C. for 1 hour 15 minutes. After cooling, the reaction mixture is taken up with acetone and stirred until crystallization occurs. This gives 1.56 g of the expected product. M.p.=175° C.

EXAMPLE 9

4-Hydroxy-4-phenyl-1-[2-[1-(3,4-dichlorophenyl)-2-(N-methyl-N-benzyloxycarbonylamino)ethoxy] ethyl]piperidine hydrochloride A) N-Methyl-N-tert-butoxycarbonyl-2-(3,4-dichlorophenyl)-2-(2-hydroxyethoxy)ethanamine 0.56 g of pyridinium paratoluenesulfonate is added to a solution of 10 g of the compound obtained in EXAMPLE 8, step C), in 100 ml of MeOH and the reaction mixture is refluxed for 1 hour 15 minutes. It is concentrated under vacuum and the residue is taken up with ether, washed with water and with a buffer solution of pH 2, dried over MgSO$_4$ and concentrated under vacuum to give 8.2 g of the expected product, which is used as such in the next step.

B) N-Methyl-N-tert-butoxycarbonyl-2-(3,4-dichlorophenyl)-2-(2-methanesulfonyloxyethoxy)ethanamine A solution of 8.2 g of the compound obtained above in 100 ml of DCM is cooled to 0° C. and 3.8 ml of triethylamine and then 2.1 ml of methanesulfonyl chloride are added. After stirring for 15 minutes, the mixture is evaporated under vacuum and the residue is taken up with ether, washed twice with water and with 10% Na$_2$CO$_3$ solution, dried over MgSO$_4$ and concentrated under vacuum to give 9.76 g of the expected product, which is used as such in the next step.

C) 4-Hydroxy-4-phenyl-1-[2-[1-(3,4-dichlorophenyl)-2-(N-methyl-N-tert-butoxycarbonylamino)ethoxy]ethyl]piperidine A mixture of 5 g of the compound obtained above, 4.5 g of 4-hydroxy-4-phenylpiperidine and 10 ml of DMF is heated at 70° C. for 2 hours. The reaction mixture is poured into iced water and extracted with AcOEt and the extract is washed with 1N NaOH solution, with water and with saturated NaCl solution, dried over MgSO$_4$ and concentrated under vacuum to give 5.80 g of the expected product, which is used as such in the next step.

D) 4-Hydroxy-4-phenyl-1-[2-[1-(3,4-dichlorophenyl)-2-(N-methylamino)ethoxy]ethyl]piperidine dihydrochloride 10 ml of concentrated hydrochloric acid are added to a solution of 5.8 g of the compound obtained above in 30 ml of MeOH and the reaction mixture is stirred for 1 hour at RT. It is concentrated under vacuum, the residue is dissolved in the minimum amount of MeOH and this solution is poured into ether. The precipitate formed is filtered off, washed with ether and dried under vacuum to give 5.2 g of the expected product. M.p.=202° C.

E) 4-Hydroxy-4-phenyl-1-[2-[1-(3,4-dichlorophenyl)-2-(N-methyl-N-benzyloxycarbonylamino)ethoxy]ethyl]piperidine hydrochloride 0.9 ml of triethylamine is added to a solution of 1 g of the compound obtained above in 20 ml of DCM, the mixture is then cooled to 0° C. and 0.3 ml of benzyl chloroformate is added dropwise. The reaction medium is washed twice with water, dried over MgSO$_4$ and concentrated under vacuum. The residue is chromatographed on silica H using DCM and then a DCM/MeOH mixture (95/5; v/v) as the eluent. The product obtained is taken up with DCM, acidified to pH 1 by the addition of hydrochloric ether and concentrated under vacuum to give 1.1 g of the expected hydrochloride after crystallization from iso ether. M.p.=146° C.

EXAMPLE 10

4-Phenyl-4-propionyloxy-1-[2-[1-(3,4-dichlorophenyl)-2-(N-methyl-N-benzyloxycarbonylamino)ethoxy]ethyl]piperidine hydrochloride hemihydrate 670 mg of the compound obtained in EXAMPLE 9 are dissolved in 10 ml of methylene chloride, and 0.2 ml of triethylamine and 0.2 ml of propionyl chloride are then added, with stirring. After 15 minutes, the reaction mixture is washed with water and then with 10% Na$_2$CO$_3$ solution and the organic phase is dried over MgSO$_4$ and concentrated under vacuum. The residue is chromatographed on silica gel H using DCM and then a DCM/MeOH mixture (97/3; v/v) as the eluent. The product obtained is taken up with DCM, acidified to pH 1 by the addition of hydrochloric ether and concentrated under vacuum to give 0.52 g of the expected hydrochloride after crystallization from pentane. M.p.=115° C. (dec.).

EXAMPLE 11

4-Acetamido-4-phenyl-1-[2-[1-(3,4-dichlorophenyl)-2-(N-methyl-N-benzoylamino)ethoxy]ethyl]piperidine hydrochloride A) 4-Acetamido-4-phenyl-1-[2-[1-(3,4-dichlorophenyl)-2-(N-methyl-N-tert-butoxycarbonylamino)ethoxy]ethyl]piperidine 5 ml of concentrated NaOH are added to a solution of 8 g of 4-acetamido-4-phenylpiperidine hydrochloride in 6 ml of water, the mixture is extracted three times with DCM and the extract is dried over MgSO$_4$. 4.7 g of the compound obtained in EXAMPLE 9, step B), are added to this solution and the mixture is concentrated under vacuum. 10 ml of DMF are added to the residue obtained and the reaction mixture is heated at 70° C. for 2 hours. It is poured into iced water and extracted with AcOEt and the extract is washed with 1N NaOH solution, with water and with saturated NaCl solution, dried over MgSO$_4$ and concentrated under vacuum to give 6.0 g of the expected product, which is used as such in the next step.

B) 4-Acetamido-4-phenyl-1-[2-[1-(3,4-dichlorophenyl)-2-(N-methylamino)ethoxy]ethyl]piperidine dihydrochloride 10 ml of concentrated hydrochloric acid are added to a solution of 6 g of the compound obtained above in 30 ml of MeOH and the mixture is stirred for 1 hour at RT. It is concentrated under vacuum, the residue is dissolved in the minimum amount of MeOH and this solution is poured into ether. The precipitate formed is filtered off and dried under vacuum to give 6.2 g of the expected product. M.p.=195° C. (dec.).

C) 4-Acetamido-4-phenyl-1-[2-[1-(3,4-dichlorophenyl)-2-(N-methyl-N-benzoylamino)ethoxy]ethyl]piperidine hydrochloride 0.4 ml of triethylamine is added to a solution of 0.5 g of the compound obtained above in 10 ml of DCM, the mixture is then cooled to 0° C. and 0.11 ml of benzoyl chloride is added dropwise. The mixture is concentrated under vacuum, the residue is extracted with AcOEt and the extract is washed with water, with 0 1N NaOH solution and with saturated NaCl solution, dried over MgSO$_4$ and concentrated under vacuum. The residue is chromatographed on silica H using DCM and then a DCM/MeOH mixture (95/5; v/v) as the eluent. The product obtained is taken up with DCM, acidified to pH 1 by the addition of hydrochloric ether and concentrated under vacuum to give 0.41 g of the expected hydrochloride after crystallization from iso ether. M.p.=133° C.

EXAMPLE 12

4-Acetamido-4-phenyl-1-[2-[1-(3,4-dichlorophenyl)-2-(N-methyl-N-benzyloxycarbonylamino)ethoxy]ethyl]piperidine hydrochloride 0.41 ml of triethylamine is added to a solution of 0.5 g of the compound obtained in EXAMPLE 11, step B), in 10 ml of DCM, the mixture is then cooled to 0° C. and 0.14 ml of benzyl chloroformate is added dropwise. The reaction mixture is washed twice with water, dried over MgSO$_4$ and concentrated under vacuum. The residue is chromatographed on silica gel H using DCM and then a DCM/MeOH mixture (94/6; v/v) as the eluent. The product obtained is taken up with DCM, acidified to pH 1 by the addition of hydrochloric ether and concentrated under vacuum to give 0.39 g of the expected hydrochloride after crystallization from iso ether. M.p.=135° C.

EXAMPLE 13

4-Acetamido-4-phenyl-1-[2-[1-(3,4-dichlorophenyl)-2-(N-methyl-N-benzylcarbonylamino)ethoxy]ethyl]piperidine hydrochloride hemihydrate 0.46 ml of triethylamine and then 0.5 g of BOP are added to a mixture of 0.5 g of the compound obtained in EXAMPLE 11, step B), 0.127 g of phenylacetic acid and 10 ml of DCM. The resulting mixture is concentrated under vacuum and the residue is taken up with AcOEt, washed with water, with 1N NaOH solution and with saturated NaCl solution, dried over MgSO$_4$ and concentrated under vacuum. The residue is chromatographed on silica gel H using DCM and then a DCM/MeOH mixture (94/6; v/v) as the eluent. The product obtained is taken up with DCM, acidified to pH 1 by the addition of hydrochloric ether and concentrated under vacuum to give 0.42 g of the expected hydrochloride after crystallization from iso ether. M.p.=125° C.

EXAMPLE 14

4-Benzyl-1-[2-[3-(3,4-dichlorophenyl)-1-(3-isopropoxybenzylcarbonyl)piperid-3-yloxy]ethyl] quinuclidinium chloride monohydrate A mixture of 0.33 g of the compound obtained in step F) of EXAMPLE 3, 0.2 g of 4-benzylquinuclidine and 1 ml of DMF is heated at 80° C. for 3 hours. After cooling, the reaction mixture is poured into water and extracted with DCM, the organic phase is washed with water, twice with 1N hydrochloric acid solution and twice with saturated NaCl solution and dried over MgSO$_4$ and the solvent is evaporated off under vacuum to give 0.3 g of the expected product. M.p.=110° C.

EXAMPLE 15

4-Phenyl-1-[2-[N-methyl-N-[1-(3,4-dichlorophenyl)-2-[N'-methyl-N'-(3-isopropoxybenzylcarbonyl) amino]ethyl]amino]ethyl]quinuclidinium chloride hydrochloride dihydrate A) N-Methyl-2-(3,4-dichlorophenyl)-2-[N'-methyl-N'-(2-hydroxyethyl)amino]ethylamine dihydrochloride 20 ml of hydrochloric ether are added to a solution of 6 g of the compound obtained in Preparation 4 in 100 ml of MeOH and the reaction mixture is stirred for 1 hour at RT. It is concentrated under vacuum to give 5.5 g of the expected product after crystallization from acetone. M.p.=210° C. (dec.).

B) N-Methyl-N-(3-isopropoxybenzylcarbonyl)-2-(3,4-dichlorophenyl)-2-[N'-methyl-N'-(2-hydroxyethyl)amino] ethylamine 0.35 g of 3-isopropoxyphenylacetic acid, 0.85 ml of triethylamine and then 0.9 g of BOP are added successively to a solution of 0.6 g of the compound obtained in the previous step in 20 ml of DCM and the reaction mixture is stirred for 1 hour at RT. It is concentrated under vacuum, the residue is extracted with AcOEt, the organic phase is washed with water, with 1N NaOH solution and with saturated NaCl solution and dried over MgSO$_4$ and the solvent is evaporated off under vacuum. The residue is chromatographed on silica H using DCM and then a DCM/MeOH mixture (98/2; v/v) as the eluent to give 0.51 g of the expected product, which is used as such.

C) N-Methyl-N-(3-isopropoxybenzylcarbonyl)-2-(3,4-dichlorophenyl)-2-[N'-methyl-N'-(2-methanesulfonyloxyethyl)amino]ethylamine A solution of 0.51 g of the compound obtained in the previous step and 0.19 ml of triethylamine in 10 ml of DCM is cooled to 0° C. and 0.1 ml of methanesulfonyl chloride is added. The reaction mixture is concentrated under vacuum, the residue is extracted with AcOEt, the organic phase is washed with water and with saturated Na$_2$CO$_3$ solution and dried over MgSO$_4$ and the solvent is evaporated off under vacuum to give 0.6 g of the expected product, which is used as such.

D) 4-Phenyl-1-[2-[N-methyl-N-[1-(3,4-dichlorophenyl)-2-[N'-methyl-N'-(3-isopropoxybenzylcarbonyl)amino]ethyl] amino]ethyl]quinuclidinium chloride hydrochloride dihydrate A mixture of 0.6 g of the compound obtained in the previous step, 0.36 g of 4-phenylquinuclidine and 1 ml of DMF is heated at 90° C. for 30 minutes. After cooling, the reaction mixture is poured into ether, the solvent is decanted and the resulting gum is dissolved in DCM. The methylene chloride phase is washed three times with 1N HCl solution and the organic phase is then stirred with saturated NaCl solution. The crystalline product formed is wrung and washed with water and then with ether to give 0.46 g of the expected product after drying. M.p.=225° C. (dec.).

EXAMPLE 16

4-Acetamido-4-phenyl-1-[2-[N-methyl-N-[1-(3,4-dichlorophenyl)-2-(N'-benzoyl-N'-methylamino) ethyl]amino]ethyl]piperidine dihydrochloride hemihydrate A) N-(tert-Butoxycarbonyl)-N-methyl-2-(3,4-dichlorophenyl)-2-[N'-methyl-N'-(2-hydroxyethyl)amino] ethylamine 1 g of NaOH pellets and then 40 ml of dioxane and 2.8 g of di-tert-butyl dicarbonate are added to a solution of 4 g of the compound obtained in step A of EXAMPLE 15 in 20 ml of water and the mixture is stirred for two hours at RT. The dioxane is concentrated under vacuum, the aqueous phase is extracted with ether, the organic phase is washed with water and dried over MgSO$_4$ and the solvent is evaporated off under vacuum. The residue is chromatographed on silica using heptane and then a gradient of a heptane/AcOEt mixture (up to 20/80; v/v) as the eluent to give 2.5 g of the expected product, which is used as such.

B) N-(tert-Butoxycarbonyl)-N-methyl-2-(3,4-dichlorophenyl)-2-[N'-methyl-N'-(2-methanesulfonyloxyethyl)amino]ethylamine A solution of 2.4 g of the compound obtained in the previous step in 30 ml of DCM is cooled to −10° C. and 1.1 ml of triethylamine and then 0.6 ml of methanesulfonyl chloride are added. The reaction mixture is concentrated under vacuum, the residue is extracted with ether, the organic phase is washed with water and with saturated Na$_2$CO$_3$ solution and dried over MgSO$_4$ and the solvent is evaporated off under vacuum to give 2.6 g of the expected product in the form of an oil, which is used immediately.

C) 4-Acetamido-4-phenyl-1-[2-[N-methyl-N-[1-(3,4-dichlorophenyl)-2-(N'-tert-butoxycarbonyl-N'-methylamino)ethyl]amino]ethyl]piperidine A mixture of 2.6 g of the compound obtained in the previous step, 5 g of 4-acetamido-4-phenylpiperidine p-toluenesulfonate, 4.4 g of potassium carbonate and 50 ml of acetonitrile is heated at 80° C. for two hours. The reaction mixture is concentrated under vacuum, the residue is extracted with AcOEt, the organic phase is washed with water, with 1N NaOH solution and with saturated NaCl solution and dried over MgSO$_4$ and the solvent is evaporated off under vacuum. The residue is chromatographed on silica H using DCM and then a DCM/MeOH mixture (90/10; v/v) as the eluent to give 3.1 g of the expected product, which is used as such.

D) 4-Acetamido-4-phenyl-1-[2-[N-methyl-N-[1-(3,4-dichlorophenyl)-2-(methylamino)ethyl]amino]ethyl] piperidine trihydrochloride 10 ml of concentrated HCl solution are added to a solution of 3.1 g of the compound obtained in the previous step in 15 ml of MeOH and the reaction mixture is stirred for 1 hour at RT. It is concentrated under vacuum, the residue is taken up with an EtOH/toluene mixture and the resulting mixture is concentrated under vacuum again. The residue is taken up with acetone and stirred until crystallization occurs. The crystalline product is wrung and dried to give 3 g of the expected product. M.p.=210° C. (dec.).

E) 4-Acetamido-4-phenyl-1-[2-[N-methyl-N-[1-(3,4-dichlorophenyl)-2-(N'-benzoyl-N'-methylaminamino]ethylamino]ethyl]piperidine dihydrochloride hemihydrate 0.62 ml of triethylamine is added to a solution of 0.6 g of the compound obtained in the previous step in 20 ml of DCM, and 0.12 ml of benzoyl chloride is then added dropwise. The reaction mixture is concentrated under vacuum, the residue is extracted with AcOEt, the organic phase is washed with water, with 1N NaOH solution and with saturated NaCl solution and dried over MgSO$_4$ and the solvent is evaporated off under vacuum. The residue is chromatographed on silica H using DCM and then a DCM/MeOH mixture (90/10; v/v) as the eluent. The product obtained is dissolved in DCM, acidified to pH 1 by the addition of hydrochloric ether and concentrated under vacuum to give 0.59 g of the expected product after crystallization from an acetone/ether mixture. M.p.=185° C. (dec.).

EXAMPLE 17

4-Acetamido-4-phenyl-1-[2-[N-methyl-N-[1-(3,4-dichlorophenyl)-2-[N'-(benzylcarbonyl)-N'-methylamino]ethyl]amino]ethyl]piperidine dihydrochloride hemihydrate 0.65 ml of triethylamine, 0.14 g of phenylacetic acid and then 0.54 g of BOP are added to a solution of 0.6 g of the compound obtained in step D of EXAMPLE 16 in 20 ml of DCM and the reaction mixture is stirred for 30 minutes at RT. It is concentrated under vacuum, the residue is extracted with AcOEt, the organic phase is washed with water, with 1N NaOH solution and with saturated NaCl solution and dried over MgSO$_4$ and the solvent is evaporated off under vacuum. The residue is chromatographed on silica H using DCM and then a gradient of a DCM/MeOH mixture (up to 90/10; v/v) as the eluent. The expected product is dissolved in DCM, acidified to pH 1 by the addition of hydrochloric ether and concentrated under vacuum to give 0.54 g of the expected product after crystallization from ether. M.p.=180° C. (dec.).

EXAMPLE 18

4-Acetamido-4-phenyl-1-[2-[N-methyl-N-[1-(3,4-dichlorophenyl)-2-[N'-(benzyloxycarbonyl)-N'-methylamino]ethyl]amino]ethyl]piperidine dihydrochloride 0.62 ml of triethylamine and then 0.15 ml of benzyl chloroformate are added to a solution of 0.6 g of the compound obtained in step D of EXAMPLE 16 in 20 ml of DCM. The reaction mixture is concentrated under vacuum, the residue is extracted with AcOEt, the organic phase is washed with water and with 1N NaOH solution and dried over MgSO$_4$ and the solvent is evaporated off under vacuum. The residue is chromatographed on silica H using DCM and then a gradient of a DCM/MeOH mixture (up to 90/10; v/v) as the eluent. The expected product is dissolved in DCM, acidified to pH 1 by the addition of hydrochloric ether and concentrated under vacuum to give 0.57 g of the expected product after crystallization from ether. M.p.=164° C. (dec.).

What is claimed is:

1. A compound of the formula

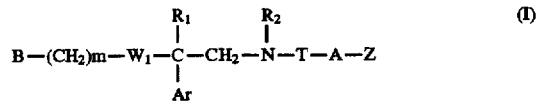

in which:

$W_1$ is an oxygen atom or a group —NR—, in which R is a hydrogen, a $(C_1-C_7)$-alkyl or a benzyl;

m is equal to 2 or 3;

$R_1$ is hydrogen or a $(C_1-C_4)$-alkyl group;

$R_2$ is a hydrogen, a $(C_1-C_7)$-alkyl, an ω-$(C_1-C_4)$-alkoxy-$(C_2-C_4)$-alkylene, an ω-$(C_1-C_4)$-alkylcarbonyloxy-$(C_2-C_4)$-alkylene, and ω-hydroxy-$(C_2-C_4)$-alkylene, an ω-$(C_1-C_4)$-alkylthio-$(C_2-C_4)$-alkylene, an ω-$(C_1-C_4)$-alkoxycarbonyl-$(C_2-C_4)$-alkylene, an ω-carboxy-$(C_2-C_4)$-alkylene, an ω-$(C_1-C_4)$-alkylcarbonyl-$(C_2-C_4)$-alkylene, an ω-benzoyloxy-$(C_2-C_4)$-alkylene, an ω-benzyloxy-$(C_2-C_4)$-alkylene, an ω-formyloxy-$(C_2-C_4)$-alkylene, an ω-$R_5$NHCOO—$(C_2-C_4)$-alkylene, an ω-$R_6R_7$NCO—$(C_2-C_4)$-alkylene, an ω-$R_8R_9$N—$(C_2-C_4)$-alkylene, an ω-$R_{10}$CONR$_{11}$—$(C_2-C_4)$-alkylene, an ω-$R_{12}$OCONR$_{11}$—$(C_2-C_4)$-alkylene, an ω-$R_6R_7$NCONR$_{11}$—$(C_2-C_4)$-alkylene, an ω-$R_{13}SO_2NR_{11}$—$(C_2-C_4)$-alkylene or an ω-cyano-$(C_1-C_3)$-alkylene;

or alternatively $R_1$ and $R_2$ together form a group —(CH$_2$)$_n$—CQ—, where Q=H$_2$ or O and n is equal to 1, 2 or 3;

T is the group —CH$_2$— or one of the groups

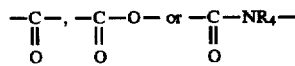

in which $R_4$ is hydrogen or a $(C_1-C_4)$-alkyl group, with the proviso that T is —CH$_2$— if Q is oxygen and one of the following groups:

if Q is hydrogen;

A is a direct bond, a group —(CH$_2$)$_t$—, in which t is equal to 1, 2 or 3, or a group —CH=CH—;

Z is an optionally substituted, mono-, di- or tricyclic aromatic or heteroaromatic group;

Ar is a phenyl which is unsubstituted or monosubstituted or polysubstituted by a substituent selected from a halogen atom, a hydroxyl, a $(C_1-C_4)$-alkoxy, a $(C_1-C_4)$-alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a $(C_1-C_4)$-alkyl or a benzyl; an imidazolyl which is unsubstituted or substituted by a halogen atom; a pyridyl which is unsubstituted or substituted by a halogen atom; or a biphenyl;

$R_5$ is a $(C_1-C_7)$-alkyl or a phenyl;

$R_6$ and $R_7$ are each independently a hydrogen or a $(C_1-C_7)$-alkyl; $R_7$ can also be a $(C_3-C_7)$-cycloalkyl, a $(C_3-C_7)$-cycloalkylmethyl, a phenyl or a benzyl; or alternatively $R_6$ and $R_7$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_8$ and $R_9$ are each independently a hydrogen or a $(C_1-C_7)$-alkyl; $R_9$ can also be a $(C_3-C_7)$-cycloalkylmethyl or a benzyl;

$R_{10}$ is a hydrogen, a $(C_1-C_7)$-alkyl, a vinyl, a phenyl, a benzyl, a pyridyl or a $(C_3-C_7)$-cycloalkyl which is unsubstituted or substituted by one or more methyls;

$R_{11}$ is a hydrogen or a $(C_1-C_7)$-alkyl;

$R_{12}$ is a $(C_1-C_7)$-alkyl or a phenyl;

$R_{13}$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

B is:
i—either a group $B_1$ of the formula

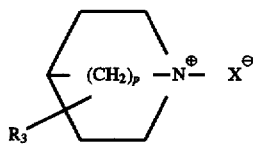

in which:
p is equal to one or two;
$R_3$ is a hydrogen, a $(C_1-C_4)$-alkyl, a phenyl or a benzyl; and
$X^\ominus$ is an anion;
ii—or a group $B_2$ of the formula

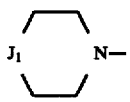

in which
$J_1$ is:
ii$_1$—either a group

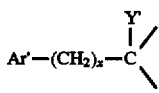

in which:
x is equal to zero or one;
Ar' is a phenyl which is unsubstituted or monosubstituted or polysubstituted by a substituent selected from a halogen atom, a nitro, a hydroxyl, a trifluoromethyl, a $(C_1-C_4)$-alkyl, a $(C_1-C_4)$-alkoxy and a methylenedioxy, said substituents being identical or different; a pyridyl; a thienyl; a pyrimidyl; or an imidazolyl which is unsubstituted or substituted by a $(C_1-C_4)$-alkyl; and
Y' is a hydrogen, a $(C_1-C_7)$-alkyl, a formyl, a $(C_1-C_7)$-alkylcarbonyl, a cyano, a group $-(CH_2)_q-OH$, a group $(C_1-C_7)$-alkyl-O—$(CH_2)_q$—, a group $-(CH_2)_q-NR_4COR_{14}$, a group $R_{15}COO-(CH_2)_q-$, a group $(C_1-C_7)$-alkyl-NHCOO—$(CH_2)_q$—, a group $-NR_{16}R_{17}$, a group $-CH_2-NR_{18}R_{19}$, a group $-CH_2-CH_2-NR_{18}R_{19}$, a group $-(CH_2)_q-NR_4COOR_{20}$, a group $-(CH_2)_q-NR_4SO_2R_{21}$, a group $-(CH_2)_q-NR_4CONR_{22}R_{23}$, a carboxyl, a $(C_1-C_7)$-alkoxycarbonyl, a group $-CONR_{22}R_{23}$, a carboxymethyl, a $(C_1-C_7)$-alkoxycarbonylmethyl, a group $-CH_2-CONR_{22}R_{23}$, a mercapto or a $(C_1-C_4)$-alkylthio;

or alternatively Y' forms an additional bond with the carbon atom to which it is bonded and with the adjacent carbon atom in the piperidine;

q is equal to zero, one or two;

$R_4$ is a hydrogen or a $(C_1-C_4)$-alkyl;

$R_{14}$ is a hydrogen, a $(C_1-C_7)$-alkyl, a phenyl, a pyridyl, a vinyl, a benzyl or a $(C_3-C_7)$-cycloalkyl which is unsubstituted or substituted by one or more methyls;

or $R_4$ and $R_{14}$ together are a group $-(CH_2)_u-$, in which u is equal to three or four;

$R_{15}$ is a hydrogen; a $(C_1-C_7)$-alkyl; a $(C_3-C_7)$-cycloalkyl which is unsubstituted or substituted by one or more methyls; a phenyl; or a pyridyl;

$R_{16}$ and $R_{17}$ are each independently a hydrogen or a $(C_1-C_7)$-alkyl; $R_{17}$ can also be a $(C_3-C_7)$-cycloalkylmethyl, a benzyl or a phenyl; or alternatively and $R_{17}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

$R_{18}$ and $R_{19}$ are each independently a hydrogen or a $(C_1-C_7)$-alkyl; $R_{19}$ can also be a $(C_3-C_7)$-cycloalkylmethyl or a benzyl;

$R_{20}$ is a $(C_1-C_7)$-alkyl or a phenyl;

$R_{21}$ is a $(C_1-C_7)$-alkyl; an amino which is free or substituted by one or two $(C_1-C_7)$-alkyls; or a phenyl which is unsubstituted or monosubstituted or polysubstituted by a substituent selected from a halogen atom, a $(C_1-C_7)$-alkyl, a trifluoromethyl, a hydroxyl, a $(C_1-C_7)$-alkoxy, a carboxyl, a $(C_1-C_7)$-alkoxycarbonyl, a $(C_1-C_7)$-alkylcarbonyloxy, a cyano, a nitro and an amino which is free or substituted by one or two $(C_1-C_7)$-alkyls, said substituents being identical or different;

$R_{22}$ and $R_{23}$ are each independently a hydrogen or a $(C_1-C_7)$-alkyl; $R_{23}$ can also be a $(C_3-C_7)$-cycloalkyl, a $(C_3-C_7)$-cycloalkylmethyl, a hydroxyl, a $(C_1-C_4)$-alkoxy, a benzyl or a phenyl;

or alternatively $R_{22}$ and $R_{23}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$-alkyl;

ii$_2$—or a group

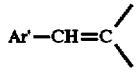

in which
Ar' is as defined above;

ii₃—or a group

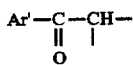

in which

Ar' is as defined above;
ii₄—or a group

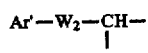

in which:

Ar+ is as defined above;

W₂ is an oxygen atom, a sulfur atom, a sulfinyl, a sulfonyl or a group —NR₂₄—;

R₂₄ is a hydrogen, a $(C_1-C_4)$-alkyl, a $(C_1-C_4)$-alkylcarbonyl or a group —$(CH_2)_v$—NR₂₅R₂₆;

v is equal to one, two or three; and

R₂₅ and R₂₆ are each independently a hydrogen or a $(C_1-C_4)$-alkyl; or alternatively R₂₅ and R₂₆, together with the nitrogen atom to which they are bonded, form a heterocycle selected from pyrrolidine, piperidine and morpholine;

iii—or a group B₃ of the formula

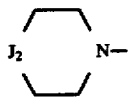

in which

J₂ is:
iii₁—either a group

iii₂—or a group

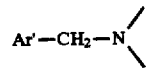

iii₃—or a group

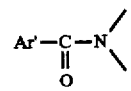

iii₄—or a group

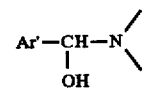

iii₅—or a group

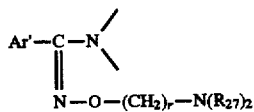

in which groups:

Ar' is as defined above;
r is two or three; and
R₂₇ is a $(C_1-C_4)$-alkyl;
iv—or a group B₄ of the formula

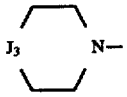

in which

J₃ is:
a group

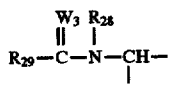

in which:

W₃ is an oxygen atom, a sulfur atom or a group NR₃₀, in which R₃₀ is a hydrogen or a $(C_1-C_3)$-alkyl;

R₂₈ is a hydrogen; a $(C_1-C_6)$-alkyl; a $(C_3-C_6)$-alkenyl in which a vinylic carbon atom is not bonded to the nitrogen atom; a 2-hydroxyethyl; a $(C_3-C_7)$-cycloalkyl; a phenyl which is unsubstituted or monosubstituted or polysubstituted by a substituent selected from a halogen atom, a trifluoromethyl, a $(C_1-C_4)$-alkyl, a $(C_1-C_4)$-alkoxy, a nitro, an amino and a hydroxyl, said substituents being identical or different; or a 6-membered heteroaryl containing one or two nitrogen atoms as heteroatoms, said heteroaryl being unsubstituted or monosubstituted or polysubstituted by a substituent selected from a halogen atom, a trifluoromethyl, a $(C_1-C_4)$-alkyl, a $(C_1-C_4)$-alkoxy, a nitro, an amino and a hydroxyl, said substituents being identical or different;

R₂₉ is a hydrogen; a $(C_1-C_4)$-alkyl which is unsubstituted or substituted by a hydroxyl and/or by one, two or three fluorine atoms; a $(C_3-C_6)$-cycloalkyl; a $(C_1-C_5)$-alkoxy (only if W₃ is an oxygen atom); a $(C_3-C_6)$-cycloalkoxy (only if W₃ is an oxygen atom); a group —NR₃₁R₃₂ containing from zero to seven carbon atoms, R₂₉ being other than an unsubstituted $(C_1-C_4)$-alkyl if W₃ is an oxygen atom and simultaneously R₂₈ is a phenyl which is unsubstituted or substituted one or more times by a substituent selected from a halogen atom, a nitro, a hydroxyl, a trifluoromethyl, a $(C_1-C_4)$-alkyl and a $(C_1-C_4)$-alkoxy, said substituents being identical or different; a pyridyl; a pyrimidyl; or an imidazolyl which is unsubstituted or substituted by a $(C_1-C_4)$-alkyl;

or alternatively R₂₈ and R₂₉ together form a divalent hydrocarbon group L, in which the 1-position is bonded to the carbon atom carrying the substituent W₃, the divalent hydrocarbon group L being selected from a trimethylene, a cis-propenylene, a tetramethylene, a cis-butenylene, a cis-but-3-enylene, a cis,cis-butadienylene, a pentamethylene and a cis-pentenylene, said divalent hydrocarbon group L being unsubstituted or substituted by one or two methyls; and $R_{31}$ and $R_{32}$ are each independently a hydrogen, a $(C_1-C_5)$-alkyl or a $(C_3-C_6)$-cycloalkyl; or alternatively $R_{31}$ and $R_{32}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$-alkyl;

v—or a group $B_5$ of the formula

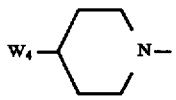

in which:

$W_4$ is a $(C_1-C_8)$-alkyl or a $(C_3-C_8)$-cycloalkyl, said alkyl and cycloalkyl groups being unsubstituted or substituted by one or more substituents selected from a halogen atom; a $(C_3-C_6)$-cycloalkyl; a cyano; a nitro; a hydroxyl; a $(C_1-C_4)$-alkoxy; a formyloxy; a $(C_1-C_4)$-alkylcarbonyloxy; an arylcarbonyl; a heteroarylcarbonyl; an oxo; an imino which is unsubstituted or substituted on the nitrogen atom by a $(C_1-C_6)$-alkyl, a $(C_3-C_6)$-cycloalkyl, a formyl, a $(C_1-C_4)$-alkylcarbonyl or an arylcarbonyl; a hydroxyimino which is unsubstituted or substituted on the oxygen atom by a $(C_1-C_4)$-alkyl or a phenyl; a group —$NR_{33}R_{34}$ containing from zero to seven carbon atoms; a group —$NR_{35}R_{36}$; a group —$C(=NR_{37})NR_{38}R_{39}$, in which the group —$NR_{38}R_{39}$ contains from zero to seven carbon atoms; or a group —$CON(OR_{40})R_{41}$, said substituents being identical or different;

$R_{33}$ and $R_{34}$ are each independently a hydrogen, a $(C_1-C_5)$-alkyl or a $(C_3-C_6)$-cycloalkyl; or alternatively $R_{33}$ and $R_{34}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a methyl or an ethyl;

$R_{35}$ is a hydrogen or a $(C_1-C_4)$-alkyl;

$R_{36}$ is a formyl; a $(C_1-C_4)$-alkylcarbonyl; an arylcarbonyl; a heteroarylcarbonyl; or a group —$C(=W_5)NR_{38}R_{39}$, in which the group —$NR_{38}R_{39}$ contains from zero to seven carbon atoms;

$W_5$ is an oxygen atom, a sulfur atom, a group —$NR_{37}$ or a group —$CHR_{42}$;

$R_{37}$ is a hydrogen or a $(C_1-C_4)$-alkyl; or alternatively $R_{37}$ and $R_{39}$ together form an ethylene group or a trimethylene group;

$R_{38}$ and $R_{39}$ are each independently a hydrogen, a $(C_1-C_5)$-alkyl or a $(C_3-C_6)$-cycloalkyl; or alternatively $R_{38}$ and $R_{39}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$-alkyl; or alternatively $R_{38}$ is a hydrogen or a $(C_1-C_4)$-alkyl and $R_{39}$ and $R_{37}$ together form an ethylene group or a trimethylene group;

$R_{40}$ and $R_{41}$ are each independently a $(C_1-C_3)$-alkyl;

$R_{42}$ is a cyano, a nitro or a group $SO_2R_{43}$; and $R_{43}$ is a $(C_1-C_4)$-alkyl or a phenyl;

and if $W_4$ is a cyclic group or if a substituent of $W_4$ is a cyclic group or contains a cyclic group, said cyclic groups can additionally be substituted on a carbon atom by one or more $(C_1-C_3)$-alkyls, and if a substituent of $W_4$ contains an aryl group or a heteroaryl group, said aryl or heteroaryl groups can additionally be monosubstituted or polysubstituted by a substituent selected from a halogen atom, a $(C_1-C_4)$-alkyl, a $(C_1-C_4)$-alkoxy, a cyano, a trifluoromethyl and a nitro, said substituents being identical or different;

vi—or a group $B_6$ of the formula

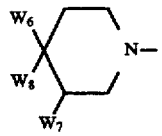

in which:

$W_6$ and $W_7$ are each a hydrogen, or alternatively $W_6$ is a hydrogen and $W_7$ is a hydroxyl;

$W_8$ is an aryl or a heteroaryl which is unsubstituted or substituted by an aryl, an arylcarbonyl, a heteroaryl or a heteroarylcarbonyl, said aryl or heteroaryl groups can additionally be monosubstituted or polysubstituted on the aromatic or heteroaromatic moiety and on a carbon atom by a substituent selected from a halogen atom; a cyano; a trifluoromethyl; a nitro; a hydroxyl; a $(C_1-C_5)$-alkoxy; a formyloxy; a $(C_1-C_4)$-alkylcarbonyloxy; a group —$NR_{33}R_{34}$ containing from zero to seven carbon atoms; a group —$NR_{35}R_{36}$; a group —$C(=NR_{37})NR_{38}R_{39}$, in which the group —$NR_{38}R_{39}$ contains from zero to seven carbon atoms; a group —$COOR_{44}$; a group —$CONR_{45}R_{46}$, in which the group $NR_{45}R_{46}$ contains from zero to seven carbon atoms; a mercapto; a group —$S(O)_xR_{47}$; a $(C_1-C_5)$-alkyl; a formyl; and a $(C_1-C_4)$-alkylcarbonyl, said substituents being identical or different; if $W_6$ and $W_7$ are each a hydrogen, $W_8$ is other than a phenyl which is unsubstituted or substituted one or more times by a substituent selected from a halogen atom, a nitro, a hydroxyl, a trifluoromethyl and a $(C_1-C_4)$-alkoxy, said substituents being identical or different; other than a pyridyl; other than a pyrimidyl; or other than an imidazolyl which is unsubstituted or substituted by a $(C_1-C_4)$-alkyl;

or alternatively $W_7$ is a hydrogen and $W_6$ and $W_8$, together with a diradical $W_9$ and the carbon atom of the piperidine to which they are bonded, form a spiro ring in which $W_8$ is a phenyl substituted in the ortho-position by a diradical $W_9$, which is itself joined to $W_6$, said phenyl being unsubstituted or substituted by a substituent selected from a halogen atom, a $(C_1-C_3)$-alkyl, a $(C_1-C_3)$-alkoxy, a hydroxyl, a $(C_1-C_3)$-alkylthio, a $(C_1-C_3)$-alkylsulfinyl and a $(C_1-C_3)$-alkylsulfonyl; the diradical $W_9$ is a methylene, a carbonyl or a sulfonyl; and $W_6$ is an oxygen atom or a group —$NR_{48}$—, in which $R_{48}$ is a hydrogen or a $(C_1-C_3)$-alkyl;

$R_{33}$, $R_{34}$, $R_{35}$, $R_{36}$, $R_{37}$, $R_{38}$ and $R_{39}$ are as defined above for the group $B_5$;

$R_{44}$ is a hydrogen, a $(C_1-C_5)$-alkyl, an aryl, a heteroaryl, an arylmethyl or a heteroarylmethyl;

$R_{45}$ and $R_{46}$ are each independently a hydrogen, a $(C_1-C_5)$-alkyl or a $(C_3-C_6)$-cycloalkyl; or alternatively $R_{45}$ and $R_{46}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a ($C_1$–$C_4$)-alkyl;

s is zero, one or two; and $R_{47}$ is a ($C_1$–$C_6$)-alkyl, a ($C_3$–$C_6$)-cycloalkyl, an aryl or a heteroaryl;

and if $W_8$ or a substituent of $W_8$ contains a cyclic group, said cyclic group can additionally be substituted by one or more methyls, and if a heteroaryl group forming part of $W_8$ or of a substituent of $W_8$ contains a nitrogen atom as the heteroatom, said nitrogen atom can additionally be substituted by a ($C_1$–$C_5$)-alkyl, and if $W_8$ or a substituent of $W_8$ contains a ($C_1$–$C_5$)-alkyl, ($C_1$–$C_5$)-alkoxy, formyl or ($C_1$–$C_4$)-alkylcarbonyl group, said ($C_1$–$C_5$)-alkyl, ($C_1$–$C_5$)-alkoxy, formyl or ($C_1$–$C_4$)-alkylcarbonyl groups can additionally be substituted by a hydroxyl, a ($C_1$–$C_3$)-alkoxy or one or more halogen atoms, with the proviso that a carbon atom bonded to a nitrogen atom or to an oxygen atom is not substituted by a hydroxyl or an alkoxy group, and with the proviso that a carbon atom in the α-position of a ($C_1$–$C_4$)-alkylcarbonyl group is not substituted by a chlorine, bromine or iodine atom;

vii—or a group $B_7$ of the formula

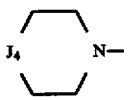

in which $J_4$ is:

vii$_1$—either a group

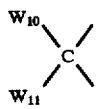

in which:

$W_{10}$ is a phenyl which is unsubstituted or monosubstituted to trisubstituted by a substituent selected from a halogen atom, a ($C_1$–$C_6$)-alkoxy, a ($C_1$–$C_6$)-alkyl and a trifluoromethyl, said substituents being identical or different; a benzyl which is unsubstituted or monosubstituted to trisubstituted by a substituent selected from a halogen atom, a ($C_1$–$C_6$)-alkoxy, a ($C_1$–$C_6$)-alkyl and a trifluoromethyl, said substituents being identical or different; a naphthyl which is unsubstituted or monosubstituted to trisubstituted by a substituent selected from a halogen atom, a ($C_1$–$C_6$)-alkoxy, a ($C_1$–$C_6$)-alkyl and a trifluoromethyl, said substituents being identical or different; a pyridyl which is unsubstituted or monosubstituted or disubstituted by a substituent selected from a halogen atom, a ($C_1$–$C_6$)-alkyl and a ($C_1$–$C_6$)-alkoxy, said substituents being identical or different; or a thienyl;

—$W_{11}$ is a group —CONHR$_{49}$; and

—$R_{49}$ is a group CH$_3$—CHOH—CH—COO—($C_1$–$C_6$)-alkyl, a group

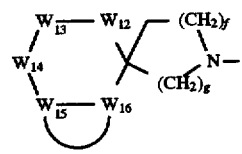

($C_1$–$C_6$)-alkyl-OCO—CH$_2$—CH$_2$—CH—COO—($C_1$–$C_6$)-alkyl
or a group —CH$_2$CH$_2$N(CH$_3$)$_2$;

vii$_2$—or a group

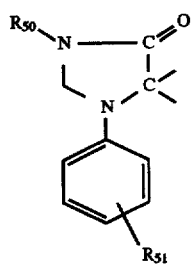

vii$_3$—or a group

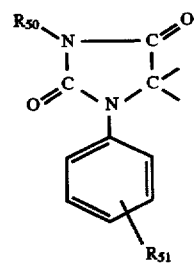

vii$_4$—or a group

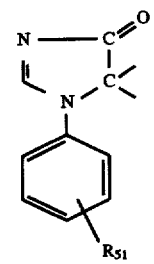

in which groups:

$R_{50}$ is a hydrogen, a ($C_1$–$C_6$)-alkyl or a benzyl; and $R_{51}$ is from one to three substituents selected from a hydrogen, a halogen atom, a trifluoromethyl, a ($C_1$–$C_6$)-alkyl and a ($C_1$–$C_6$)-alkoxy, said substituents being identical or different;

viii—or a group $B_8$ of the formula in which:

f and g are each independently zero, one, two, three, four or five, with the proviso that f+g is equal to one, two, three, four or five;

$W_{12}$ is a direct bond; a ($C_1$–$C_3$)-alkylene which is unsubstituted or substituted by an oxo, a group OR$_{52}$, a halogen, a trifluoromethyl or a phenyl which is itself unsubstituted or mono-, di- or tri-substituted by a substituent selected independently from a hydroxyl, a cyano, a halogen and a trifluoromethyl; a group —S(O)$_k$—; a group ($C_1$–$C_3$)-alkylene-S(O)$_k$—; a group —S(O)$_k$—($C_1$–$C_2$)-alkylene; a group —S(O)$_k$—NH—; a group —S(O)$_j$—NR$_{52}$—; a group —S(O)$_j$—

$NR_{52}$—$(C_1$–$C_2)$-alkylene; a group —$CONR_{52}$—; a group —$CONR_{52}$—$(C_1$–$C_2)$-alkylene; a group —COO—; or a group —COO—$(C_1$–$C_2)$-alkylene;

$W_{13}$ is a group —$NR_{53}$—, an oxygen atom, a sulfur atom, a sulfinyl or a sulfonyl, with the proviso that if $W_{12}$ is a direct bond and if $W_{14}$ is a $(C_1$–$C_3)$-alkylene, $W_{13}$ is a group —$NR_{53}$—;

$W_{14}$ is a direct bond; a $(C_1$–$C_3)$-alkylene which is unsubstituted or substituted by an oxo, a group $OR_{52}$, a halogen, a trifluoromethyl or a phenyl which is itself unsubstituted or mono-, di- or tri-substituted by a substituent selected independently from a group $OR_{52}$, a halogen and a trifluoromethyl; a group —$S(O)_k$—; a group $(C_1$–$C_3)$-alkylene-$S(O)_k$—; a group —$S(O)_k$—$(C_1$–$C_2)$-alkylene; a group —$NHS(O)_j$—; a group —NH—$(C_1$–$C_2)$-alkylene-$S(O)_j$—; a group —$S(O)_j$—$NR_{52}$—; a group —$S(O)_j$—$NR_{52}$—$(C_1$–$C_2)$-alkylene; a group —NHCO—$(C_1$–$C_2)$-alkylene; a group —$NR_{52}$—CO—; a group —$NR_{52}$—$(C_1$–$C_2)$-alkylene-CO—; a group —OCO—; or a group $(C_1$–$C_2)$-alkylene-OCO—;

$W_{15}$–$W_{16}$ together form two adjacent atoms of a cyclic radical of the formula

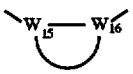

said cyclic radical being a phenyl, a naphthyl or a heteroaryl group selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidyl, a pyrrolyl, a quinolyl, a tetrazolyl, a thiadiazolyl, a thiazolyl, a thienyl and a triazolyl, and said phenyl, naphthyl or heteroaryl cyclic radical being unsubstituted or mono-, di- or tri-substituted by $R_{54}$;

k is zero, one or two;

j is one or two;

$R_{52}$ is a hydrogen; a $(C_1$–$C_6)$-alkyl which is unsubstituted or monosubstituted or disubstituted by a substituent selected independently from a hydroxyl, an oxo, a cyano, a halogen atom, a trifluoromethyl and a phenyl which is itself unsubstituted or substituted by a hydroxyl, a $(C_1$–$C_3)$-alkyl, a cyano, a halogen, a trifluoromethyl or a $(C_1$–$C_4)$-alkoxy; a phenyl, a pyridyl or a thiophene, said phenyl, pyridyl or thiophene being unsubstituted or mono-, di- or tri-substituted by a substituent selected independently from a hydroxyl, a $(C_1$–$C_4)$-alkyl, a cyano, a halogen atom and a trifluoromethyl; or a $(C_1$–$C_3)$-alkoxy;

$R_{53}$ is a hydrogen; a $(C_1$–$C_8)$-alkyl which is unsubstituted or monosubstituted or polysubstituted by a substituent selected from a group —$OR_{52}$, an oxo, a group —$NHCOR_{52}$, a group —$NR_{55}R_{56}$, a cyano, a halogen atom, a trifluoromethyl and a phenyl which is itself unsubstituted or substituted by a hydroxyl, a cyano, a halogen atom or a trifluoromethyl; a group —$S(O)R_{57}$; a group —$CO_2R_{57}$—; a group —$SO_2R_{57}$; a group —$COR_{57}$; or a group —$CONR_{56}R_{57}$;

$R_{54}$ is a hydrogen; a $(C_1$–$C_6)$-alkyl which is unsubstituted or monosubstituted or disubstituted by a hydrogen or a hydroxyl; an oxo; a group —$OR_{52}$; a halogen atom; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR_{55}S(O)_jR_{56}$; a group —$CONR_{55}R_{56}$; a group —$COR_{52}$; a group —$CO_2R_{52}$; a group —$S(O)_jR_{52}$; or a heteroaryl group, said heteroaryl being selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidinyl, a pyrrolyl, a quinolyl, a tetrazolyl, a thiadiazolyl, a thiazolyl, a thienyl and a triazolyl, and said heteroaryl being unsubstituted or monosubstituted or disubstituted by $R_{58}$;

$R_{55}$ is $R_{52}$;

$R_{56}$ is $R_{52}$;

or alternatively $R_{55}$ and $R_{56}$, together with the atoms to which they are bonded, form a five-, six- or seven-membered saturated monocyclic heterocycle containing one or two heteroatoms, said heteroatoms being selected independently from a nitrogen atom, an oxygen atom and a sulfur atom, said heterocycle being unsubstituted or monosubstituted or disubstituted by a substituent selected independently from a hydroxyl, an oxo, a cyano, a halogen atom and a trifluoromethyl;

$R_{57}$ is a $(C_1$–$C_6)$-alkyl which is unsubstituted or mono-e di- or tri-substituted by a substituent selected from a hydroxyl, an oxo, a cyano, a group —$OR_{52}$, a group —$NR_{55}R_{56}$, a group —$NR_{55}COR_{56}$, a halogen atom, a trifluoromethyl and a phenyl which is itself unsubstituted or mono-, di- or tri-substituted by a substituent selected independently from a hydroxyl, an oxo, a cyano, a group —$NHR_{52}$, a group —$NR_{55}R_{56}$, a group —$NR_{55}COR_{56}$, a halogen atom, a trifluoromethyl and a $(C_1$–$C_3)$-alkyl; and $R_{58}$ is a hydrogen; a $(C_1$–$C_6)$-alkyl which is unsubstituted or monosubstituted or disubstituted by a hydrogen or a hydroxyl; an oxo; a group —$OR_{52}$; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR_{55}S(O)_jR_{56}$; a group —$CONR_{55}R_{56}$; a group —$COR_{52}$; a group —$CO_2R_{52}$; a group —$S(O)_jR_{52}$; or a phenyl;

and the group $B_8$ being other than the group $B_6$ if $W_7$ is a hydrogen and $W_6$ and $W_8$, together with a diradical $W_9$ and the carbon atom of the piperidine to which they are bonded, form a spiro ring;

or its salts, where appropriate, with mineral or organic acids.

2. An optically pure compound of the formula

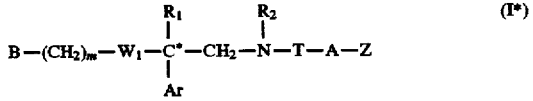

in which:

"*" denotes that the carbon atom carrying this label has the determined (+) or (−) absolute configuration; and $W_1$, B, m, Ar, $R_1$, $R_2$, T, A and Z are as defined in claim 1 for the compounds of formula (I), or a salt thereof, where appropriate, with mineral or organic acids.

3. A compound according to claim 1 of formula (I) in which:

Z is Z' and is:
a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a $(C_1$–$C_4)$-alkyl;

a benzylamino; a carboxyl; a ($C_1$–$C_{10}$)-alkyl; a ($C_3$–$C_8$)-cycloalkyl which is unsubstituted or monosubstituted or polysubstituted by a methyl; a ($C_1$–$C_{10}$)-alkoxy; a ($C_3$–$C_8$)-cycloalkoxy which is unsubstituted or monosubstituted or polysubstituted by a methyl; a mercapto; a ($C_1$–$C_{10}$)-alkylthio; a formyloxy; a ($C_1$–$C_6$)-alkylcarbonyloxy; a formylamino; a ($C_1$–$C_6$)-alkylcarbonylamino; a benzoylamino; a ($C_1$–$C_4$)-alkoxycarbonyl; a ($C_3$–$C_7$)-cycloalkoxycarbonyl; a carbamoyl which is unsubstituted or monosubstituted or disubstituted by a ($C_1$–$C_4$)-alkyl; a ureido which is unsubstituted or monosubstituted or disubstituted in the 3-position by a ($C_1$–$C_4$)-alkyl or a ($C_3$–$C_7$)-cycloalkyl; or a (pyrrolidin-1-yl)carbonylamino, said substituents being identical or different;

a naphthyl which is unsubstituted or monosubstituted or polysubstituted by a halogen, a trifluoromethyl, a ($C_1$–$C_4$)-alkyl, a hydroxyl or a ($C_1$–$C_4$)-alkoxy; or a pyridyl, a thienyl, an indolyl, a quinolyl, a benzothienyl or an imidazolyl.

4. A compound according to claim 3 of formula (I) in which simultaneously:

$R_1$ and $R_2$ together form a group —$(CH_2)_n$—CQ— in which n is equal to 2 and Q is $H_2$ or oxygen;

$W_1$ is an oxygen atom; and

Ar is a 3,4-dichlorophenyl or a 3,4-difluorophenyl;

or pharmaceutically acceptable salts and solvates thereof.

5. A compound according to claim 3 of formula (I) in which simultaneously:

$R_1$ is hydrogen;

$R_2$ is a methyl group;

$W_1$ is an oxygen atom;

m is equal to 2; and

Ar is a 3,4-dichlorophenyl or a 3,4-difluorophenyl;

or pharmaceutically acceptable salts and solvates thereof.

6. A compound according to claim 3 of formula (I) in which simultaneously:

$R_1$ is hydrogen;

$R_2$ is a methyl group;

$W_1$ is a group an a —NR— in which R is a methyl group;

Ar is a 3,4-dichlorophenyl or a 3,4-difluorophenyl;

or pharmaceutically acceptable salts and solvates thereof.

7. A compound according to claim 3 selected from:

4-phenyl-1-[2-[3-(3,4-dichlorophenyl)-1-(3-isopropoxybenzylcarbonyl)piperid-3-yloxy]ethyl]quinuclidinium chloride;

4-phenyl-4-propionyloxy-1-[2-[3-(3,4-dichlorophenyl)-1-benzoylpiperid-3-yloxy]ethyl]piperidine hydrochloride;

4-acetamido-4-phenyl-1-[2-[1-(3,4-dichlorophenyl)-2-(N-methyl-N-benzyloxycarbonylamino)ethoxy]ethyl]piperidine hydrochloride;

4-acetamido-4-phenyl-1-[2-[1-(3,4-dichlorophenyl)-2-(N-methyl-N-phenylcarbonylamino)ethoxy]ethyl]piperidine hydrochloride;

4-benzyl-1-[2-[3-(3,4-dichlorophenyl)-1-(3-isopropoxybenzylcarbonyl)piperid-3-yloxy]ethyl]quinuclidinium chloride; and 4-phenyl-1-[2-[N-methyl-N-[1-(3,4-dichlorophenyl)-2-[N'-methyl-N'-(3-isopropoxybenzylcarbonyl)amino]ethyl]amino]ethyl]quinuclidinium chloride hydrochloride.

8. A method of obtaining a compound according to claim 1 of formula (I) in which $R_1$ and $R_2$ together form a group —$(CH_2)_n$—CQ in which Q is oxygen, and $W_1$ is an oxygen atom, which consists in:

1) treating a compound of formula (II):

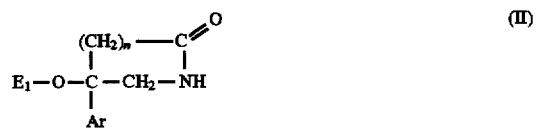

in which Ar is as defined above and $E_1$ is an O-protecting group, in particular the tetrahydropyran-2-yl group, with a halogenated derivative of the formula

in which Hal is a halogen atom and A and Z are as defined in claim 1, in the presence of a base such as, for example, sodium hydride or potassium tert-butylate, in order to form the compound of the formula

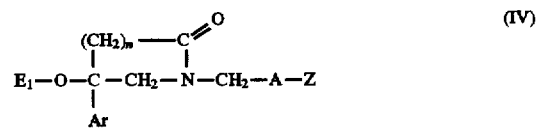

2) eliminating the protecting group $E_1$ by reaction with an acid;

3) treating the resulting compound of formula (V):

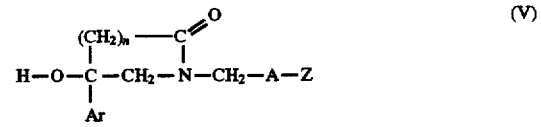

with a compound of formula (VI): Hal-$(CH_2)_m$—O—$E_2$, in which $E_2$ is an O-protecting group such as the tetrahydropyran-2-yl group, and m is as defined for (I) in claim 1, in order to form the compound of formula (VII):

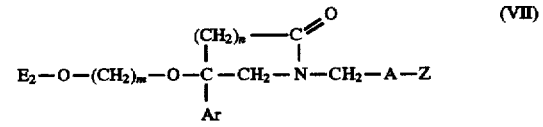

in which $E_2$, m, Ar, T, A and Z are as defined for (I) in claim 1;

4) eliminating the protecting group $E_2$ by reaction with an acid;

5) treating the resulting compound of formula (VIII):

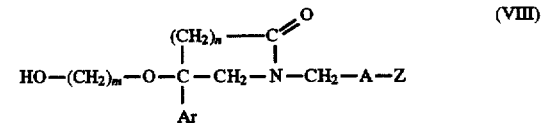

with a compound of the formula

in which G is a methyl, phenyl, tolyl or trifluoromethyl group;

6) reacting the resulting sulfonate of the formula

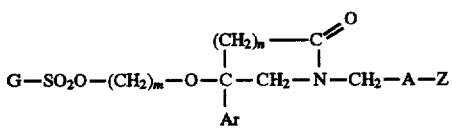   (IX)

either with a cyclic secondary amine of the formula

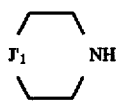   (Xa)

in which

J'$_1$ is:
either a group

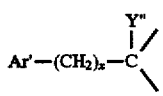

in which Ar' and x are as defined for (I) in claim 1 and Y" is either Y' as defined for (I) in claim 1, or a precursor of Y', it being understood that if Y" contains a hydroxyl or an amino group, these groups can be protected;
or a group

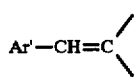

in which
Ar' is as defined for (I) in claim 1;
or a group

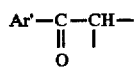

in which
Ar' is as defined for (I) in claim 1;
or a group

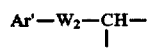

in which
Ar' and W$_2$ are as defined for (I) in claim 1;
or with a cyclic tertiary amine of the formula

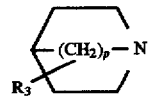   (Xb)

in which
p and R$_1$ are as defined above for a compound of formula (I) in claim 1;

or with a cyclic secondary amine of the formula

   (Xc)

in which
J$_2$ is as defined for (I) in claim 1;
or with a cyclic secondary amine of the formula

   (Xd)

in which
J$_3$ is as defined for (I) in claim 1;
or with a cyclic secondary amine of the formula

   (Xe)

in which
W$_4$ is as defined for (I) in claim 1;
or with a cyclic secondary amine of the formula

   (Xf)

in which
W$_6$, W$_7$ and We are as defined for (I) in claim 1;
or with a cyclic secondary amine of the formula

   (Xg)

in which
J$_4$ is as defined for (I) in claim 1;
or with a compound of the formula

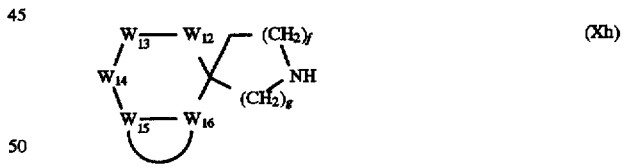   (Xh)

in which f, g, W$_{12}$, W$_{13}$, W$_{14}$, W$_{15}$ and W$_{16}$ are as defined for (I) in claim 1; and 7)—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 6) to a salt thereof with a mineral or organic acid;
or, in the case where a cyclic tertiary amine of formula (Xb) has been used, isolating the product thus obtained in step 6) or optionally exchanging the sulfonate anion of the resulting quaternary salt with another pharmaceutically acceptable anion.

9. A method of obtaining a compound according to claim 1 of formula (I) in which simultaneously R$_1$ and R$_2$ together form a group —$(CH_2)_n$—CQ— where Q=$H_2$ and n=1, 2 or 3, or alternatively $R_1$ and $R_2$ are separate and are as defined for the compound (I) in claim 1, $W_1$ is an oxygen atom and B is B', i.e. one of the groups $B_2$, $B_3$, $B_4$, $B_5$, $B_6$, $B_7$ or $B_8$ as defined for a compound of formula (I) in claim 1, which consists in:

1) eliminating the O-protecting group $E_1$ from a compound of the formula

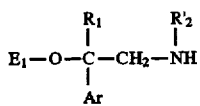
(XI)

in which $R_1$ and Ar are as defined for a compound of formula (I), $R'_2$ is a hydrogen, a $(C_1-C_7)$-alkyl, an ω-$(C_1-C_4)$-alkoxy-$(C_2-C_4)$-alkylene, an ω-hydroxy-$(C_2-C_4)$-alkylene, an ω-$(C_1-C_4)$-alkylthio-$(C_2-C_4)$-alkylene, an ω-$(C_1-C_4)$-alkoxycarbonyl-$(C_2-C_4)$-alkylene, an ω-carboxy-$(C_2-C_4)$-alkylene, an ω-$(C_1-C_4)$-alkylcarbonyl-$(C_2-C_4)$-alkylene, an ω-$R_6R_7$NCO—$(C_2-C_4)$-alkylene, in which $R_6$ and $R_7$ are as defined for (I) in claim 1, or an ω-cyano-$(C_1-C_3)$-alkylene, or $R_1$ and $R'_2$ together form a group —$(CH_2)_n$—CQ— (n=1, 2 or 3 and Q=$H_2$), and $E_1$ is an O-protecting group, in particular the tetrahydropyran-2-yl group, by reaction with an acid;

2) protecting the amine group of the resulting compound of the formula

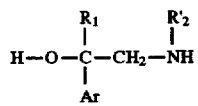
(XII)

for example by reaction with di-tert-butyl dicarbonate ($Boc_2O$) in a solvent such as dioxane, to give the compound of the formula

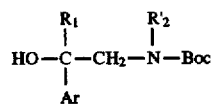
(XIII)

3) if appropriate, if $R'_2$ in the compound of formula (XI) is an ω-hydroxy-$(C_2-C_4)$-alkylene, protecting the amine group as indicated in step 2) and then protecting the hydroxyl, or optionally converting the group $R'_2$ to $R''_2$ to give a compound of the formula

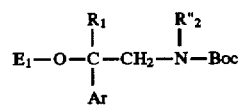
(XIV)

in which $E_1$, $R_1$ and Ar are as defined above and $R''_2$ is an ω-$(C_1-C_4)$-alkylcarbonyloxy-$(C_2-C_4)$-alkylene, an ω-benzoyloxy-$(C_2-C_4)$-alkylene, an ω-benzyloxy-$(C_2-C_4)$-alkylene, an ω-formyloxy-$(C_2-C_4)$-alkylene, an ω-$R_5$NHCOO—$(C_2-C_4)$-alkylene, an ω-$R_8R_9$N—$(C_2-C_4)$-alkylene, an ω-$R_{10}$CONR$_{11}$—$(C_2-C_4)$-alkylene, an ω-$R_{12}$OCONR$_{11}$—$(C_2-C_4)$-alkylene, an ω-$R_6R_7$NCONR$_{11}$—$(C_2-C_4)$-alkylene or an ω-$R_{13}SO_2NR_{11}$—$(C_2-C_4)$-alkylene, in which $R_5$ to $R_{13}$ are as defined for (I) in claim 1, and then selectively eliminating the protecting group $E_1$ by acid hydrolysis to give the compound of the formula

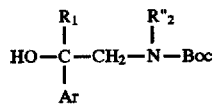
(XIIIbis)

4) treating the compound (XIII) or (XIIIbis) obtained in step 2) or in step 3), it being understood that if $R'_2$ is an ω-hydroxy-$(C_2-C_4)$-alkylene, the hydroxyl is protected, or if $R''_2$ is a group ω-$R_8R_9$N—$(C_2-C_4)$-alkylene in which $R_8$ is a hydrogen, the amine is protected, with a compound of formula (VI): Hal-$(CH_2)_m$—O—$E_2$, in which $E_2$ is an O-protecting group such as the tetrahydropyran-2-yl group, in order to form the compound of the formula

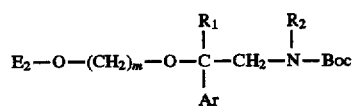
(XV)

in which $E_2$, m, Ar and $R_1$ are as defined above and $R_2$ is as defined for a compound of formula (I);

5) selectively eliminating the protecting group $E_2$, for example by reaction with pyridinium paratoluenesulfonate if $E_2$ is a tetrahydropyran-2-yl, to give a compound of the formula

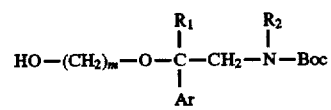
(XVI)

6) treating the compound (XVI), it being understood that if $R_2$ is an ω-hydroxy-$(C_2-C_4)$-alkylene, the hydroxyl is protected, or if $R''_2$ is a group ω-$R_8R_9$N—$(C_2-C_4)$-alkylene in which $R_8$ is a hydrogen, the amine is protected, with a compound of formula (XXIX) as defined in claim 8, to give the sulfonate of the formula

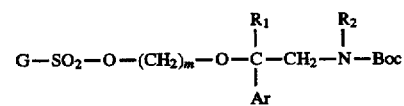
(XVII)

7) reacting the compound (XVII) with a compound of formula (Xa), (Xc), (Xd), (Xe), (Xf), (Xg) or (Xh) as defined in claim 8, and optionally converting Y'" to Y', to give the compound of the formula

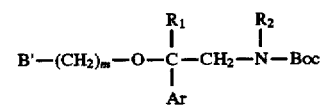
(XVIII)

in which B' is a group $B_2$, $B_3$, $B_4$, $B_5$, $B_6$, $B_7$ or $B_8$ as defined above for a compound of formula (I);

8) deprotecting the N-protecting group of the compound (XVIII) by treatment in a strong acid medium, for example HCl, to give the compound of the formula

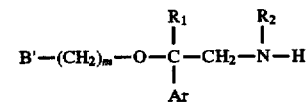
(XIX)

9) reacting the compound of formula (XIX) either with a halogenated derivative of the formula Hal—CH$_2$—A—Z  (III)

in which Hal is a halogen atom and A and Z are as defined above, if R$_1$ and R$_2$ are separate and if it is intended to prepare a compound of formula (I) in which T is —CH$_2$—;

or with a functional derivative of an acid of the formula

HO—CO—A—Z  (IIIa)

in which A and Z are as defined above, if it is intended to prepare a compound of formula (I) in which T is —CO—;

or with a chloroformate of the formula

Cl—COO—A—Z  (IIIb)

in which A and Z are as defined above, if it is intended to prepare a compound of formula (I) in which T is —COO—;

or with an isocyanate of the formula

O=C=N—A—Z  (IIIc)

in which A and Z are as defined above, if it is intended to prepare a compound of formula (I) in which T is a group —CO—NR$_4$— in which R$_4$ is a hydrogen;

or with a carbamoyl chloride of the formula $$\text{Cl—CO—N(R'}_4\text{)—A—Z}$$  (IIId)

in which A and Z are as defined above and R'$_4$ is a (C$_1$–C$_4$)-alkyl group, if it is intended to prepare a compound of formula (I) in which T is —CO—NR$_4$— in which R$_4$ is a (C$_1$–C$_4$)-alkyl; and 10) after deprotection of the hydroxyl or amino groups, if appropriate, or optional conversion of Y" to Y', optionally converting the product obtained in step 9) to a salt thereof with a mineral or organic acid.

10. A method of obtaining a compound according to claim 1 of formula (I) in which simultaneously R$_1$ and R$_2$ together form a group —(CH$_2$)$_n$—CQ— in which Q=H$_2$ and n=1, 2 or 3, or alternatively R$_1$ and R$_2$ are separate and are as defined for the compound (I) in claim 1, W$_1$ is an oxygen atom and B is as defined for a compound of formula (I) in claim 1, characterized in that:

1') the protecting group E$_2$ and the N-protecting group of the compound (XV) as defined in claim 9 are eliminated simulataneously, it being understood that if R$_2$ is an ω-hydroxy-(C$_2$–C$_4$)-alkylene in which the hydroxyl is protected, the latter is not affected under the operating conditions, or if R$_2$ is a group ω-R$_8$R$_9$N—(C$_2$–C$_4$)-alkylene in which R$_8$ is hydrogen and R$_9$ is as defined for (I) in claim 1, the amine is protected, the latter is not affected under the operating conditions, by treatment in a strong acid medium, for example with HCl, to give the compound of the formula $$\text{HO—(CH}_2\text{)}_m\text{—O—C(R}_1\text{)(Ar)—CH}_2\text{—NH—R}_2$$  (XX)

in which m, Ar, R$_1$ and R$_2$ are as defined above for (I) in claim 1;

2') the compound (XX) is treated with one of the compounds (III), (IIIa), (IIIb), (IIIc) or (IIId) as defined in claim 9, to give the compound of the formula $$\text{HO—(CH}_2\text{)}_m\text{—O—C(R}_1\text{)(Ar)—CH}_2\text{—N(R}_2\text{)—T—A—Z}$$  (XXI)

in which m, Ar, R$_1$, R$_2$, T, A and Z are as defined above;

3') the compound (XXI) is treated, it being understood that if R$_2$ is an ω-hydroxy-(C$_2$–C$_4$)-alkylene, the hydroxyl is protected, or if R$_2$ is a group ω-R$_8$R$_9$N—(C$_2$–C$_4$)-alkylene in which R$_8$ is a hydrogen and R$_9$ is as defined above, the amine is protected, with the compound of formula (XXIX) as defined in claim 8, to give the compound of the formula $$\text{G—SO}_2\text{—O—(CH}_2\text{)}_m\text{—O—C(R}_1\text{)(Ar)—CH}_2\text{—N(R}_2\text{)—T—A—Z}$$  (XXII)

4') the compound (XXII) is reacted with one of the compounds (Xa), (Xb), (Xc), (Xd), (Xe), (Xf), (Xg) or (Xh) as defined in claim 8; and 5')—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', the product obtained in step 4') is optionally converted to a salt thereof with a mineral or organic acid;

or, in the case where a cyclic tertiary amine of formula (Xb) has been used and after deprotection of the hydroxyl or amino groups, the product thus obtained in step 4') is isolated or the sulfonate anion of the resulting quaternary salt is optionally exchanged with another pharmaceutically acceptable anion.

11. A method according to claim 9, applicable to the condition that T is other than —CO—NH— or that —T—A— is other than —CO—(CH$_2$)$_r$—, characterized in that:

1") a compound of formula (XI) as defined in claim 9 is treated with one of the compounds of formula (III), (IIIa), (IIIb) or (IIId) as defined in claim 9, to give a compound of the formula $$\text{E}_1\text{—O—C(R}_1\text{)(Ar)—CH}_2\text{—N(R'}_2\text{)—T—A—Z}$$  (XXIII)

in which E$_1$, Ar, R$_1$, R'$_2$, T, A and Z are as defined in claim 9;

2") if appropriate, if R'$_2$ is an ω-hydroxy-(C$_2$–C$_4$)-alkylene, the hydroxyl is protected, or the group R'$_2$ is optionally converted to R"$_2$, to give a compound of the formula $$\text{E}_1\text{—O—C(R}_1\text{)(Ar)—CH}_2\text{—N(R"}_2\text{)—T—A—Z}$$  (XXIIIbis)

in which E$_1$, Ar, R$_1$, T, A and Z are as defined above and R"$_2$ is an ω-(C$_1$–C$_4$)-alkylcarbonyloxy-(C$_2$–C$_4$)-alkylene, an ω-benzoyloxy-(C$_2$–C$_4$)-alkylene, an ω-benzyloxy-(C$_2$–C$_4$)-alkylene, an ω-formyloxy-(C$_2$–C$_4$)-alkylene, an ω-R$_5$NHCOO—(C$_2$–C$_4$)- alkylene, an ω-R$_8$R$_9$N—(C$_2$-C$_4$)-alkylene, an
ω-R$_{10}$CONR$_{11}$—(C$_2$-C$_4$)alkylene, an
ω-R$_{12}$OCONR$_{11}$—(C$_2$-C$_4$)-alkylene, an
ω-R$_6$R$_7$NCONR$_{11}$—(C$_2$-C$_4$)-alkylene or an
ω-R$_{13}$SO$_2$NR$_{11}$—(C$_2$-C$_4$)-alkylene, in which R$_5$ to R$_{13}$ are as defined for (I) in claim 1;

3") the protecting group E$_1$ is selectively eliminated from the compound (XXIII) or (XXIIIbis) by reaction with an acid in order to form the compound of the formula

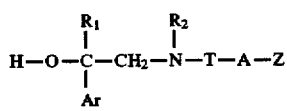
(XXIV)

4") the resulting compound (XXIV) is treated, it being understood that if R$_2$ is an ω-hydroxy-(C$_2$-C$_4$)-alkylene, the hydroxyl is protected, or if R$_2$ is a group ω-R$_8$R$_9$N—(C$_2$-C$_4$)-alkylene in which R$_8$ is a hydrogen and R$_9$ is as defined above, the amine is protected, with a compound of formula (VI): Hal-(CH$_2$)$_m$—O—E$_2$, in which E$_2$ is an O-protecting group such as the tetrahydropyran-2-yl group, to give the compound of the formula

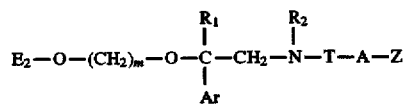
(XXV)

5") the protecting group E$_2$ is selectively eliminated by reaction with an acid to give the compound of the formula

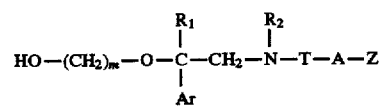
(XXVI)

6") the compound (XXVI) is treated, it being understood that if R$_2$ is an ω-hydroxy-(C$_2$-C$_4$)-alkylene, the hydroxyl is protected, or if R$_2$ is an ω-R$_8$R$_9$N—(C$_2$-C$_4$)-alkylene in which R$_8$ is hydrogen and R$_9$ is as defined above, the amine is protected, with the compound of formula (XXIX) as defined in claim 8, in order to form the compound of the formula

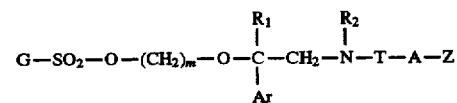
(XXVII)

7") the resulting compound (XXVII) is reacted with one of the compounds (Xa), (Xb), (Xc), (Xd), (Xe), (Xf), (Xg) or (Xh) as defined in claim 8; and 8")—either, in the case where a cyclic secondary amine of formula (Xa), (Xc), (Xd), (Xe), (Xf), (Xg) or (Xh) has been used and after deprotection of the hydroxyl or amino groups, if appropriate, or optional conversion of Y" to Y', the product obtained in step 7") is optionally converted to a salt thereof with a mineral or organic acid;

or, in the case where a cyclic tertiary amine of formula (Xb) has been used and after deprotection of the hydroxyl or amino group, if appropriate, the product thus obtained in step 7") is isolated or the sulfonate anion of the resulting quaternary salt is optionally exchanged with a pharmaceutically acceptable anion.

12. A method of obtaining a compound of formula (I) according to claim 1 in which simultaneously R$_1$ and R$_2$ together form a group —(CH$_2$)$_n$—CQ— in which Q is oxygen, and W$_1$ is a group —NR— as defined for (I), which consists in:

1) treating a compound of the formula

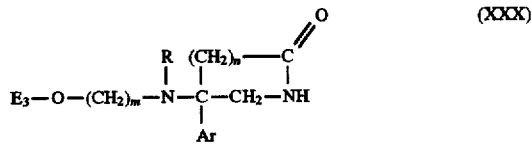
(XXX)

in which m, R and Ar are as defined in claim 1 for a compound of formula (I) and E$_3$ is an O-protecting group, in particular the tetrahydropyran-2-yl group, with a halogenated derivative of the formula Hal-CH$_2$—A—Z (III)

in which Hal is a halogen atom and A and Z are as defined for a compound of formula (I) in claim 1, if it is intended to prepare a compound of formula (I) in which T is —CH$_2$—, in the presence of a base such as sodium hydride or potassium tert-butylate, in order to form the compound of the formula

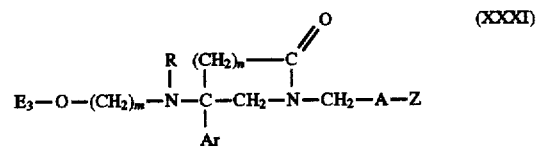
(XXXI)

2) eliminating the protecting group E$_3$ by reaction with an acid;

3) treating the resulting compound of the formula

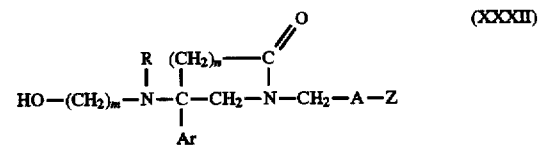
(XXXII)

with a compound of the formula

G—SO$_2$—Cl (XXIX)

in which G is a methyl, phenyl, tolyl or trifluoromethyl group;

4) reacting the resulting sulfonate of the formula

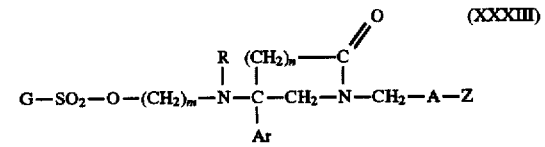
(XXXIII)

with one of the compounds of formula (Xa), (Xb), (Xc), (Xd), (Xe), (Xf), (Xg) or (Xh) as defined above in claim 8; and 5)—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 4) to a salt thereof with a mineral or organic acid;

or, in the case where a cyclic tertiary amine of formula (Xb) has been used, isolating the product thus obtained in step 4) or optionally exchanging the sulfonate anion of the resulting quaternary salt with another pharmaceutically acceptable anion.

13. A method of obtaining a compound of formula (I) according to claim 1 in which simultaneously $R_1$ and $R_2$ together form a group $-(CH_2)_n-CQ-$ in which $Q=H_2$ and $n=1$, 2 or 3, or alternatively $R_1$ and $R_2$ are separate and are as defined for the compound (I) in claim 1, $W_1$ is a group $-NR-$ and B is as defined for a compound of formula (I) in claim 1, which consists in:

1) treating a compound of the formula

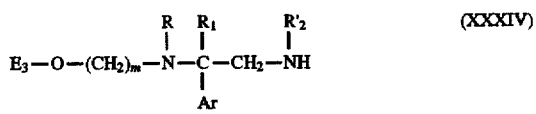

in which m, R, Ar and $R_1$ are as defined in claim 1 for a compound of formula (I), $R'_2$ is a hydrogen, a $(C_1-C_7)$-alkyl, an $\omega$-$(C_1-C_4)$-alkoxy-$(C_2-C_4)$-alkylene, an $\omega$-hydroxy-$(C_2-C_4)$-alkylene, an $\omega$-$(C_1-C_4)$-alkylthio-$(C_2-C_4)$-alkylene, an $\omega$-$(C_1-C_4)$-alkoxycarbonyl-$(C_2-C_4)$-alkylene, an $\omega$-carboxy-$(C_2-C_4)$-alkylene, an $\omega$-$(C_1-C_4)$-alkylcarbonyl-$(C_2-C_4)$-alkylene, an $\omega$-$R_6R_7NCO$-$(C_2-C_4)$-alkylene, in which $R_6$ and $R_7$ are as defined for the compound of formula (I) in claim 1, or an $\omega$-cyano-$(C_1-C_3)$-alkylene, or alternatively $R_1$ and $R'_2$ together form a group $-(CH_2)_n-CQ-$ ($n=1$, 2 or 3 and $Q=H_2$), and $E_3$ is an O-protecting group, in particular the tetrahydropyran-2-yl group, either with a halogenated derivative of the formula

in which Hal is a halogen atom and A and Z are as defined for (I) in claim 1, if $R_1$ and $R_2$ are separate and if it is intended to prepare a compound of formula (I) in which T is $-CH_2-$;

or with a functional derivative of an acid of the formula

in which A and Z are as defined above, if it is intended to prepare a compound of formula (I) in which T is $-CO-$;

or with a chloroformate of the formula

in which A and Z are as defined above, if it is intended to prepare a compound of formula (I) in which T is $-COO-$;

or with an isocyanate of the formula

in which A and Z are as defined above, if it is intended to prepare a compound of formula (I) in which T is a group $-CO-NR_4-$ in which $R_4$ is a hydrogen;

or with a carbamoyl chloride of the formula

in which A and Z are as defined above and $R'_4$ is a $(C_1-C_4)$-alkyl group, if it is intended to prepare a compound of formula (I) in which T is $-CO-NR_4-$ in which $R_4$ is a $(C_1-C_4)$-alkyl, to give a compound of the formula

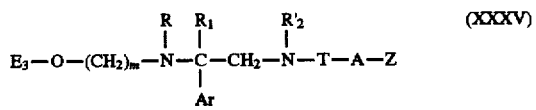

2) if appropriate, if $R'_2$ is an $\omega$-hydroxy-$(C_2-C_4)$-alkylene, protecting the hydroxyl, or optionally converting the group $R'_2$ to $R''_2$, to give a compound of the formula

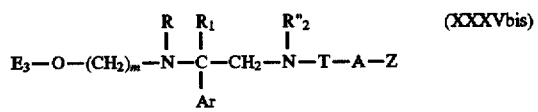

in which $E_3$, m, R, $R_1$, Ar, T, A and Z are as defined above and $R''_2$ is an $\omega$-$(C_1-C_4)$-alkylcarbonyloxy-$(C_2-C_4)$-alkylene, an $\omega$-benzoyloxy-$(C_2-C_4)$-alkylene, a $\omega$ benzyloxy-$(C_2-C_4)$-alkylene, an $\omega$-formyloxy-$(C_2-C_4)$-alkylene, an $\omega$-$R_5NHCOO$-$(C_2-C_4)$-alkylene, an $\omega$-$R_8R_9N$-$(C_2-C_4)$-alkylene, an $\omega$-$R_{10}CONR_{11}$-$(C_2-C_4)$-alkylene, an $\omega$-$R_{12}OCONR_{11}$-$(C_2-C_4)$-alkylene, an $\omega$-$R_6R_7NCONR_{11}$-$(C_2-C_4)$-alkylene or an $\omega$-$R_{13}SO_2NR_{11}$-$(C_2-C_4)$-alkylene, in which $R_5$ to $R_{13}$ are as defined for the compound of formula (I) in claim 1;

3) selectively eliminating the protecting group $E_3$ from the compound (XXXV) or (XXXVbis) by reaction with an acid to give a compound of the formula

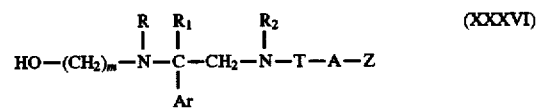

4) if appropriate, eliminating the protecting group $E_3$ from a compound of formula (XXXIV) by reaction with an acid to give a compound of the formula

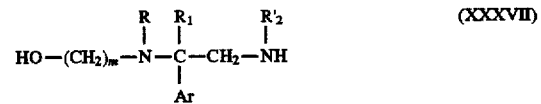

in which m, R, Ar, $R_1$ and $R'_2$ are as defined above, and then treating the compound (XXXVII) with one of the compounds (III), (IIIa), (IIIb), (IIIc) or (IIId) as defined in claim 9, to give the compound of the formula

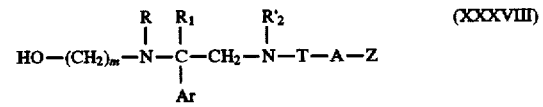

in which m, R, Ar, T, A, Z, $R_1$ and $R'_2$ are as defined above;

5) treating the compound (XXXVI) or (XXXVIII), it being understood that if $R_2$ or $R'_2$ is an $\omega$-hydroxy-$(C_2-C_4)$-alkylene, the hydroxyl is protected, or if $R_2$ is an $\omega$-$R_8R_9N$-$(C_2-C_4)$-alkylene in which $R_8$ is hydrogen and $R_9$ is as defined above, the amine is protected, with a compound of formula (XXIX) as defined in claim 12, to give a compound of the formula

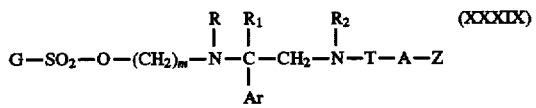

6) reacting the resulting sulfonate with one of the compounds (Xa), (Xb), (Xc), (Xd), (Xe), (Xf), (Xg) or (Xh) as defined in claim 8; and 7)—either, in the case where a cyclic secondary amine of formula (Xa), (Xc), (Xd), (Xe), (Xf) or (Xg) or a compound of formula (Xh) has been used and after deprotection of the hydroxyl or amino groups, if appropriate, or optional conversion of Y" to Y', optionally converting the product obtained in step 6) to a salt thereof with a mineral or organic acid;

or, in the case where a cyclic tertiary amine of formula (Xb) has been used, isolating the product thus obtained in step 6) or optionally exchanging the sulfonate anion of the resulting quaternary salt with another pharmaceutically acceptable anion.

14. A method according to claim 13 for the preparation of a compound (I) according to claim 1 in which B is B', i.e. one of the groups $B_2$, $B_3$, $B_4$, $B_5$, $B_6$, $B_7$ or $B_8$ as defined for (I) in claim 1, characterized in that:

1') the O-protecting group $E_3$ is eliminated from the compound of formula (XXXIV) to give the compound of formula (XXXVII) as defined in claim 13;

2') the amine group of the compound of formula (XXXVII) is protected by reaction for example with di-tert-butyl dicarbonate ($Boc_2O$) in a solvent such as dioxane to give a compound of the formula

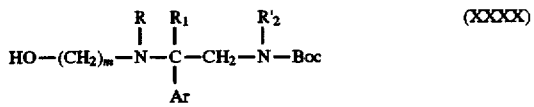

3') if appropriate, if $R'_2$ in the compound of formula (XXXIV) is an ω-hydroxy-($C_2$-$C_4$)-alkylene, the amine group is protected as indicated in step 2') and then the hydroxyl is protected, or the group $R'_2$ is optionally converted to $R"_2$, to give a compound of the formula

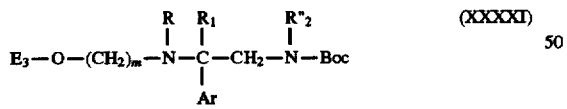

in which m, R, $E_3$, $R_1$ and Ar are as defined in claim 13 and $R"_2$ is an ω-($C_1$-$C_4$)-alkylcarbonyloxy-($C_2$-$C_4$)-alkylene, an ω-benzoyloxy-($C_2$-$C_4$)-alkylene, an ω-benzyloxy-($C_2$-$C_4$)-alkylene, an ω-formyloxy-($C_2$-$C_4$)-alkylene, an ω-$R_5$NHCOO—($C_2$-$C_4$)-alkylene, an ω-$R_8R_9$N—($C_2$-$C_4$)-alkylene, an ω-$R_{10}$CONR$_{11}$—($C_2$-$C_4$)-alkylene, an ω-$R_{12}$OCONR$_{11}$—($C_2$-$C_4$)-alkylene, an ω-$R_6R_7$NCONR$_{11}$—($C_2$-$C_4$)-alkylene or an ω-$R_{13}SO_2$NR$_{11}$—($C_2$-$C_4$)-alkylene, in which $R_5$ to $R_{13}$ are as defined for (I) in claim 1, and the protecting group $E_3$ is then selectively eliminated by acid hydrolysis to give the compound of the formula

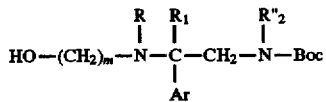

4') the compound (XXXX) or the compound (XXXXbis) is treated, it being understood that if $R'_2$ is an ω-hydroxy-($C_2$-$C_4$)-alkylene, the hydroxyl is protected, or if $R"_2$ is a group ω-$R_8R_9$N—($C_2$-$C_4$)-alkylene in which $R_8$ is a hydrogen and $R_9$ is as defined above, the amine is protected, with a compound of formula (XXIX) as defined in claim 12, to give the sulfonate of the formula

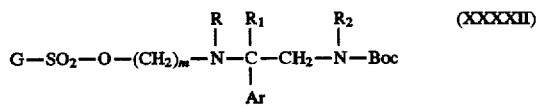

5') the compound (XXXXII) is reacted with a compound of formula (Xa), (Xc), (Xd), (Xe), (Xf), (Xg) or (Xh) as defined in claim 8, and Y" is optionally converted to Y', to give the compound of the formula

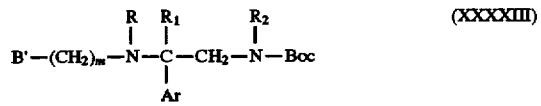

in which B' is a group $B_2$ $B_3$, $B_4$, $B_5$, $B_6$, $B_7$ or $B_8$ as defined above;

6') the N-protecting group of the compound (XXXXIII) is deprotected by treatment in a strong acid medium, for example HCl, to give the compound of the formula

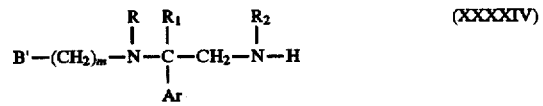

7') the compound of formula (XXXXIV) is reacted either with a halogenated derivative of the formula

in which Hal is a halogen atom and A and Z are as defined for (I) in claim 1, if $R_1$ and $R_2$ are separate and if it is intended to prepare a compound of formula (I) in which T is —$CH_2$—;

or with a functional derivative of an acid of the formula

in which A and Z are as defined above, if it is intended to prepare a compound of formula (I) in which T is —CO—;

or with a chloroformate of the formula

in which A and Z are as defined above, if it is intended to prepare a compound of formula (I) in which T is —COO—;

or with an isocyanate of the formula

in which A and Z are as defined above, if it is intended to prepare a compound of formula (I) in which T is a group —CO—NR$_4$— in which $R_4$ is a hydrogen;

or with a carbamoyl chloride of the formula

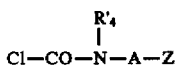

(IIId)

in which A and Z are as defined above and R'$_4$ is a (C$_1$–C$_4$)-alkyl group, if it is intended to prepare a compound of formula (I) in which T is —CO—NR$_4$— in which R$_4$ is a (C$_1$–C$_4$)-alkyl; and 8') after deprotection of the hydroxyl or amino groups, if appropriate, or optional conversion of Y" to Y', the product obtained in step 7') is optionally converted to a salt thereof with a mineral or organic acid.

15. A pharmaceutical composition in which a compound according to any one of claims 1 to 7 is present as the active principle.

16. A pharmaceutical composition according to claim 15 in the form of a dosage unit in which the active principle is mixed with at least one pharmaceutical excipient.

17. A composition according to claim 16 which contains from 0.5 to 1000 mg of active principle.

18. A composition according to claim 16 which contains from 2.5 to 250 mg of active principle.

19. A compound according to claim 2 of formula (I*) in which:

Z is Z' and is:
  a phenyl which is unsubstituted or monosubstituted or polysubstituted by a substituent selected from the group consisting of a halogen atom; a trifluoromethyl; a cyano; a hydroxyl; a nitro; an amino which is unsubstituted or monosubstituted or disubstituted by a (C$_1$–C$_4$)-alkyl; a benzylamino; a carboxyl; a (C$_1$–C$_{10}$)-alkyl; a (C$_3$–C$_8$)-cycloalkyl which is unsubstituted or monosubstituted or polysubstituted by a methyl; a (C$_1$–C$_{10}$)-alkoxy; a (C$_3$–C$_8$)-cycloalkoxy which is unsubstituted or monosubstituted or polysubstituted by a methyl; a mercapto; a (C$_1$–C$_{10}$)-alkylthio; a formyloxy; a (C$_1$–C$_6$)-alkylcarbonyloxy; a formylamino; a (C$_1$–C$_6$)-alkylcarbonylamino; a benzoylamino; a (C$_1$–C$_4$)-alkoxycarbonyl; a (C$_3$–C$_7$)-cycloalkoxycarbonyl; a carbamoyl which is unsubstituted or monosubstituted or disubstituted by a (C$_1$–C$_4$)-alkyl; a ureido which is unsubstituted or monosubstituted or disubstituted in the 3-position by a (C$_1$–C$_4$)-alkyl or a (C$_3$–C$_7$)-cycloalkyl; or a (pyrrolidin-1-yl) carbonylamino; said substituents being identical or different;
  a naphthyl which is unsubstituted or monosubstituted or polysubstituted by a halogen, a trifluoromethyl, a (C$_1$–C$_4$)-alkyl, a hydroxyl or a (C$_1$–C$_4$)-alkoxy; or
  a pyridyl, a thienyl, an indolyl, a quinolyl, a benzothienyl or an imidazolyl.

20. A compound according to claim 19 of formula (I*) in which simultaneously:

R$_1$ and R$_2$ together form a group —(CH$_2$)$_n$—CQ— in which n is equal to 2 and Q is H$_2$ or oxygen;

W$_1$ is an oxygen atom; and

Ar is a 3,4-dichlorophenyl or a 3,4-difluorophenyl;

or pharmaceutically acceptable salts and solvates thereof.

21. A compound according to claim 19 of formula (I*) in which simultaneously:

R$_1$ is hydrogen;

R$_2$ is a methyl group;

W$_1$ is an oxygen atom;

m is equal to 2; and

Ar is a 3,4-dichlorophenyl or a 3,4-difluorophenyl;

or pharmaceutically acceptable salts and solvates thereof.

22. A compound according to claim 19 of formula (I*) in which simultaneously:

R$_1$ is hydrogen;

R$_2$ is a methyl group;

W$_1$ is a group —NR— in which R is a methyl group; and

Ar is a 3,4-dichlorophenyl or a 3,4-difluorophenyl;

or pharmaceutically acceptable salts and solvates thereof.

23. A pharmaceutical composition in which a compound according to any one of claims 19 to 21 is present as the active principle.

24. A pharmaceutical composition according to claim 23 in the form of a dosage unit in which the active principle is mixed with at least one pharmaceutical excipient.

25. A composition according to claim 24 which contains from 0.5 to 1000 mg of active principle.

26. A composition according to claim 24 which contains from 2.5 to 250 mg of active principle.

* * * * *